(12) United States Patent  
Clemmer et al.

(10) Patent No.: US 9,129,782 B2  
(45) Date of Patent: Sep. 8, 2015

(54) ION MOBILITY SPECTROMETER AND METHOD OF OPERATING SAME

(71) Applicant: Indiana University Research and Technology Corporation, Indianapolis, IN (US)

(72) Inventors: David Edward Clemmer, Bloomington, IN (US); Michael A Ewing, Bloomington, IN (US); Steven M Zucker, Bloomington, IN (US); Christopher R. P. Conant, Bloomington, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 0 days.

(21) Appl. No.: 14/492,468

(22) Filed: Sep. 22, 2014

(65) Prior Publication Data

US 2015/0041637 A1  Feb. 12, 2015

Related U.S. Application Data

(63) Continuation of application No. 13/844,901, filed on Mar. 16, 2013, now Pat. No. 8,872,102, which is a continuation-in-part of application No. 12/952,109, filed on Nov. 22, 2010, now Pat. No. 8,513,591, which (Continued)

(51) Int. Cl.
*H01J 49/00* (2006.01)
*G01N 27/62* (2006.01)
*H01J 49/26* (2006.01)

(52) U.S. Cl.
CPC .......... *H01J 49/0031* (2013.01); *G01N 27/622* (2013.01); *H01J 49/26* (2013.01)

(58) Field of Classification Search
CPC ....................................................... H01J 49/00
USPC ............................................................ 250/281
See application file for complete search history.

(56) References Cited

U.S. PATENT DOCUMENTS 5,280,175 A   1/1994  Karl
6,815,671 B2  11/2004 Johnston et al.

(Continued)

OTHER PUBLICATIONS

Ewing, et al., Overtone Mobility Spectrometry: Part 5. Simulations and Analytical Expressions Describing Overtone Limits, Apr. 24, 2013, pp. 20, Journal of the American Society for Mass Spectrometry (United States).

(Continued)

*Primary Examiner* — Phillip A Johnston
(74) *Attorney, Agent, or Firm* — Barnes & Thornburg LLP

(57) ABSTRACT

In a drift tube partitioned into a plurality of cascaded drift tube segments each followed by an ion elimination region, for any integer M greater than 1, a method of separating ions repeats the following multiple times to cause only ions entering the drift tube that have a predefined ion mobility or range to traverse the drift tube: for each integer N beginning with 1 and sequentially advancing to M, establishing for a time duration an Nth electric repulsive field in the Nth ion elimination region and in every following Mth ion elimination region and an Nth electric drift field in each remaining ion elimination region and in each drift tube segment while deactivating for the time duration all non-Nth electric drift fields and non-Nth electric repulsive fields in each of the ion elimination regions and drift tube segments.

10 Claims, 31 Drawing Sheets

Related U.S. Application Data is a continuation-in-part of application No. 12/357,198, filed on Jan. 21, 2009, now Pat. No. 7,838,821.

(60) Provisional application No. 61/021,785, filed on Jan. 17, 2008.

(56) References Cited

U.S. PATENT DOCUMENTS

| | | | |
|---|---|---|---|
| 7,170,053 B2* | 1/2007 | Shvartsburg et al. | 250/287 |
| 7,388,197 B2 | 6/2008 | McLean et al. | |
| 7,838,821 B2 | 11/2010 | Clemmer et al. | |
| 7,943,901 B2* | 5/2011 | Wu | 250/288 |
| 8,513,591 B2 | 8/2013 | Clemmer et al. | |
| 8,872,102 B2* | 10/2014 | Clemmer et al. | 250/281 |
| 2009/0101810 A1 | 4/2009 | McLean et al. | |
| 2010/0193678 A1 | 8/2010 | Clemmer et al. | |
| 2010/0301206 A1* | 12/2010 | Brown et al. | 250/285 |

OTHER PUBLICATIONS

Lee, et al., Determination of Cross Sections by Overtone Mobility Spectrometry: Evidence for Loss of Unstable Structures at Higher Overtones, Sep. 30, 2010, pp. 10, Journal of Physical Chemistry, vol. 114, No. 38, 2010 (United States).

Giles, et al., Applications of a travelling wave-based radio-frequency-only stacked ring ion guide, Aug. 16, 2004, pp. 14, Rapid Communications in Mass Spectrometry, 2004 England, Published online in Wiley Interscience (www.interscience.wiley.com).

Pringle, et al., An investigation of the mobility separation of some peptide and protein ions using a new hybrid quadrupole/travelling wave IMS/oa-ToF instrument, Mar. 1, 2007, pp. 12, International Journal of Mass Spectrometry 261 (2007), available online at www.sciencedirect.com (England).

Giles, et al., Research Article—Enhancements in travelling wave ion mobility resolution, Mar. 13, 2011, pp. 8, Rapid Communications in Mass Spectrometry, Jun. 15, 2011, 25, 1559-1566, wileyonlinelibrary.com DOI: 10.1002 (England).

Rosell-Llompart, et al., Sizing Nanoparticles and Ions with a Short Differential Mobility Analyzer, Jan. 1, 1996, pp. 25, Journal of Aerosol Science, vol. 27, No. 5. pp. 695-719, (United Kingdom).

Rus, et al., IMS-MS Studies based on coupling a differential mobility analyzer (DMA) to commercial API-MS systems, Dec. 1, 2010, pp. 11, International Journal of Mass Spectrometry, vol. 298 pp. 30-40 (Netherlands).

Vidal-De-Miguel, et al., Transversal Modulation Ion Mobility Spectrometry (TM-IMS), A New Mobility Filter Overcoming Turbulence Related Limitations, Sep. 18, 2012, pp. 7, Analytical Chemistry pp. 7831-7837 (United States).

Fernandex-Lima, et al., Gas-phase separation using a trapped ion mobility spectrometer, Sep. 1, 2011, International Journal for Ion Mobility Spectrometry (Germany).

Purves, et al., Mass Spectrometric characterization of a high-field asymmetric waveform Ion mobility spectrometer, Dec. 1998, pp. 13, Review of Scientific Instruments, vol. 69, No. 12, pp. 4094-4105 (United States).

Shvartsburg, et al., High-Definition Differential Ion Mobility Spectrometry with Resolving Power up to 500, Jan. 1, 2013, pp. 6, Journal of the American Society of Mass Spectrometry, pp. 109-114 (United States).

Kurulugama, et al., Overtone Mobility Spectrometry: Part 1. Experimental Observations, May 2009, pp. 9, Journal of the American Society for Mass Spectrometry vol. 20, No. 5, 729-737 (United States).

Valentine, et al., Overtone Mobility Spectrometry: Part 2. Theoretical Considerations of Resolving Power, May, 2009, pp. 13, Journal of the American Society of Mass Spectrometry, vol. 20, No. 5, 738-750 (United States).

Valentine, et al., Overtone Mobility Spectrometry: Part 3. On the Origin of Peaks, May 1, 2011, pp. 13, Journal of the American Society of Mass Spectrometry vol. 22, No. 5, pp. 804-816 (United States).

Kurulugama, et al., Overtone Mobility Spectrometer: Part 4. OMS-OMS Analyses of Complex Mixtures, Nov. 1, 2011, pp. 12, Journal of the American Society of Mass Spectrometry, vol. 22, No. 11, pp. 2049-2060 (United States).

Koeniger, et al., An IMS-IMS Analogue of MS-MS, Jun. 15, 2006, pp. 14, Analytical Chemistry, vol. 78, No. 12.

Appelhans, et al., Simion ion optics simulations at atmospheric pressure, Jun. 15, 2005, pp. 14, International Journal of Mass Spectrometry, vol. 244, No. 1, pp. 1-14 (Netherlands).

Julian, et al., Ion Funnels for the Masses: Experiments and Simulations with a Simplified Ion Funnel, Oct., 2005, pp. 5, Journal of the American Society for Mass Spectrometry, vol. 16, No. 10, pp. 1708-1712 (United States).

Merenbloom, et al., High-Resolution Ion Cyclotron Mobility Spectrometry, Feb. 15, 2009, pp. 7, Analytical Chemistry, vol. 81, No. 4, pp. 1482-1487 (United States).

Kanu, et al., Ion mobility—mass spectrometry, Feb. 26, 2008, pp. 22, Journal of Mass Spectrometry, vol. 43, No. 1, pp. 1-22) (United Kingdom).

Valentine, et al., Developing liquid chromatography ion mobility mass spectometry techniques, Aug. 2005, pp. 13, Expert Review of Proteomics, vol. 2, No. 4, pp. 553-565 (England).

McLean, et al., Ion mobility-mass spectrometry: a new paradigm for proteomics, Feb. 1, 2005, pp. 15, International Journal of Mass Spectrometry, vol. 240, No. 3, 301-315 (Netherlands).

Isailovic, et al. Profiling of Human Serum Glycans Associated with Liver Cancer and Cirrhosis by IMS-MS, Mar. 2008, pp. 9, Journal of Proteome Research vol. 7, No. 3, pp. 1109-1117 (United States).

Williams, et al., Characterization of simple isomeric oligosaccharides and the rapid separation of glycan mixtures by ion mobility mass spectrometry, Dec. 1, 2010, pp. 9, International Journal of Mass Spectrometry, vol. 298, No. 1-3, 119-127 (Netherlands).

Bernstein, et al., Amyloid-B protein oligomerization and the importance of tetramers and dodecamers in the aetiology of Alzheimer's disease, Jul. 2009, pp. 6, Nature Chemistry, vol. 1, www.nature.com/naturechemistry.

Uetrecht, et al., Interrogating viral capsid assembly with ion mobility-mass spectrometry, Feb. 2011, pp. 7, Nature Chemistry, vol. 3, www.nature.com/naturechemistry.

Myung, et al., Development of High-Sensitivity Ion Trap Ion Mobility Spectrometry Time-of-Flight Techniques: A High-Throughput Nano-LC-IMS-TOF Separation of Peptides Arising from a *Drosophila* Protein Extract, Oct. 1, 2003, pp. 9, Analytical Chemistry, vol. 75, No. 19.

Dilger, et al., A database of alkali metal-containing peptide cross sections: Influence of metals on size parameters for specific amino acids, Dec. 15, 2012, pp. 11, International Journal of Mass Spectrometry, vol. 330-332 pp. 35-45 (Netherlands).

* cited by examiner

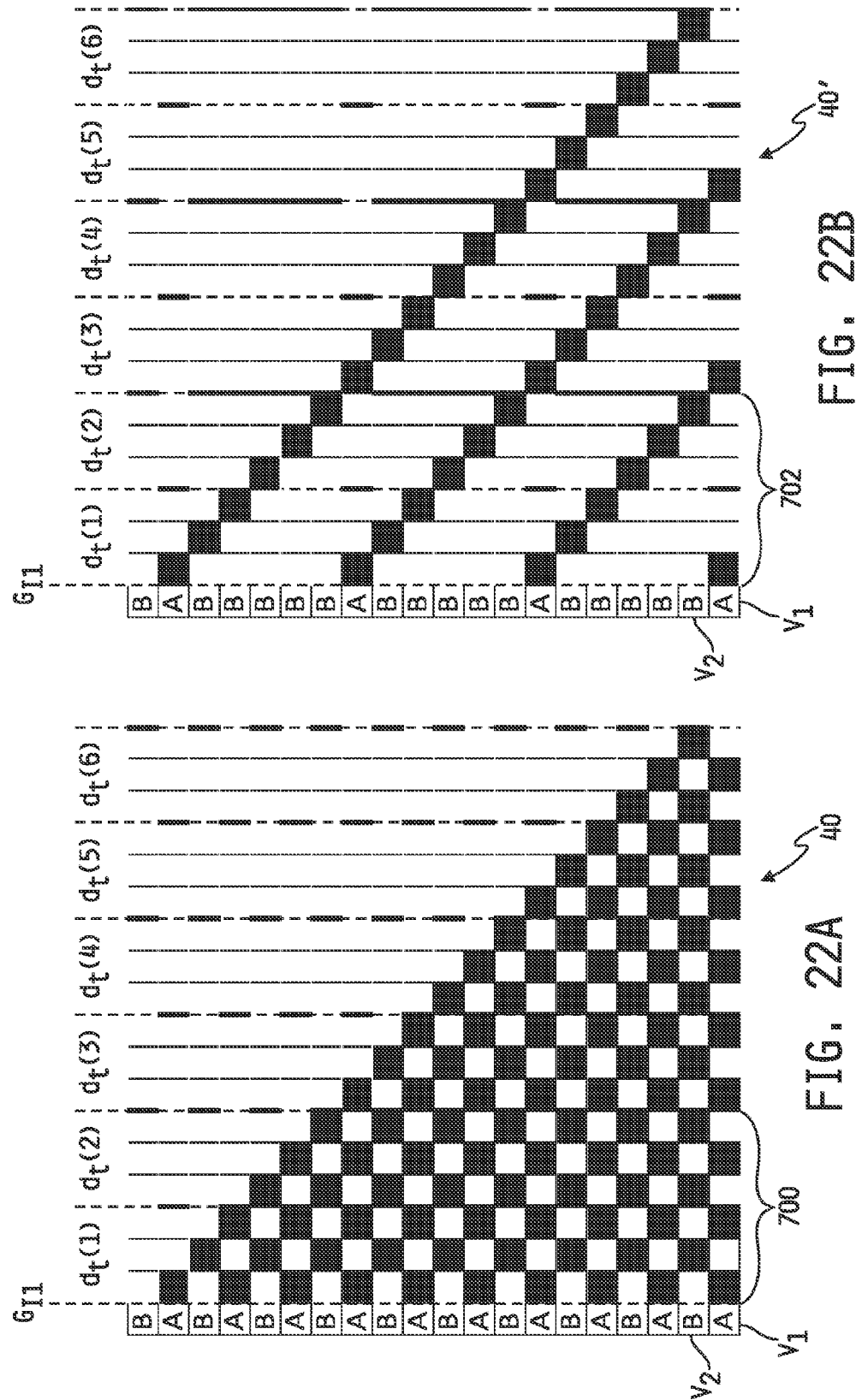

ION MOBILITY SPECTROMETER AND METHOD OF OPERATING SAME

CROSS-REFERENCE TO RELATED APPLICATIONS

This patent application is a continuation of U.S. patent application Ser. No. 13/844,901, which is a continuation-in-part of U.S. patent application Ser. No. 12/952,109, now U.S. Pat. No. 8,513,591, which is a continuation-in-part of U.S. patent application Ser. No. 12/357,198, now U.S. Pat. No. 7,838,821, which claims the benefit of, and priority to, U.S. Provisional Patent Application Ser. No. 61/021,785, the disclosures of which are all incorporated herein by reference in their entirety.

GOVERNMENT RIGHTS

This invention was made with government support under AG024547, RR018942 and 1RC1GM090797 awarded by the National Institutes of Health. The United States Government has certain rights in the invention.

FIELD OF THE INVENTION

The present invention relates generally to ion separation instruments, and more specifically to instruments that separate ions in time as a function of ion mobility.

BACKGROUND

Ion mobility spectrometers are analytical instruments that are used to separate ions in time as a function of ion mobility. It is desirable to be able to control electric fields applied to such instruments in order to investigate properties of charged particles.

SUMMARY

The present invention may comprise one or more of the features recited in the attached claims, and/or one or more of the following features and combinations thereof. An ion mobility spectrometer instrument may comprise a drift tube partitioned into a plurality of cascaded drift tube segments and ion elimination regions, each of the plurality of drift tube segments defining an ion inlet at one end, an ion outlet at an opposite end and a first distance between the ion inlet and the ion outlet, each of the plurality of ion elimination regions defining a second distance between the ion outlet of a different one of the plurality of drift tube segments and the ion inlet of the next adjacent drift tube segment of the plurality of cascaded drift tube segments, an ion source coupled to one of the plurality of cascaded drift tube segments, one of an ion detector and an ion inlet of at least another ion mobility spectrometer instrument arranged to receive ions exiting the drift tube, a number, M, of electric field activation sources each operatively connected to one or more of the plurality of drift tube segments such that, when activated, each establishes a repulsive electric field in a different one of the first M ion elimination regions and in every following Mth ion elimination region, and also establishes an electric drift field in all remaining ion elimination regions and in all of the plurality of cascaded drift tube segments, and a control circuit to sequentially activate a number of times each of the number, M, of electric field activation sources while deactivating the remaining number, M, of electric field activation sources, with at least one of the M electric field activation sources having a different activation time duration than activation times of others of the M electric field activation sources, to thereby cause only ions generated by the ion source that have a predefined ion mobility or range of ion mobilities to traverse the drift tube.

The plurality of cascaded drift tube segments and ion elimination regions may illustratively define a linear drift tube, wherein the ion source is coupled to the ion inlet of a first one of the cascaded drift tube segments, and wherein the one of the ion detector and the ion inlet of the at least another ion mobility spectrometer instrument is coupled by a last one of the plurality of ion elimination regions to the ion outlet of a last one of the plurality of drift tube segments. In this implementation, the ions generated at the ion source travel from the ion inlet of the first one of the cascaded drift tube segments through the last one of the plurality of ion elimination regions under the influence of electric drift fields established by the M electric field activation sources in the plurality of cascaded drift tube segments and ion elimination regions, and ions having ion mobilities or ranges of ion mobilities other than the predefined ion mobility or range of ion mobilities are filtered out by the repulsive electric fields established by each of the M electric field activation sources in a different one of the first M ion elimination regions and in every following Mth ion elimination region. In one embodiment of this implementation, the ion source may continuously generate ions, and the continuously generated ions may enter the first one of the cascaded drift tube segments under the influence of the electric drift field sequentially established by each of the plurality, M, of electric field activation sources in the first one of the cascaded drift tube segments. Alternatively, the ion inlet of the first one of the cascaded drift tube segments may comprise an ion gate, and the control circuit may control the ion gate to selectively allow entrance of discrete packets of ions generated by the ion source into the ion inlet of the first one of the cascaded drift tube segments.

In an alternative embodiment, the ion outlet of a last one of the drift tube segments is coupled by a last ion elimination region to the ion inlet of a first one of the drift tube segments such that the drift tube defines therein a closed and continuous ion travel path, and the ion mobility spectrometer may further comprise an ion entrance drift tube segment having an ion inlet coupled to the ion source and an ion outlet coupled to the one of the plurality of cascaded drift tube segments, an ion exit drift tube segment having an ion inlet coupled to the one or another one of the plurality of drift tube segments, and an ion outlet, and an ion gate arrangement responsive to a first set of one or more ion gate signals to direct ions moving through the drift tube through the one or another one of the plurality of cascaded drift tube segments while blocking the ions from entering the ion exit drift tube segment, and to a second set of one or more ion gate signals to direct the ions moving through the drift tube into the ion exit drift tube segment while blocking the ions from moving through the one or another one of the plurality of cascaded drift tube segments, wherein the control circuit may produce the first set of one or more ion gate signals to cause only ions supplied by the ion source that have the predefined ion mobility or range of ion mobilities to travel through the drift tube, and after the ions have traveled around the drift tube a selected number of times to produce the second set of one or more ion gate signals to draw ions moving through the drift tube out of the drift tube and into the ion exit drift tube segment where the ions exit via the ion mobility spectrometer via the ion outlet of the ion exit drift tube segment. The ion gate arrangement may comprise a first ion gate positioned in the one or another one of the plurality of cascaded drift tube segments, and a second ion gate positioned in or at the ion inlet of the ion exit drift tube segment, wherein the first set of one or more ion gate signals comprises a first ion gate signal to which the first ion gate is responsive to allow ions to pass therethrough and a second ion gate signal to which the second ion gate is responsive to block ions from passing therethrough, and wherein the second set of one or more ion gate signals comprises a third ion gate signal to which the first ion gate is responsive to block ions from passing therethrough and a fourth ion gate signal to which the second ion gate is responsive to allow ions to pass therethrough. In this implementation, ions generated at the ion source travel from the ion inlet of the first one of the cascaded drift tube segments through the last one of the plurality of ion elimination regions under the influence of electric drift fields established by the number, M, of electric field activation sources in the plurality of cascaded drift tube segments and ion elimination regions, and ions having ion mobilities or ranges of ion mobilities other than the predefined ion mobility or range of ion mobilities are filtered out by the repulsive electric fields established by each of the number, M, of electric field activation sources in a different one of the first M ion elimination regions and in every following Mth ion elimination region. In one embodiment of this implementation, the ion source may continuously generates ions, and at least one of the number, M, of electric field activation sources may establish an electric drift field in the ion entrance drift tube, and the continuously generated ions may enter the ion inlet of the ion entrance drift tube segment under the influence of the electric drift field established in the ion entrance drift tube. In an alternate embodiment of this implementation, the ion inlet of the ion entrance drift tube segment may comprise an ion gate, and the control circuit may control the ion gate to selectively allow entrance of discrete packets of ions generated by the ion source into the ion inlet of the ion entrance drift tube segment.

In either implementation, the ion source may comprise at least one ion separation instrument configured to separate ions in time as a function of one or more molecular characteristics.

In either implementation, each of the number, M, of electric field activation sources may be programmable, in one embodiment, to establish, when triggered, the electric drift and repulsive fields, and the control circuit may be configured to sequentially activate the number, M, of electric field activation sources for by sequentially triggering the number, M, of electric field activation sources. Alternatively, each of the number, M, of electric field activation sources may be programmable to establish, when triggered, the electric drift and repulsive fields, and the control circuit may be configured to sequentially activate the number, M, of electric field activation sources by triggering one of the number, M, of electric field activations sources with remaining ones of the number, M, of electric field activation sources being triggered by operation of a previously triggered one of the number, M, of electric field activation sources.

In either implementation, fundamental frequency is defined by a ratio of a total number of the plurality of drift tube segments and a total drift time of ions having the predefined ion mobility or range of ion mobilities through the drift tube under the influence of the electric fields established by the number, M, of electric field activation sources, and the control circuit may sequentially activate each of the number, M, of electric field activation sources while deactivating the remaining number, M, of electric field activation sources a number of times at a plurality of different activation durations to thereby produce ions exiting the drift tube at a number of different overtone frequencies that are functionally related to the fundamental frequency. The ion mobility spectrometer instrument may further comprise the ion detector coupled by a last one of the plurality of ion elimination regions to the ion outlet of a last one of the plurality of drift tube segments, and the ion detector may produce ion detection signals in response to detection of ions thereat, and the control circuit may convert the ion detection signals to the frequency domain for identification of ion intensity signals at the number of different overtone frequencies.

An ion mobility spectrometer instrument may comprise a drift tube partitioned into a plurality of cascaded drift tube segments and ion elimination regions, each of the plurality of drift tube segments defining an ion inlet at one end, an ion outlet at an opposite end and a first distance between the ion inlet and the ion outlet, each of the plurality of ion elimination regions defining a second distance between the ion outlet of a different one of the plurality of drift tube segments and the ion inlet of the next adjacent drift tube segment of the plurality of cascaded drift tube segments, an ion source coupled to one of the plurality of cascaded drift tube segments, one of an ion detector and an ion inlet of at least another ion mobility spectrometer instrument arranged to receive ions exiting the drift tube, an integer number, $\phi$, of electric field activation sources each operatively connected to one or more of the plurality of drift tube segments such that, when activated, each establishes a repulsive electric field in a different one of the first $\phi$ ion elimination regions and in every following $\phi$th ion elimination region, and also establishes an electric drift field in all remaining ion elimination regions and in all of the plurality of cascaded drift tube segments, and a control circuit to sequentially activate a number of times each of the integer number, $\phi$, of electric field activation sources for an activation duration while deactivating the remaining integer number, $\phi$, of electric field activation sources to thereby cause only ions generated by the ion source that have a predefined ion mobility or range of ion mobilities to traverse the drift tube, a ratio of the activation duration of one of the M electric field activation sources and the activation duration of at least one of the remaining electric field activation sources defining a phase ratio, $\zeta$, the control circuit to control the activation durations of each of the integer number, $\phi$, of electric field activation sources such that $\zeta > 0$ and $\zeta \neq 1$.

A fundamental frequency, $f_f$, is defined by a ratio of a total number of the plurality of drift tube segments and a total drift time of ions having the predefined ion mobility or range of ion mobilities through the drift tube under the influence of the electric fields established by the integer number, $\phi$, of electric field activation sources, and the control circuit may sequentially activate each of the integer number, $\phi$, of electric field activation sources while deactivating the remaining integer number, $\phi$, of electric field activation sources a number of times at a plurality of different activation durations to thereby produce ions exiting the drift tube at a number of different overtone frequencies, $f_h$, that are functionally related to the fundamental frequency, $f_f$, by the relationship $f_h = f_f[\phi h+1][(\phi-1)\zeta+1]/\phi$, where h defines an integer index beginning with zero and having a step size of 1. Alternatively or additionally, the control circuit may sequentially activate each of the integer number, $\phi$, of electric field activation sources while deactivating the remaining integer number, $\phi$, of electric field activation sources a number of times with a sum of the activation durations of each of the integer number, $\phi$, of electric field activation sources defined as a ratio of $\phi$ and the fundamental frequency, $f_f$, to thereby produce ions exiting the drift tube at an overtone, m, of the fundamental frequency defined by the relationship $m = (\zeta+1)/2$.

In a specific implementation of the ion spectrometer instrument, $\phi=2$ such that a first one of the two electric field activation sources, when activated, establishes a repulsive electric field in sequentially odd numbered ones of the plurality of ion elimination regions and an electric drift field in sequentially even numbered ones of the plurality of ion elimination regions and also in each of the plurality of cascaded drift tube segments, and a second one of the two electric field activation sources, when activated, establishes a repulsive electric field in sequentially even numbered ones of the plurality of ion elimination regions and an electric drift field in sequentially odd numbered ones of the plurality of ion elimination regions and also in each of the plurality of cascaded drift tube segments, and wherein the phase ratio, $\zeta$, is the ratio of the activation duration of the first one of the electric field activation sources and the activation duration of the second one of the electric field activation sources. In this implementation, a fundamental frequency, $f_f$, is defined by a ratio of a total number of the plurality of drift tube segments and a total drift time of ions having the predefined ion mobility or range of ion mobilities through the drift tube under the influence of the electric fields established by the two electric field activation sources, and the control circuit to sequentially activate one of the two electric field activation sources while deactivating the other of the two electric field activation sources a number of times at a plurality of different activation durations to thereby produce ions exiting the drift tube at a number of different overtone frequencies, $f_h$, that are functionally related to the fundamental frequency, $f_f$, by the relationship $f_h=f_f[2h+1][\zeta+1]/2$, where h defines an integer index beginning with zero and having a step size of 1. Alternatively or additionally, the control circuit may sequentially activate one of the two electric field activation sources while deactivating the other of the two electric field activation sources a number of times with a sum of the activation duration of the first one of the electric field activation sources and the activation duration of the second one of the electric field activation sources defined as a ratio of 2 and the fundamental frequency, $f_f$, to thereby produce ions exiting the drift tube at an overtone, m, of the fundamental frequency defined by the relationship $m=(\zeta+1)/2$.

A method is provided for separating ions as a function of ion mobility in a drift tube partitioned into a plurality of cascaded drift tube segments each defining an ion inlet at one end and an ion outlet at an opposite end, wherein the plurality of cascaded drift tube segments define an ion elimination region between an ion outlet of each drift tube segment and an ion inlet of an adjacent drift tube segment. The method may comprise deactivating a second electric repulsive field and a second electric drift field and establishing a first electric repulsive field in odd-numbered ones of the ion elimination regions while also establishing a first electric drift field in even-numbered ones of the ion elimination regions and in each of the drift tube segments for a first time duration, deactivating the first electric repulsive field and the first electric drift field and establishing the second electric repulsive field in even-numbered ones of the ion elimination regions while also establishing a second electric drift field in odd-numbered ones of the ion elimination regions and in each of the drift tube segments for a second time duration different than the first time duration, and sequentially repeating the two deactivating steps a number of times to thereby cause only ions entering the ion inlet of a first one of the plurality of cascaded drift tube regions that have a predefined ion mobility or range of ion mobilities to traverse the drift tube.

BRIEF DESCRIPTION OF THE DRAWINGS

FIG. 22A is a timing diagram illustrating a series of drift tube segments operated with a two-phase arrangement of electric field activation sources having equal activation durations selected to define the $3^{rd}$ overtone of the fundamental frequency of operation.

FIG. 22B is a timing diagram similar to FIG. 22A and illustrating the two-phase arrangement of electric field activation sources having unequal activation durations also selected to define the $3^{rd}$ overtone of the fundamental frequency of operation.

DESCRIPTION OF THE ILLUSTRATIVE EMBODIMENTS

For the purposes of promoting an understanding of the principles of the invention, reference will now be made to a number of illustrative embodiments shown in the attached drawings and specific language will be used to describe the same.

Figure 1:
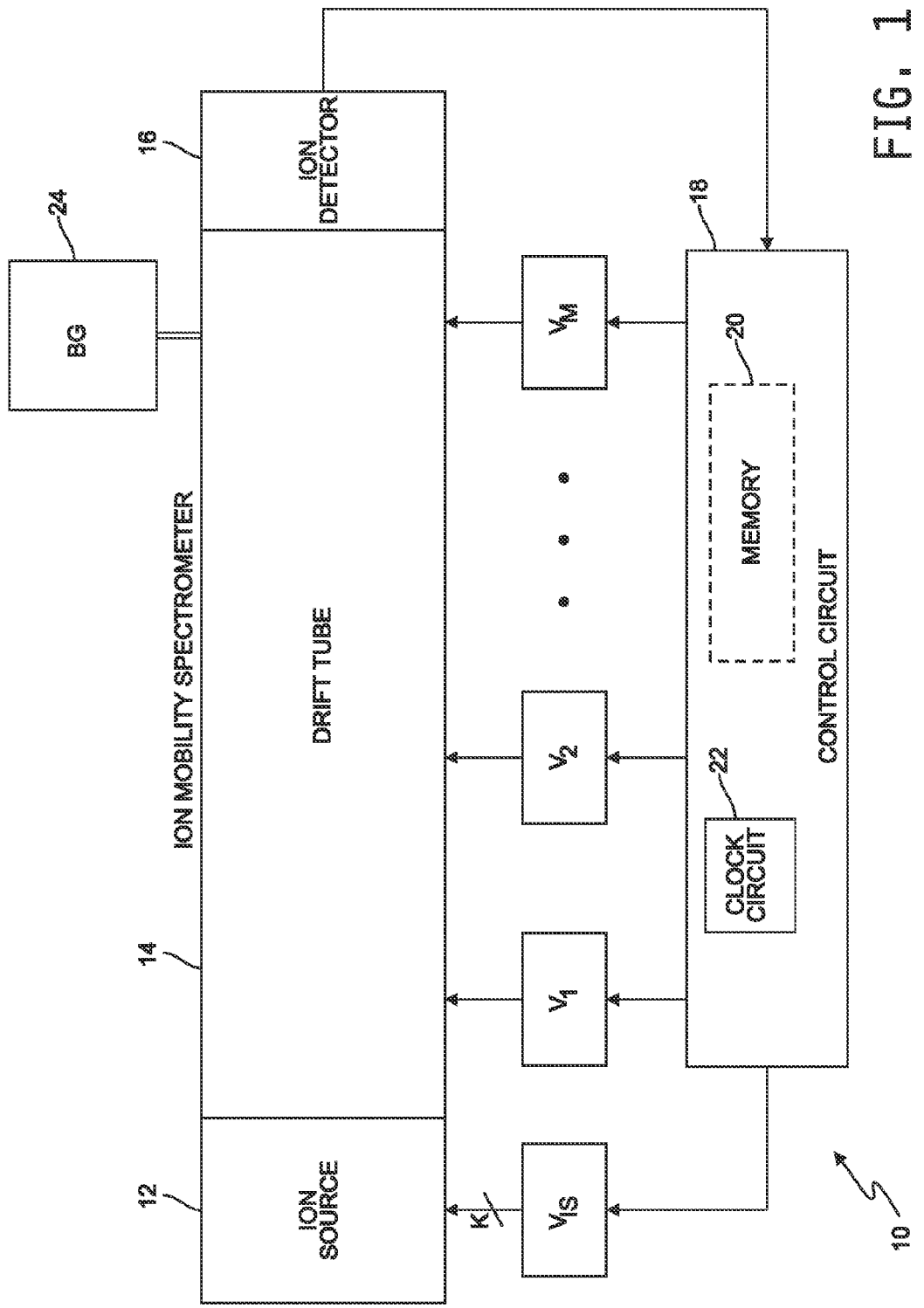
FIG. 1 is a block diagram of one illustrative embodiment of an ion mobility spectrometer instrument.

Referring to FIG. 1, a block diagram is shown of one illustrative embodiment of an ion mobility spectrometer instrument 10. In the illustrated embodiment, the ion mobility spectrometer instrument 10 includes an ion source 12 having an ion outlet that is couple to an ion inlet of a drift tube 14. An ion outlet of the drift tube 14 is coupled to an ion detector 16 having a signal output that is electrically connected to an input of a control circuit 18. The control circuit 18 includes a conventional memory unit 20, and further includes a conventional clock circuit 22 that may be controlled by the control circuit 18 in a conventional manner to produce periodic signals of desired frequency. Illustratively, a source of buffer gas 24 supplies buffer gas to the drift tube 14 in a conventional manner.

The control circuit 18 is electrically connected to a control input of an ion source voltage supply, $V_{IS}$, having a number, K, of outputs that are electrically connected to the ion source 12, where K may be any positive integer. The ion source 12 may be any conventional ion source that is configured to controllably produce ions from one or more samples. The ion source voltage supply, $V_{IS}$, may accordingly represent one or more voltage supplies configured to controllably produce, under the control of the control circuit 18 and/or manually controllable or programmable, one or more corresponding voltages for controlling operation of the ion source 12 in a conventional manner to produce ions. Illustratively, the ion source 12 may be configured to continuously produce ions, or may alternatively be configured to produce discrete packets of ions. Examples of such conventional ion sources include, but are not limited to, electrospray ion sources (ESI), ion sources using radiation source to desorb ions from a sample, e.g., matrix-assisted laser desorption ion sources (MALDI), ion sources that collect generated ions in an ion trap for subsequent release, and the like. Alternatively or additionally, the ion source 12 may be or include one or more conventional ion separation instruments configured to separate ions in time as a function of one or more molecular characteristics. Examples include, but are not limited to, a conventional liquid or gas chromatograph, a conventional mass spectrometer, a conventional ion mobility spectrometer, a capillary electrophoresis instrument, or the like. In any case, ions produced by the ion source 12 exit an ion outlet of the ion source 12 and enter an ion inlet of the drift tube 14 of the ion mobility spectrometer instrument 10.

The ion mobility spectrometer 10 further includes a number, M, of electric field activation sources, e.g., voltage sources, $V_1$-$V_M$, where M may be any positive integer greater than 1. In the illustrated embodiment, the control circuit 18 includes a corresponding number of outputs, each of which is electrically connected to an input of a different one of the electric field activation sources, $V_1$-$V_M$. In alternate embodiments, the control circuit 18 may include fewer outputs that are electrically connected to corresponding inputs of fewer of the electric field activation sources, $V_1$-$V_M$. In such embodiments, some of which will be described in detail hereinafter, one or more of the electric field activation sources, $V_1$-$V_M$, may be electrically connected to corresponding outputs of the control circuit 18 and one or more others of the electric field activation sources, $V_1$-$V_M$, may be triggered by operation of an adjacent or other ones of the electric field activation sources, $V_1$-$V_M$, and/or be programmed for specified operation. In any case, the outputs of the voltage sources $V_1$-$V_M$ are electrically connected to the drift tube 14 in a manner that will be fully described in detail hereinafter.

In the illustrated embodiment, the ion detector 16 is conventional and is configured to produce an ion intensity signal that is proportional to the number of ions that reach, and are detected by, the ion detector 16. The ion intensity signal is supplied to the control circuit 18, which then processes the ion intensity signal to produce ion mobility spectral information. The memory unit 20 has instructions stored therein that are executable by the control circuit 18 to control the operation of the various electric field activation sources, $V_1$-$V_M$.

In the embodiment illustrated in FIG. 1, the drift tube 14 is partitioned into a plurality of cascaded drift tube segments beginning with a first drift tube segment positioned adjacent to the ion source 12 and defining the ion inlet of the drift tube 14, and ending with an Nth drift tube segment defining the ion outlet of the drift tube 14. Ions generated by the ion source 12 enter the ion inlet of the drift tube 14, and the electric field activation sources, $V_1$-$V_M$, are operated such that the electric fields, i.e., drift fields, established in the various drift tube segments are modulated at a frequency that allows only ions having mobilities that are resonant with the operating conditions to drift through all of the various drift tube segments. In this way, the ion mobility spectrometer 10 operates as an ion mobility filter that filters out or away all ions except those having ion mobilities that are within a specified range of ion mobilities defined by the frequency of operation of the electric field activation sources, $V_1$-$V_M$. Additionally, ions drift through the various drift tube segments at frequencies that are overtones of the frequency of operation of the electric field activation sources, $V_1$-$V_M$. Thus, the ion mobility spectrometer 10 may be operated, as will be described in detail herein, to filter away all ions except those having ion mobilities that are resonant with a fundamental frequency, $f_f$, and/or associated overtone frequencies, of operation of the electric field activation sources, $V_1$-$V_M$. Because of the ability to selectively transmit ions in different frequency regions, including those associated with higher overtones, the techniques described herein may be referred to as Overtone Mobility Spectrometry (OMS). In this document, the terms "harmonics" should be understood to include the fundamental frequency, $f_f$, and integer multiples of the fundamental frequency, and the term "overtone" should be understood to include only the integer multiples of the fundamental frequency, $f_f$.

Figure 2:
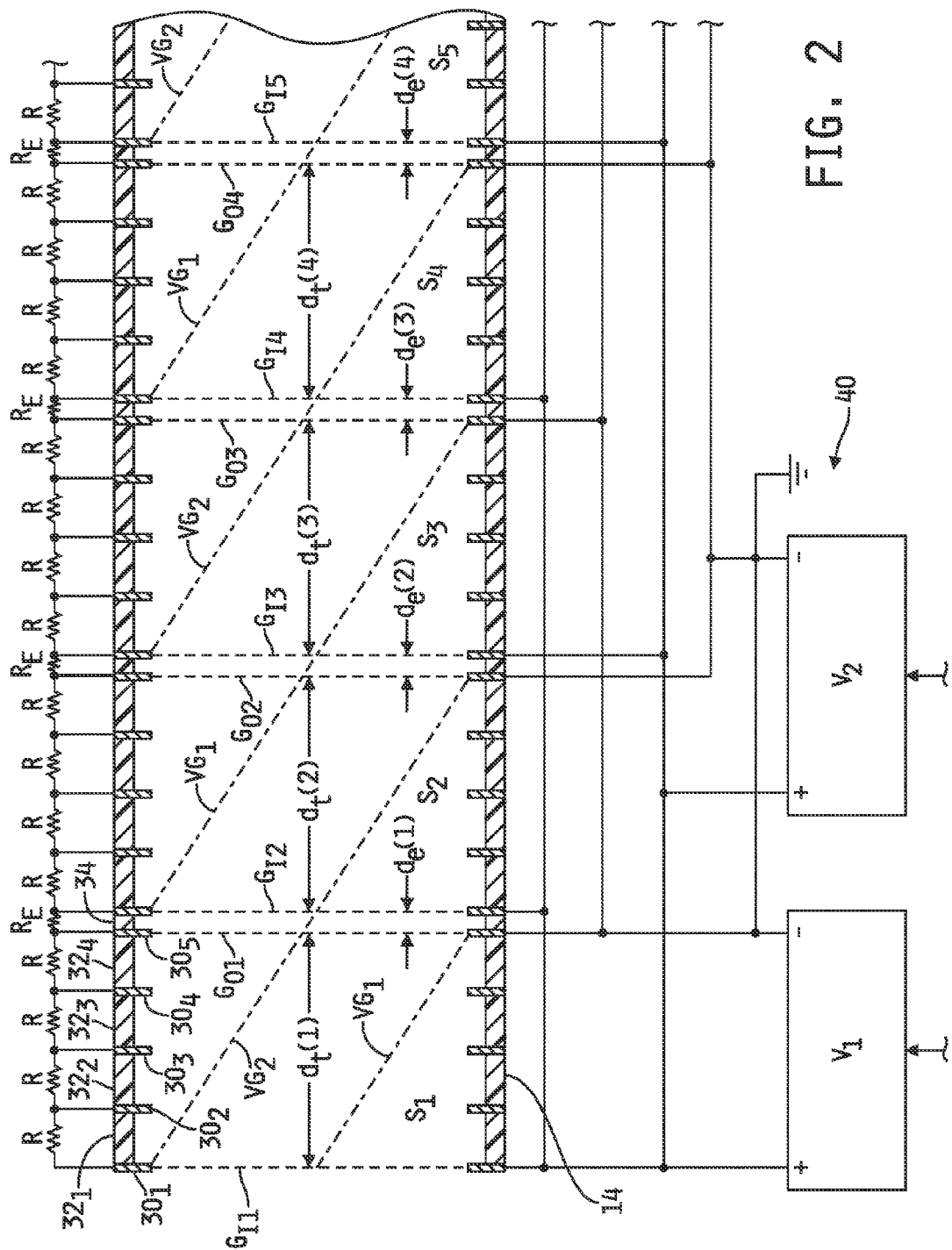
FIG. 2 is a diagram of one illustrative embodiment of the drift tube and associated arrangement of the electric field activation sources of the ion mobility spectrometer of FIG. 1.

Referring now to FIG. 2, a diagram is shown of one illustrative embodiment of a portion of the drift tube 14 along with one illustrative arrangement of the electric field activation sources of the ion mobility spectrometer 10 of FIG. 1. In the illustrated embodiment, the drift tube 14 is partitioned into a number, N, of cascaded segments, $S_1$-$S_N$, where N may be any positive integer greater than 2, and segments $S_1$-$S_5$ are shown in FIG. 2. Each of the segments, e.g., $S_1$-$S_5$, is illustratively constructed of five concentric, electrically conductive rings, $30_1$-$30_5$, each separated by a concentric, electrically insulating ring $32_1$-$32_4$ (illustrated in FIG. 2 for the segment $S_1$ only). The first electrically conductive ring, $30_1$, of each segment defines an ion inlet gate, $G_I$, to the segment, and the last electrically conductive ring, $30_5$, of each segment defines an ion outlet gate, $G_O$, of the segment. Illustratively, the first and last rings $30_1$ and $30_5$ contain mesh grids, e.g., 90% transmittance Ni mesh grid, although this disclosure contemplates embodiments which do not include one or both of the rings $30_1$ and $30_5$. In any case, adjacent ones of the electrically conductive rings, $30_1$-$30_5$, are separated by one of the electrically insulating rings, $32_1$-$32_4$, and adjacent segments, $S_1$-$S_N$, of the drift tube 14 are separated by a concentric, electrically insulating isolator ring 34, e.g., Teflon®, a synthetic fluoropolymer resin. All of the rings, $30_1$-$30_5$, $32_1$-$32_4$ and 34 are stacked together, sealed with O-rings and compressed using a number, e.g., eight, of threaded rods, e.g., nylon. The segments, $S_1$-$S_N$, are then joined together to form the drift tube 14.

In the illustrated embodiment, a resistor, R, is electrically connected between each of the electrically conductive rings in each drift tube segment, and a resistor $R_E$ is connected between the ion outlet gate and ion inlet gate of each adjacent drift tube segment. The drift tube 14 of the ion mobility spectrometer instrument 10 is constructed with the electrically conductive rings $30_1$-$30_5$ electrically insulated from each other and with the drift tube segments $S_1$-$S_N$ also electrically isolated from each other so that electric fields can be developed separately and independently in each of the segments $S_1$-$S_N$ and/or in groups of the segments $S_1$-$S_N$. By applying suitable voltages across the drift tube segments and/or groups of drift tube segments, as will be described in greater detail hereinafter, uniform electric fields are illustratively established in each drift tube segment in a manner that transmits ions generated by the ion source 12 through the drift tube 14 and through the ion outlet of the last segment $S_N$.

The region between the ion inlet gate and the ion outlet gate of each drift tube segment defines an ion transmission region of distance, $d_t$, and the region between the ion outlet gate of one drift tube segment and the ion inlet gate of the next adjacent drift tube segment defines an ion elimination region of distance, $d_e$. Thus, for example, the drift tube segment $S_1$ has an ion transmission region of distance, $d_t(1)$ defined between $G_{I1}$ and $G_{O1}$, and an ion elimination region of distance $d_e(1)$ defined between $G_{O1}$ and $G_{I2}$.

In one example embodiment, the drift tube 14 is constructed of 21 identical drift tube segments as just described, with an ion focusing funnel (not shown) positioned approximately mid way between the ion inlet and the ion outlet of the drift tube 14. In this example embodiment, the ion transmission region, $d_t$, and the ion elimination region, $d_e$, are together 5.84 cm in length, and the total length of the 22-section drift tube 14 is 128.5 cm from the ion inlet to the ion outlet of the drift tube 14. Further details relating to this example construction of the drift tube 14, including construction of the ion focusing funnel, are provided in co-pending U.S. Patent Application Pub. No. US 2007/0114382 A2, the disclosure of which is incorporated herein by reference. It will be understood, however, that this disclosure contemplates other embodiments in which the drift tube 14 is constructed in accordance with other conventional techniques, portions or the entirety of which may be linear or non-linear. For example, the drift tube 14 may alternatively be provided in the form of a circular or cyclotron drift tube, and further details relating to some example circular or cyclotron drift tube arrangements are provided in co-pending PCT Publication No. WO 2008/028159 A2, filed Aug. 1, 2007, the disclosure of which is incorporated herein by reference. It will be understood, however, that in any such alternate configuration the drift tube will define a number of cascaded drift tube sections such that electric fields may be selectively and separately created in individual and/or groups of the drift tube sections.

In the embodiment illustrated in FIG. 2, one illustrative arrangement 40 of the electric field activation sources, $V_1$-$V_M$, is shown that includes two electric field activation sources, $V_1$ and $V_2$, electrically connected to the drift tube 14. The control circuit 18 is illustratively configured to control operation of the electric field activation sources, $V_1$ and $V_2$, e.g., in accordance with instructions stored in the memory 20 that are executable by the control circuit 18, in an alternating fashion to generate electric fields within the drift tube segments, $S_1$-$S_N$, which cause ions of a specified range of ion mobilities to drift through the drift tube 14.

In the illustrated embodiment, the electric field activation sources $V_1$ and $V_2$ are both conventional DC voltage sources that are controllable by the control circuit 18 to produce a desired DC voltage across the + and − terminals. The + terminals of $V_1$ and $V_2$ are both electrically connected to the ion inlet gate, $G_{I1}$, of the first drift tube segment, $S_1$. The + terminal of $V_1$ is further electrically connected to the ion inlet gates of the even-numbered drift tube segments, e.g., to the ion inlet gate, $G_{I2}$ of the second drift tube segment, $S_2$, the ion inlet gate, $G_{I4}$, of the fourth drift tube segment, $S_4$, etc., and the + terminal of $V_2$ is further electrically connected to the ion inlet gates of the odd-numbered drift tube segments, e.g., to the ion inlet gate, $G_{I3}$ of the third drift tube segment, $S_3$, the ion inlet gate, $G_{I5}$, of the fifth drift tube segment, $S_5$, etc. The − terminal of $V_1$ is electrically connected to the ion outlet gates of the odd-numbered drift tube segments, e.g., to the ion outlet gates, $G_{O1}$, $G_{O3}$, $G_{O5}$, etc. of the drift tube segments $S_1$, $S_3$, $S_5$, etc., respectively. The − terminal of $V_2$ is electrically connected to the ion outlet gates of the even-numbered drift tube segments, e.g., to the ion outlet gates, $G_{O2}$, $G_{O4}$, $G_{O6}$, etc. of the drift tube segments $S_2$, $S_4$, $S_6$, etc., respectively. With the exception of $V_1$ connected across the ion inlet and ion outlet gates, $G_{I1}$ and $G_{O1}$ of the first drift tube segment, $S_1$, $V_1$ and $V_2$ are thus connected across the ion inlet and outlet gates of alternating, adjacent pairs of drift tube segments. For example, $V_2$ is electrically connected across $S_1$ and $S_2$, e.g., between $G_{I1}$ and $G_{O2}$, $V_1$ is electrically connected across $S_2$ and $S_3$, e.g., between $G_{I2}$ and $G_{O3}$, $V_2$ is electrically connected across $S_3$ and $S_4$, e.g., between $G_{I3}$ and $G_{O4}$, etc.

As illustrated in FIG. 2, the voltage sources, $V_1$ and $V_2$, when activated, produce linear voltage gradients, $VG_1$ and $VG_2$ respectively, across the drift tube segments to which they are connected. Equal-valued resistors, R, are electrically connected across adjacent pairs of the electrically conductive rings, $30_1$-$30_5$, of each drift tube segment, $S_1$-$S_N$, and equal-valued resistors, $R_E$, are connected between the ion outlet gates and ion inlet gates of adjacent pairs of drift tube segments. The value of $R_E$ is selected relative to R (or vice versa) such that the linear voltage gradients, $VG_1$ and $VG_2$, establish corresponding, constant-valued electrical fields across the various drift tube segment pairs.

The control circuit 18 is configured to control operation of the voltage sources, $V_1$ and $V_2$, by periodically switching one voltage source, $V_1$, $V_2$, on while the other voltage source, $V_1$, $V_2$, is off. This has the effect of alternately establishing a constant electric field across sequential, cascaded pairs of the drift tube segment, $S_1$-$S_N$. This generally allows only ions having ion mobilities that match the switching frequency to traverse each cascaded pair of drift tube segments. The periodic switching between $V_1$ and $V_2$ also establishes a repulsive electric field, i.e., an electric field that is oriented to repel ions traveling in a direction toward the ion detector 16, in the ion elimination regions, $d_e$, that follow each cascaded pair of drift tube segments. To illustrate this repulsive electric field, consider the case when $V_1$ is off and $V_2$ is on so that only the voltage gradients $VG_2$ of FIG. 2 exist. Ions entering the first drift tube segment $S_1$ will drift under the constant electric field established by $VG_2$ while $V_2$ is on. However, ions that reach $G_{O2}$ while $V_2$ is still on will be filtered out by the repulsive electric field, e.g., reverse electric field, established between the high +$V_2$ potential at the ion inlet gate $G_{I3}$ and the low −$V_2$ potential at the ion outlet gate $G_{O2}$. Generally, $V_2$ establishes, when activated, repulsive electric fields in the ion elimination regions $d_e$ between the ion outlet gates of even-numbered drift tube segments and the ion inlet gates of the next sequential, odd-numbered drift tube segments, and $V_1$ likewise establishes, when activated, identical repulsive electric fields in the ion elimination regions $d_e$ between the ion outlet gates of odd-numbered drift tube segments and the ion inlet gates of the next sequential, even-numbered drift tube segments. This periodic traversal of two drift tube segments and ion elimination in the activated ion elimination regions, $d_e$, causes only ions having ion mobilities that drift in the established electric fields at the rate defined by the $V_1$, $V_2$ switching rate and overtones thereof to drift through the length of the drift tube 14 to the ion detector 16. Generally, if the switching rate between $V_1$ and $V_2$ is constant, this switching rate defines a fundamental frequency, $f_f$, at which ions of a corresponding range of mobilities can travel progressively through the drift tube segments $S_1$-$S_N$. Alternatively or additionally, if the switching rate is swept over a range of switching rates, ions having the corresponding range of ion mobilities will also travel progressively through the drift tube segments $S_1$-$S_N$ at overtone frequencies of the fundamental frequency, $f_f$.

Figure 3:
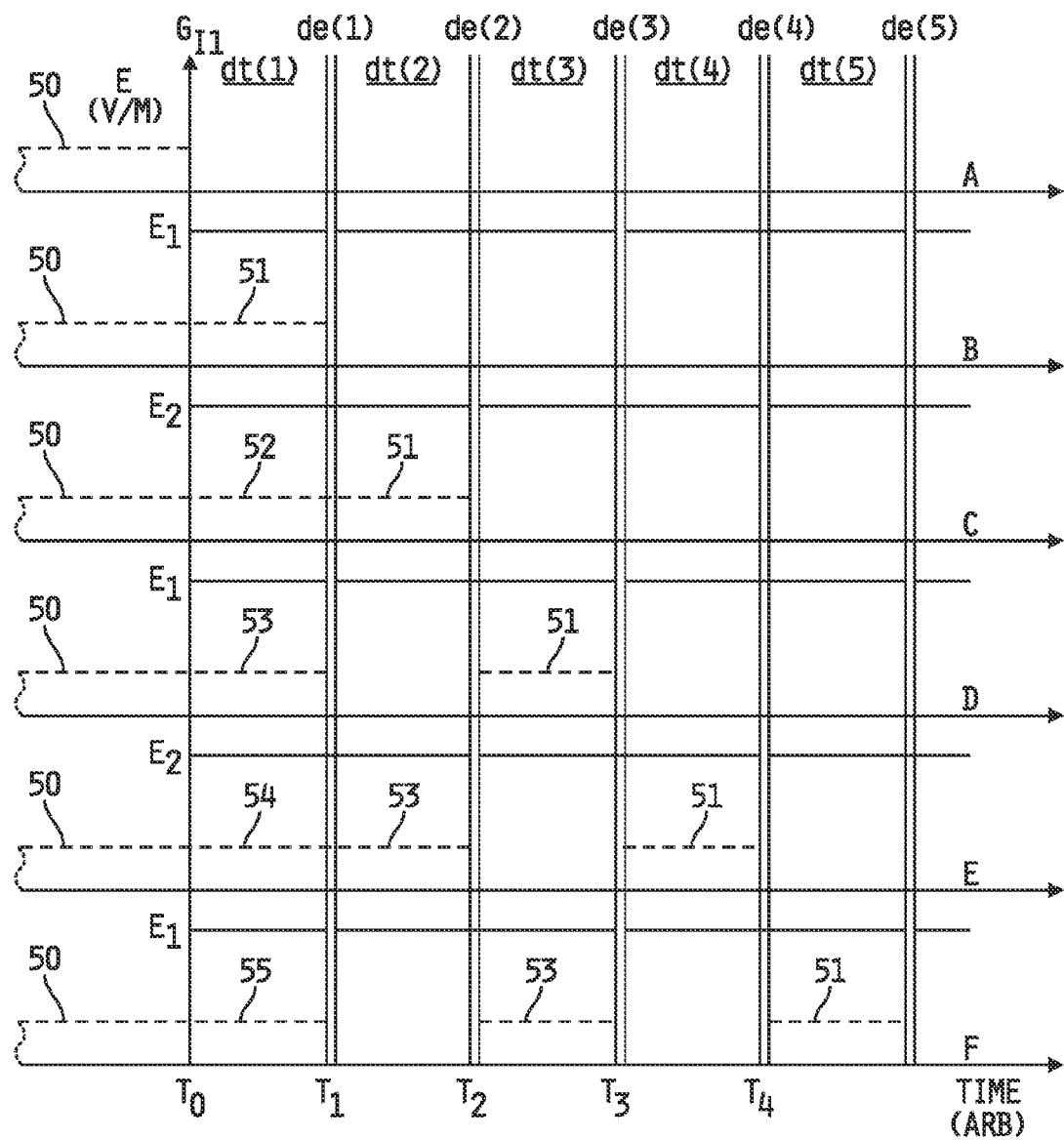
FIG. 3 is a timing diagram illustrating operation of the ion mobility spectrometer of FIGS. 1 and 2.

Referring now to FIG. 3, a number of plots A-F are shown demonstrating the progression of ions through the first five segments, $S_1$-$S_5$ of the drift tube 14 of FIGS. 1 and 2 when the voltage sources $V_1$ and $V_2$ are alternatively switched on and off. In the example illustrated in FIG. 5, the ion source 12 is configured to continually produce ions 50. Plot A illustrates the condition when $V_1$ and $V_2$ are both initially off. Plot B illustrates the condition when $V_1$ is subsequently turned on while $V_2$ remains off, which establishes a constant-valued electric field, $E_1$, in the ion transmission regions $d_f$ of each of the drift tube segments, $S_1$-$S_5$, and also in the even-numbered ion elimination regions $d_e(2)$ and $d_e(4)$, and which establishes a repulsive electric field in the odd-numbered ion elimination regions $d_e(1)$, $d_e(3)$ and $d_e(5)$. A portion 51 of the continually generated ions 50 drift through $d_f(1)$ under the influence of the electric field $E_1$ toward $d_f(2)$. However, ions that arrive at the ion elimination region $d_e(1)$ before $V_1$ is switched off are filtered out of the ions 51 by the repulsive field established in the ion elimination region $d_e(1)$ by $V_1$. It will be understood that the voltage applied by $V_1$ across the first drift tube segment, $S_1$, will be different than that applied across remaining pairs of the drift tube segments as illustrated in FIG. 2. Generally, the voltage applied by $V_1$ across the first drift tube segment, $S_1$, will be selected so as to establish an electric field, $E_1$, in the ion transmission region $d_t(1)$ that is identical to the electric field $E_1$ established across various pairs of the remaining drift tube segments, $S_2$-$S_N$.

Plot C illustrates the condition when $V_1$ is switched off and $V_2$ is switched on, which establishes a constant-valued electric field, $E_2$ ($E_2$=$E_1$), in the ion transmission regions $d_t$ of each of the drift tube segments, $S_1$-$S_5$, and also in the odd-numbered ion elimination regions $d_e(1)$, $d_e(3)$ and $d_e(5)$, and which establishes a repulsive electric field in the even-numbered ion elimination regions $d_e(2)$ and $d_e(4)$. The portion of ions 51 in the $d_t(1)$ region continues to advance under the influence of the electric field $E_2$ through $d_t(2)$ toward $d_t(3)$, and another portion 52 of the continually generated ions 50 drifts through $d_t(1)$ under the influence of the electric field $E_2$ toward $d_t(2)$. Ions that arrive at the ion elimination region $d_e(2)$ before $V_2$ is switched off are filtered out of the ions 51 by the repulsive field established in the ion elimination region $d_e(2)$ by $V_2$.

Plot D illustrates the condition when $V_2$ is switched off and $V_1$ is switched back on, which establishes the constant-valued electric field $E_1$ as described with respect to plot B. The portion of ions 51 in the $d_t(2)$ region continues to advance under the influence of the electric field $E_1$ through $d_t(3)$ toward $d_t(4)$, and another portion 53 of the continually generated ions 50 drifts through $d_t(1)$ under the influence of the electric field $E_1$ toward $d_t(2)$. However, the ions 52 that were previously in the $d_t(1)$ region are filtered away by the repulsive electric field established in the ion elimination region $d_e(1)$ and therefore do not advance to $d_t(2)$, and ions that arrive at the ion elimination regions $d_e(1)$ and $d_e(3)$ before $V_1$ is switched off are filtered out of the ions 53 and 51 respectively by the repulsive field established in the ion elimination regions $d_e(1)$ and $d_e(3)$ respectively.

Plot E illustrates the condition when $V_1$ is again switched off and $V_2$ is switched back on, which establishes the constant-valued electric field, $E_2$ described with respect to plot C. The portion of ions 51 in the $d_t(3)$ region continues to advance under the influence of the electric field $E_2$ through $d_t(4)$ toward $d_t(5)$, the portion of ions 53 in the $d_t(1)$ region continues to advance under the influence of the electric field $E_2$ through $d_t(2)$ toward $d_t(3)$, and yet another portion 54 of the continually generated ions 50 drifts through $d_t(1)$ under the influence of the electric field $E_2$ toward $d_t(2)$. Ions that arrive at the ion elimination regions $d_e(2)$ and $d_e(4)$ before $V_2$ is switched off are filtered out of the ions 53 and 51 respectively by the repulsive field established in the ion elimination regions $d_e(2)$ and $d_e(4)$ respectively.

Plot F illustrates the condition when $V_2$ is again switched off and $V_1$ is switched back on, which establishes the constant-valued electric field $E_1$ as described with respect to plot B. The portion of ions 51 in the $d_t(4)$ region continues to advance under the influence of the electric field $E_1$ through $d_t(5)$ toward the next drift tube segment ($S_6$), the portion of ions 53 in the $d_t(2)$ regions continues to advance under the influence of the electric field $E_1$ through $d_t(3)$ toward $d_t(4)$, and yet another portion 55 of the continually generated ions 50 drifts through $d_t(1)$ under the influence of the electric field $E_1$ toward $d_t(2)$. The ions 54 that were previously in the $d_t(1)$ region are filtered away by the repulsive electric field established in the ion elimination region $d_e(1)$ and therefore do not advance to $d_t(2)$, and ions that arrive at the ion elimination regions $d_e(3)$ and $d_e(5)$ before $V_1$ is switched off are filtered out of the ions 53 and 51 respectively by the repulsive fields established in the ion elimination regions $d_e(3)$ and $d_e(5)$ respectively.

Figure 4:
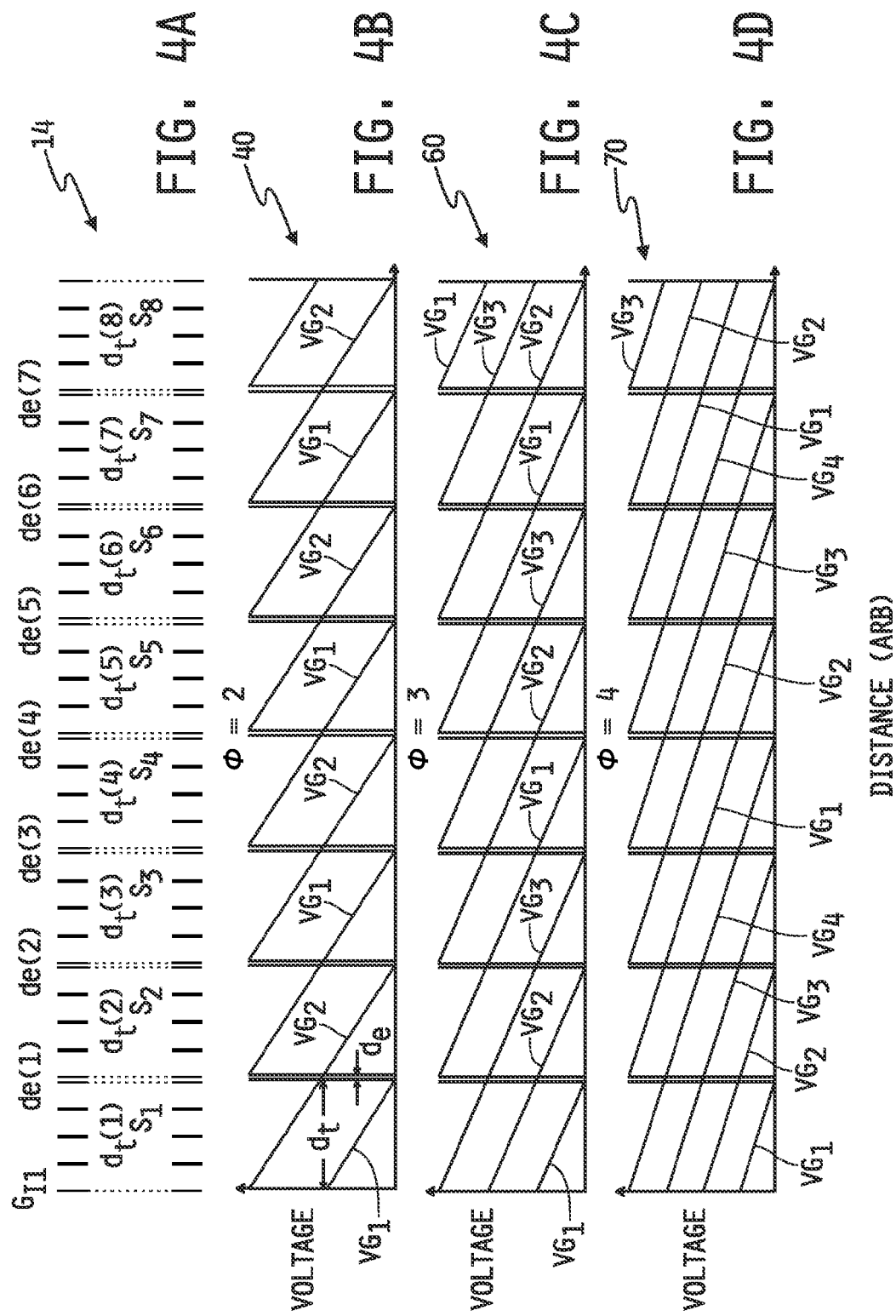
FIG. 4A is a diagram of one several cascaded sections of the drift tube illustrated in FIG. 2.
FIGS. 4B-4D illustrate alternate embodiments of the arrangement of the electric field activation sources relative to the drift tube of FIG. 4A.

While the embodiment of the drift tube 14 of FIG. 2 was illustrated and described as including an arrangement 40 of electric field activation sources in the form of two DC voltage sources, $V_1$ and $V_2$, it will be understood that this disclosure is not so limited and that embodiments are contemplated in which the arrangement of electric field activation sources includes more than two voltage sources. Referring now to FIGS. 4A-4D, for example, a number of voltage gradient plots are shown, in relation to the first eight cascaded segments, $S_1$-$S_8$, of the drift tube 14, that illustrate alternative embodiments in which the arrangement of electric field activation sources include additional voltage sources. As a reference, the voltage gradient plot 40 of FIG. 4B, illustrates the embodiment just described in which the arrangement of electric field activation sources includes two voltage sources $V_1$ and $V_2$ connected and configured to produce the two illustrated voltage gradients $VG_1$ and $VG_2$.

The voltage gradient plot 60 of FIG. 4C, in contrast, illustrates an embodiment in which the arrangement of electric field activation sources includes three voltage sources, $V_1$, $V_2$ and $V_3$, each illustratively identical to the voltage sources $V_1$ and $V_2$ illustrated and described with respect to FIG. 2. In the embodiment of FIG. 4C, $+V_1$, $+V_2$ and $+V_3$ are all electrically connected to the ion inlet gate $G_{I1}$ of the first drift tube segment, $S_1$. The $+V_1$ is further electrically connected to the ion inlet gates $G_{I2}$, $G_{I5}$ and $G_{I8}$, of the drift tube segments $S_2$, $S_5$ and $S_8$ respectively, the $+V_2$ is further electrically connected to the ion inlet gates $G_{I3}$, and $G_{I6}$, of the drift tube segments $S_3$ and $S_6$ respectively, and the $+V_3$ is further electrically connected to the ion inlet gates $G_{I4}$, and $G_{I4}$, of the drift tube segments $S_4$ and $S_7$ respectively. The $-V_1$ is electrically connected to the ion outlet gates $G_{O1}$, $G_{O4}$ and $G_{O7}$, the $-V_2$ is electrically connected to the ion outlet gates $G_{O2}$, $G_{O5}$ and $G_{O8}$, and the $-V_3$ is electrically connected to the ion outlet gates $G_{O3}$ and $G_{O6}$. In the three voltage source arrangement, the voltage sources $V_1$-$V_3$ are thus electrically connected, in alternating fashion, across three consecutive drift tube segments with all three voltage sources electrically connected to the ion inlet grid $G_{I1}$ of the first drift tube segment, $S_1$, and then with $V_1$ electrically connected across $S_1$, $S_2$-$S_4$, and $S_5$-$S_7$, with $V_2$ electrically connected across $S_1$-$S_2$, $S_3$-$S_5$ and $S_6$-$S_8$ and with $V_3$ electrically connected across $S_1$-$S_3$ and $S_4$-$S_7$.

In operation, the control circuit 18 controls the voltage sources $V_1$-$V_3$ by sequentially switching one voltage source on for a specified duration while maintaining the other two voltage sources in their off state for that duration. As illustrated in FIG. 4C, for example, the control circuit 18 turns on $V_1$ for the specified duration while maintaining $V_2$ and $V_3$ in their off states, followed by turning off $V_1$ and turning on $V_2$ while maintaining $V_3$ in its off state for the specified duration, followed by turning off $V_2$ and turning on $V_3$ while maintaining $V_1$ in its off state for the specified duration. The control circuit 18 repeats the above process many times to cause ions having mobilities related to the voltage source switching frequency to drift through the various drift tube segments. It will be understood that the voltage applied by $V_1$ across the first drift tube segment, $S_1$, will be different than that applied by $V_1$ across remaining triplets of the drift tube segments, and that the voltage applied by $V_2$ across the first two drift tube segments, $S_1$-$S_2$, will also be different than that applied by $V_2$ across remaining triplets of the drift tube segments. Generally, the voltage applied by $V_1$ across the first drift tube segment, $S_1$, will be selected so as to establish an electric field, $E_1$, in the ion transmission region $d_t(1)$ that is identical to the electric field $E_1$ established by $V_1$ across various triplets of the remaining drift tube segments, $S_2$-$S_N$, and the voltage applied by $V_2$ across the first two drift tube segment, $S_1$-$S_2$, will be selected so as to establish an electric field, $E_2$, in the ion transmission region $d_t(1)$, ion elimination region $d_e(1)$ and ion transmission region $d_t(2)$ that is identical to the electric field $E_2$ established by $V_2$ across various triplets of the remaining drift tube segments, $S_3$-$S_N$.

The voltage gradient plot 70 of FIG. 4D illustrates an embodiment in which the arrangement of electric field activation sources includes four voltage sources, $V_1$, $V_2$, $V_3$ and $V_4$, each illustratively identical to the voltage sources $V_1$ and $V_2$ illustrated and described with respect to FIG. 2. In the embodiment of FIG. 4D, +$V_1$, +$V_2$, +$V_3$ and +$V_4$ are all electrically connected to the ion inlet gate $G_{I1}$ of the first drift tube segment, $S_1$. The +$V_1$ is further electrically connected to the ion inlet gates $G_{I2}$ and $G_{I6}$, of the drift tube segments $S_2$ and $S_6$ respectively, the +$V_2$ is further electrically connected to the ion inlet gates $G_{I3}$, and $G_{I7}$, of the drift tube segments $S_3$ and $S_7$ respectively, the +$V_3$ is further electrically connected to the ion inlet gates $G_{I4}$, and $G_{I8}$, of the drift tube segments $S_4$ and $S_8$ respectively, and the +$V_4$ is further electrically connected to the ion inlet gate $G_{I5}$ of the drift tube segment $S_5$. The −$V_1$ is electrically connected to the ion outlet gates $G_{O1}$ and $G_{O5}$, the −$V_2$ is electrically connected to the ion outlet gates $G_{O2}$ and $G_{O6}$, the −$V_3$ is electrically connected to the ion outlet gates $G_{O3}$ and $G_{O7}$, and the −$V_4$ is electrically connected to the ion outlet gates $G_{O4}$ and $G_{O8}$. In the four voltage source arrangement, the voltage sources $V_1$-$V_4$ are thus electrically connected, in alternating fashion, across four consecutive drift tube segments with all four voltage sources electrically connected to the ion inlet grid $G_{I1}$ of the first drift tube segment, $S_1$, and then with $V_1$ electrically connected across $S_1$, $S_2$-$S_5$, and $S_6$-$S_9$, with $V_2$ electrically connected across $S_1$-$S_2$ and $S_3$-$S_6$, with $V_3$ electrically connected across $S_1$-$S_3$ and $S_4$-$S_7$, and with $V_4$ electrically connected across $S_1$-$S_4$ and $S_5$-$S_8$.

In operation, the control circuit 18 controls the voltage sources $V_1$-$V_4$ by sequentially switching one voltage source on for a specified duration while maintaining the other three voltage sources in their off state for that duration. As illustrated in FIG. 4D, for example, the control circuit 18 turns on $V_1$ for the specified duration while maintaining $V_2$, $V_3$ and $V_4$ in their off states, followed by turning off $V_1$ and turning on $V_2$ while maintaining $V_3$ and $V_4$ in their off states for the specified duration, followed by turning off $V_2$ and turning on $V_3$ while maintaining $V_1$ and $V_4$ in their off states for the specified duration, followed by turning off $V_3$ and turning on $V_4$ while maintaining $V_1$ and $V_2$ in their off states for the specified duration. The control circuit 18 repeats the above process many times to cause ions having mobilities related to the voltage source switching frequency to drift through the various drift tube segments. It will be understood that the voltage applied by $V_1$ across the first drift tube segment, $S_1$, will be different than that applied by $V_1$ across remaining quadruplets of the drift tube segments, the voltage applied by $V_2$ across the first two drift tube segments, $S_1$-$S_2$, will be different than that applied by $V_2$ across remaining quadruplets of the drift tube segments, and the voltage applied by $V_3$ across the first three drift tube segments, $S_1$-$S_3$, will be different than that applied by $V_3$ across remaining quadruplets of the drift tube segments. Generally, the voltage applied by $V_1$ across the first drift tube segment, $S_1$, will be selected so as to establish an electric field, $E_1$, in the ion transmission region $d_t(1)$ that is identical to the electric field $E_1$ established by $V_1$ across various quadruplets of the remaining drift tube segments, $S_2$-$S_N$, the voltage applied by $V_2$ across the first two drift tube segment, $S_1$-$S_2$, will be selected so as to establish an electric field, $E_2$, in the ion transmission region $d_t(1)$, ion elimination region $d_e(1)$ and ion transmission region $d_t(2)$ that is identical to the electric field $E_2$ established by $V_2$ across various quadruplets of the remaining drift tube segments, $S_3$-$S_N$, and the voltage applied by $V_3$ across the first three drift tube segment, $S_1$-$S_3$, will be selected so as to establish an electric field, $E_3$, in the ion transmission regions $d_t(1)$, $d_t(2)$ and $d_t(3)$ and in the ion elimination regions $d_e(1)$ and $d_e(2)$ that is identical to the electric field $E_3$ established by $V_3$ across various quadruplets of the remaining drift tube segments, $S_4$-$S_N$.

The number of electric field activation sources, e.g., voltage sources, used in any particular embodiment, and the manner in which they are electrically connected to the various drift tube segments to operate as described above, is referred to as the phase (ϕ) of the ion mobility spectrometer 10. In the example of FIGS. 2, 3 and 4B in which two voltage sources $V_1$ and $V_2$ are used as described above, ϕ=2 as indicated in the plot 40 of FIG. 4B. In the example of FIG. 4C in which three voltage sources $V_1$, $V_2$ and $V_3$ are used as described above, ϕ=3 as indicated in the plot 60 of FIG. 4C. In the example of FIG. 4D in which four voltage sources $V_1$, $V_2$, $V_3$ and $V_4$ are used as described above, ϕ=4 as indicated in the plot 70 of FIG. 4D. It will be noted from FIG. 3 that in a ϕ=2 system, the fill rate of ions in the various drift tube segments $S_1$-$S_N$, i.e., the duty cycle of the ion mobility spectrometer 10, is 50%. It can be shown that in a ϕ=3 system, the duty cycle of the ion mobility spectrometer is 66.67% and in a ϕ=4 system, the duty cycle of the ion mobility spectrometer is 75%. A general expression for the duty cycle, d, of the ion mobility spectrometer 10 as a function of the phase, ϕ, is thus $d=1-(1/\phi)$.

Referring again to FIG. 3, the electric fields in the drift tube 14 in a two-phase (ϕ=2) ion mobility spectrometer 10 are established by two source $V_1$ and $V_2$. The electric fields established in the drift tube 14 by activation of $V_1$ include an electric drift field $E_1$, i.e., an electric field through which ions generated by the ion source drift toward the ion detector 16, in each of the drift tube segments, i.e., in each of the ion transmission regions $d_t$, and also in the even-numbered ion elimination regions, $d_e(2)$, $d_e(4)$, etc., and also includes a repulsive electric field, i.e., an electric field that repels and filters away ions traveling in the direction of the electric drift field, in odd-numbered ion elimination regions, $d_e(1)$, $d_e(3)$, $d_e(5)$, etc. Similarly, the electric fields established in the drift tube 14 by activation of $V_2$ includes an electric drift field $E_2$ in each of the drift tube segments and also in the odd-numbered ion elimination regions, $d_e(1)$, $d_e(3)$, $d_e(5)$, etc., and also includes a repulsive electric field in even-numbered ion elimination regions, $d_e(2)$, $d_e(4)$, etc.

It can be shown that in three-phase systems (ϕ=3) that include three electric field activation sources, $V_1$-$V_3$, such as that illustrated in FIG. 4C, activation of $V_1$ establishes a repulsive electric field in the first ion elimination region, $d_e(1)$, and in every following $3^{rd}$ ion elimination region, $d_e(4)$, $d_e(7)$, $d_e(10)$, etc., and also establishes an electric drift field, $E_1$, in all remaining ion elimination regions and in all of the drift tube segments $d_t$. Activation of $V_2$ likewise establishes a repulsive electric field in the second ion elimination region, $d_e(2)$, and in every following $3^{rd}$ ion elimination region, $d_e(5)$, $d_e(8)$, $d_e(11)$, etc., and also establishes an electric drift field, $E_2$, in all remaining ion elimination regions and in all of the drift tube segments $d_t$. Activation of $V_3$ similarly establishes a repulsive electric field in the third ion elimination region, $d_e(3)$, and in every following $3^{rd}$ ion elimination region, $d_e(6)$, $d_e(90)$, $d_e(12)$, etc., and also establishes an electric drift field, $E_3$, in all remaining ion elimination regions and in all of the drift tube segments $d_t$.

It can also be shown that in four-phase systems ($\phi=4$) that include four electric field activation sources, $V_1$-$V_4$, such as that illustrated in FIG. 4D, activation of $V_1$ establishes a repulsive electric field in the first ion elimination region, $d_e(1)$, and in every following $4^{th}$ ion elimination region, $d_e(5)$, $d_e(9)$, $d_e(13)$, etc., and also establishes an electric drift field, $E_1$, in all remaining ion elimination regions and in all of the drift tube segments $d_t$. Activation of $V_2$ likewise establishes a repulsive electric field in the second ion elimination region, $d_e(2)$, and in every following $4^{th}$ ion elimination region, $d_e(6)$, $d_e(10)$, $d_e(14)$, etc., and also establishes an electric drift field, $E_2$, in all remaining ion elimination regions and in all of the drift tube segments $d_t$. Activation of $V_3$ similarly establishes a repulsive electric field in the third ion elimination region, $d_e(3)$, and in every following $4^{th}$ ion elimination region, $d_e(7)$, $d_e(11)$, $d_e(15)$, etc., and also establishes an electric drift field, $E_3$, in all remaining ion elimination regions and in all of the drift tube segments $d_t$. Finally, activation of $V_4$ establishes a repulsive electric field in the fourth ion elimination region, $d_e(4)$, and in every following $4^{th}$ ion elimination region, $d_e(8)$, $d_e(12)$, $d_e(16)$, etc., and also establishes an electric drift field, $E_4$, in all remaining ion elimination regions and in all of the drift tube segments $d_t$.

From the foregoing examples, a generalized characterization can be made for an M-phase system, i.e., one that includes a number, M, of electric field activation sources, $V_1$-$V_M$. In such an M-phase system, the number, M, of electric field activation sources are each be operatively connected to one or more of the plurality of drift tube segments such that, when activated, each establishes a repulsive electric field in at least one of the first M ion elimination regions and in every following Mth ion elimination region, and also establishes an electric drift field in all remaining ion elimination regions and in all of the plurality of cascaded drift tube segments. In operation, the control circuit 18 sequentially activates each of the number, M, of electric field activation sources for a time duration while deactivating the remaining number, M, of electric field activation sources a number of times to thereby cause only ions generated by the ion source that have a predefined ion mobility or range of ion mobilities to traverse the drift tube 14.

Transmission of ions through the various drift tube segments $S_1$-$S_N$ as just described is only possible if the mobilities of the ions are in resonance with the switching rates of the electric fields applied by the electric field activation sources regardless of the phase of the spectrometer 10. In other words, to transmit ions sequentially through the various drift tube segments $S_1$-$S_N$ as just described, the ions must have mobilities that allow traversal exactly one drift tube segment in one field application duration. Ions with mobilities that are off resonance either traversing a drift tube segment too quickly or too slowly are eventually eliminated in one of the ion elimination regions $d_e$. The frequency at which the various electric field activation sources are switched on/off, i.e., the frequency at which the ions have resonant mobilities, is termed the fundamental frequency, $f_f$.

In the above description of the operation of the ion mobility spectrometer instrument 10, the control circuit 18 is described as being configured to control operation of the electric field activation sources $V_1$-$V_M$. Illustratively, the memory unit 20 has instructions stored therein that are executable by the control circuit 18 to control operation of the electric field activation sources $V_1$-$V_M$ in this manner.

In one alternative embodiment, each of the electric field activation sources $V_1$-$V_M$ may be programmable to produce, when triggered by an adjacent, e.g., lower-numbered, one of the electric field activation sources $V_1$-$V_M$, an electric field activation pulse of desired duration. In this embodiment, each higher-numbered one of the electric field activation sources $V_1$-$V_M$ may be programmable to be triggered for activation by deactivation of an adjacent lower-numbered one of the electric field activation sources $V_1$-$V_M$. Thus, deactivation of $V_1$ will trigger activation of $V_2$, deactivation of $V_2$ will trigger activation of $V_3$ (or $V_1$ again), and so forth. In this embodiment, the control circuit 18 is configured to control operation of the electric field activation sources $V_1$-$V_M$ only by activating the first one of the electric field activation sources $V_1$-$V_M$.

In another alternative embodiment, each of the electric field activation sources $V_1$-$V_M$ may be programmable to produce, when triggered by the control circuit 18, an electric field activation pulse having desired duration. In this embodiment, the control circuit 18 controls activation times of each of the electric field activation sources $V_1$-$V_M$, and once activated each of the electric field activation sources $V_1$-$V_M$ is operable to produce a pulse having time duration equal to a programmed pulse duration. In this embodiment, the control circuit 18 is configured to control operation of the electric field activation sources $V_1$-$V_M$ only by activating at specified times each of the electric field activation sources $V_1$-$V_M$.

It will be understood that while the electric field activation sources, $V_1$-$V_M$ were described as producing DC voltages of programmable duration this disclosure contemplates embodiments in which the electric field activation sources are configured to produce alternatively shaped electric field activation pulses. For example, such alternatively shaped electric field activation pulses may be linear or piece-wise linear pulse shapes, such as triangular or other linear or piece-wise linear shapes, or may be non-linear shapes such as sine-wave, Gaussian or other non-linear shapes. The corresponding electric fields applied in time-dependent fashion to the various segments $S_1$-$S_N$ of the drift tube 14 as described above may thus be linearly, piece-wise linearly or non-linearly varying. Alternatively still, different ones and/or blocks of the electric field activation sources $V_1$-$V_M$ may be activated for different durations. Those skilled in the art will recognize that, in general, any one or more of the segments $S_1$-$S_N$ may be operated for a duration that is different than the duration of operation of any one or more of the remaining ones of the segments $S_1$-$S_N$, and that operation of the ion mobility instrument 10 in this manner will result in a multi-dimensional ion mobility spectrometer instrument, i.e., a drift tube having one or more segments in any location relative to the ion inlet and ion outlet that is/are tuned to pass therethrough only ions having a mobility or range of mobilities that is/are different than that/those of one or more of the remaining segments.

Figure 5:
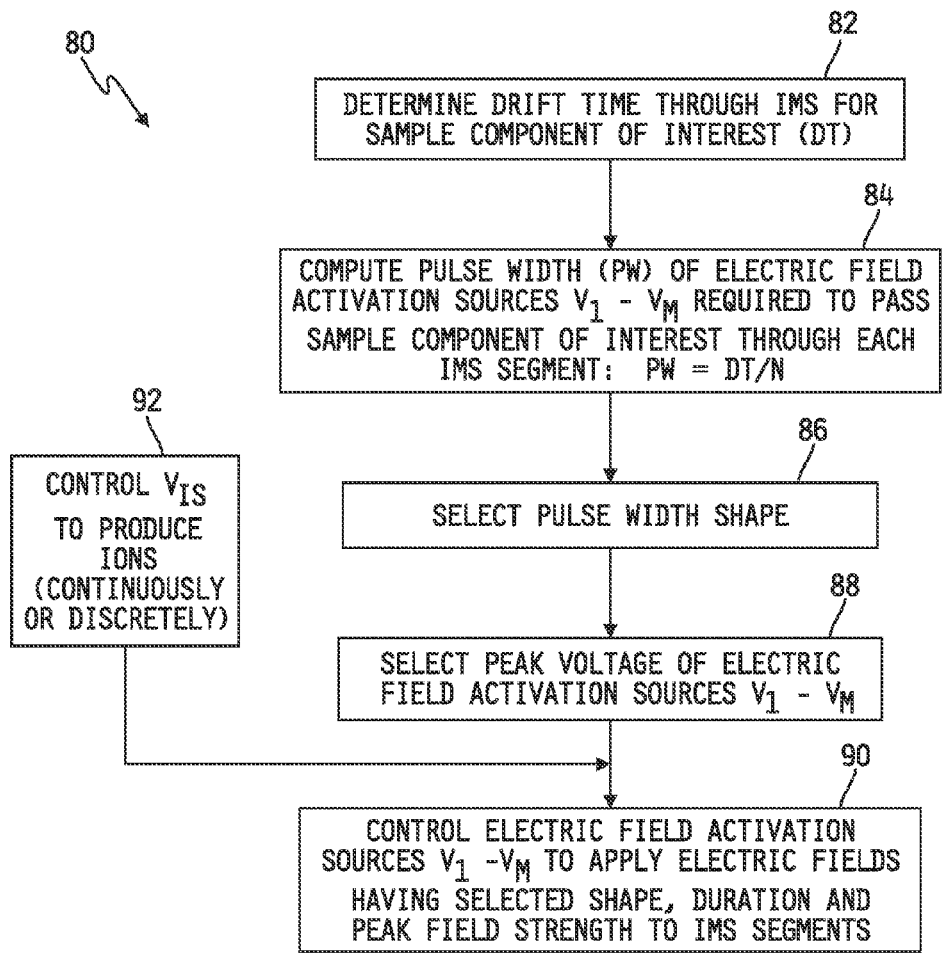
FIG. 5 is a flowchart of one illustrative process for operating the ion mobility spectrometer of either of FIG. 1 or 3 as an ion mobility filter operable to produce only ions having a selected mobility or range of mobilities from a continuous or discrete ion source.
Figure 6:
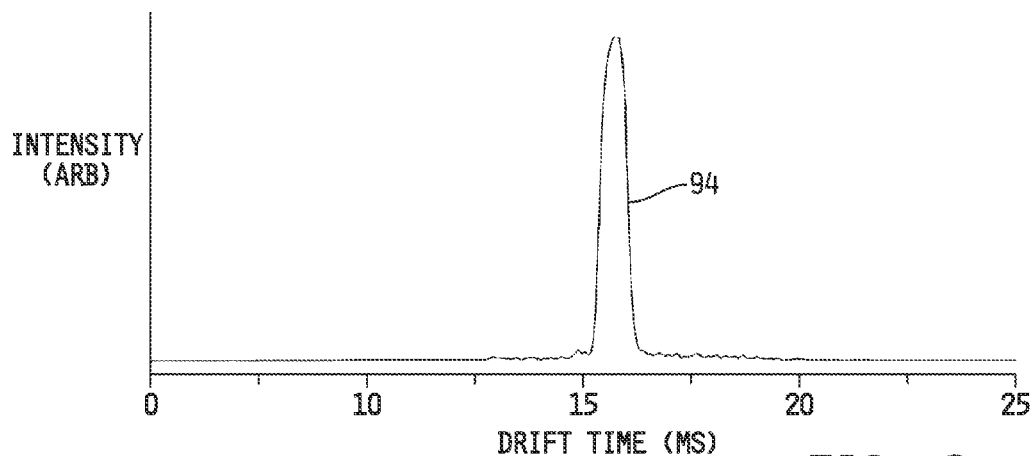
FIG. 6 is a plot of ion intensity vs. drift time illustrating the drift time of ions of the sodiated monomer $[M+Na]^+$ form of the simple oligosaccharide isomer raffinose through one particular embodiment of the ion mobility spectrometer of FIG. 1.

Referring now to FIG. 5, a flowchart is shown of one illustrative embodiment of a process 80 for operating the ion mobility spectrometer instrument 10 to act as an ion mobility filter by allowing travel through the drift tube 14 of only ions having a predefined mobility or range of mobilities as described hereinabove with respect to FIGS. 1-4D. The process 80 illustrated in FIG. 5 may be provided, in whole or in part, in the form of instructions that are stored in the memory unit 20 of the control circuit 18 and that are executable by the control circuit 18 to control the ion mobility spectrometer instrument 10 in accordance with the process 80. The process 80 begins at step 82 where the drift time, DT, through the drift tube 14 is determined for the sample component of interest. This may be done, for example, by first operating the ion drift tube 14 in a conventional manner to determine the drift time, DT, of the sample component of interest, although other conventional techniques may be used at step 82 to determine the drift time, DT, of the sample component of interest. For example, conventional ion mobility spectrometer configurations could be used to determine a drift time, or a drift time could be retrieved from literature, although in either case, instrument operating parameters used to determine such drift times, e.g., buffer gas pressure, operating temperature, drift tube length, etc., would have to be taken into account to determine corresponding operating parameters for those of the ion mobility spectrometer 10. Referring to FIG. 6, a plot 94 of ion intensity vs. drift time is shown illustrating the drift time of ions of the sodiated monomer [M+Na]$^+$ form of the simple oligosaccharide isomer raffinose through one particular embodiment of the ion mobility spectrometer 10. In this embodiment, the drift time, DT, of raffinose through the drift tube 14 is approximately 15.8 ms.

Following step 82, the pulse width, PW, of the number of electric field activation sources $V_1$-$V_M$ used in the ion mobility spectrometer instrument 10 is computed at step 84. The pulse width, PW, is the duration of the electric field that will be applied by each of the electric field activation sources $V_1$-$V_M$ to pass the sample component of interest, e.g., raffinose, through each segment. In order to pass the sample component of interest through a drift tube 14 having N segments, the pulse width, PW, must therefore satisfy the relationship PW=DT/N.

Following step 84, the shape of the pulse width is selected at step 86, and thereafter at step 88 the peak voltage of the electric field activation sources $V_1$-$V_M$ is selected. The process 80 advances from step 88 to step 90, and simultaneously with step 90 the ion source voltage supply, $V_{IS}$, is controlled at step 92 in a manner that causes the ion source 12 to produce ions. The ions produced at step 92 may be produced continuously or may instead be produced discretely as described hereinabove. In any case, the control circuit 18 is operable at step 90 to control the electric field activation sources $V_1$-$V_M$, as described hereinabove, to sequentially apply electric fields having the selected shape, duration and peak field strength to the various drift tube segments, $S_1$-$S_N$ as described hereinabove by example with reference to FIGS. 2-4D. Steps 90 and 92 may be repeated continuously or a finite number of times to thereby operate the ion mobility spectrometer instrument 10 as a continuous or discrete ion mobility filter. For the raffinose sample illustrated in FIG. 6, the pulse width, PW, of the electric field activation sources $V_1$-$V_M$ in the ion mobility spectrometer instrument 10 of FIG. 1, in which the drift tube 14 is constructed of 20 drift tube segments, $S_1$-$S_{20}$, and one ion focusing filter positioned approximately mid way between the ion inlet and ion outlet of the drift tube 14, is approximately 500 microseconds, which corresponds to an electric field activation source switching frequency of approximately 2.0 kHz. It will be understood that steps 82-88 are not required to be executed in the illustrated order, and that one or more of these steps may alternatively be interchanged with one or more other of these steps.

Figure 7:
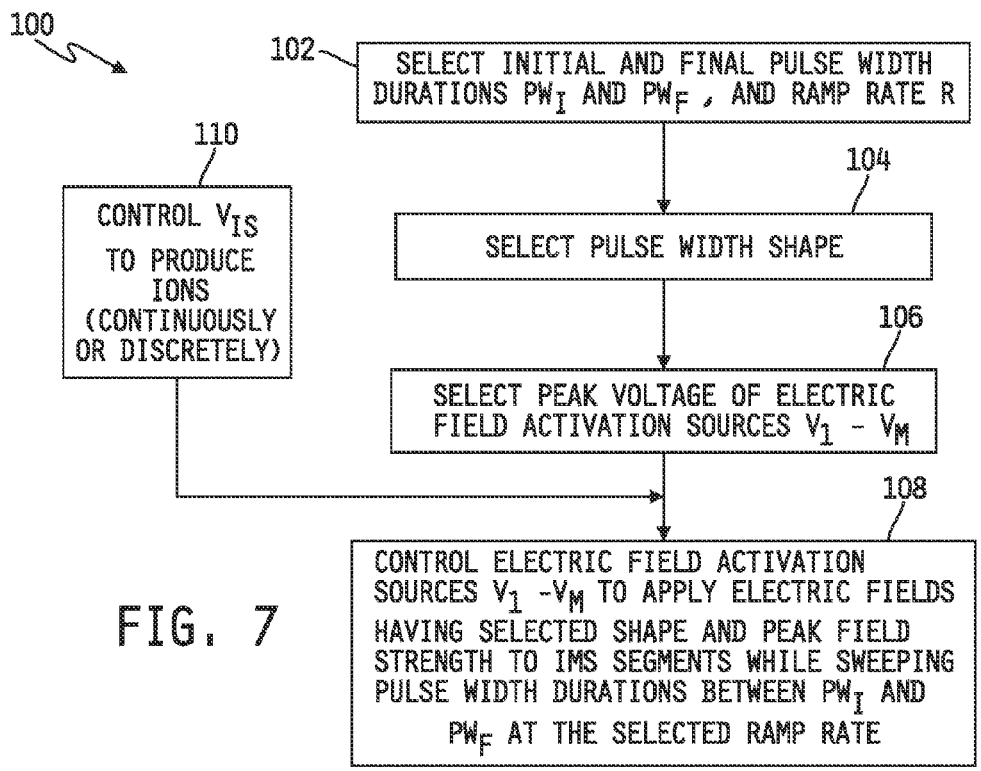
FIG. 7 is a flowchart of one illustrative process for operating the ion mobility spectrometer of either of FIG. 1 or 3 by sweeping the pulse widths of the electric field activation sources over a range of pulse width durations.

In addition to operation of the ion mobility spectrometer instrument 10 as an ion mobility filter as illustrated and described herein, the ion mobility spectrometer instrument 10 may also be operated in a manner that transmits ions at overtone frequencies of the fundamental frequency, $f_f$, as described briefly above. Referring to FIG. 7, for example, a flowchart of an illustrative process 100 for operating the ion mobility spectrometer 10 by sweeping the pulse widths, PW, of the electric field activation sources, $V_1$-$V_M$, over a range of pulse width durations. In addition to producing a fundamental ion intensity peak that corresponds to ion intensity peak resulting from the process 80 of FIG. 5, the process 100 further produces overtone ion intensity peaks that may be analyzed in the frequency domain to reveal additional characteristics of the sample component of interest. The process 100 illustrated in FIG. 7 may be provided, in whole or in part, in the form of instructions that are stored in the memory unit 20 of the control circuit 18 and that are executable by the control circuit 18 to control the ion mobility spectrometer instrument 10 in accordance with the process 100.

The process 100 begins at step 102 where initial and final pulse width durations, $PW_I$ and $PW_F$ respectively, and a ramp rate, R (or step size), are selected. Illustratively, the initial pulse width duration, $PW_I$, may be selected to be slightly longer than necessary to produce the fundamental ion intensity peak so that the resulting ion intensity vs. frequency spectrum begins approximately at the fundamental peak. Illustratively, the final pulse width duration, $PW_F$, may be selected to be a frequency beyond which no useful information is expected to occur, or beyond which no ion intensity information is sought. In any case, the ramp rate, R, and/or frequency step size between the initial and final pulse width durations, $PW_I$ and $PW_F$, will typically be selected to provide sufficient time at each pulse width duration to extract useful information from the ion mobility spectrometer instrument 10. Such information can be of the form of ion collision cross sections, $\Omega$, which can be derived from OMS measurements according to the following equation:

$$\Omega = \frac{(18\pi)^{1/2}}{16} \frac{ze}{(k_b T)^{1/2}} \left[\frac{1}{m_I} + \frac{1}{m_B}\right]^{1/2} \frac{E[\phi(h-1)+1]}{f(d_t + d_e)} \frac{760}{P} \frac{T}{273.2} \frac{1}{N},$$

where ze is ion charge, $k_b$ is Boltzmann's constant, P and T correspond to the buffer gas pressure and temperature respectively, N is the neutral number density, E is the electric field, f is the field application frequency, the quantity $\phi(h-1)+1$ is the harmonic number or overtone number, $m_I$ and $m_B$ correspond to the mass of the ion and the mass of the buffer gas, respectively, and all other variables have been defined herein.

Following step 102, the shape of the pulse width is selected at step 104, and thereafter at step 106 the peak voltage of the electric field activation sources $V_1$-$V_M$ is selected. The process 100 advances from step 106 to step 108, and simultaneously with step 108 the ion source voltage supply, $V_{IS}$, is controlled at step 110 in a manner that causes the ion source 12 to produce ions. The ions produced at step 110 may be produced continuously or may instead be produced discretely as described hereinabove, although if produced discretely a timing mechanism will typically be required to trigger new supplies of ions coincident with the changing of the pulse width durations. In any case, the control circuit 18 is operable at step 108 to control the electric field activation sources $V_1$-$V_M$, as described hereinabove, to apply electric fields having the selected shape and peak field strength to the drift tube segments, $S_1$-$S_N$ while sweeping the pulse width duration, PW, between $PW_I$ and $PW_F$ at the selected ramp rate and/or step size. It will be understood that steps 102-106 are not required to be executed in the illustrated order, and that one or more of these steps may alternatively be interchanged with one or more other of these steps.

While not specifically illustrated in FIG. 7 as a step in the process 100, ion detection signals produced by the ion detector 16 may be processed by the control circuit 18 and converted to the frequency domain in a conventional manner for further analysis and/or observation. For the raffinose sample illustrated in FIG. 6, for example, sweeping the pulse width, PW, of the electric field activation sources $V_1$-$V_4$ in the ion mobility spectrometer instrument 10 of FIG. 1 between approximately 10 milliseconds down to approximately 22 micro-seconds yields the ion intensity vs. frequency spectrum 112 illustrated in FIG. 8. Illustratively, the 3$^{rd}$ overtone produces the most highly resolved ion intensity peak.

Figure 8:
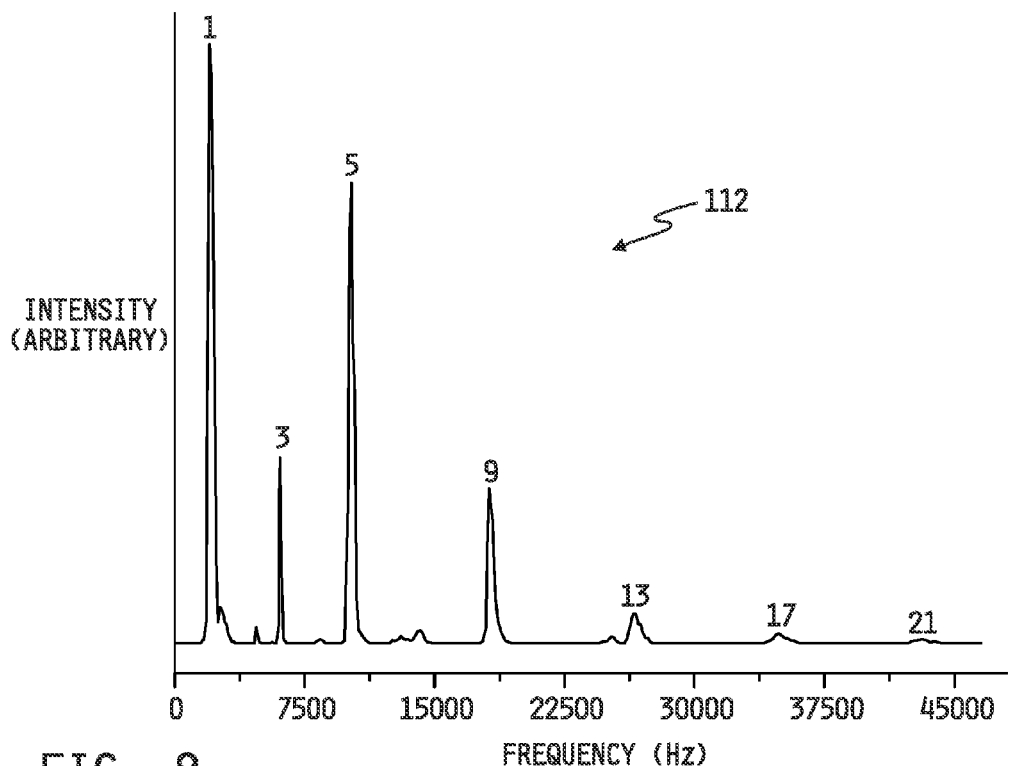
FIG. 8 is a plot of ion intensity vs. frequency illustrating the result in the frequency domain of the process of FIG. 7 using a continuous source of raffinose ions.
Figure 9:
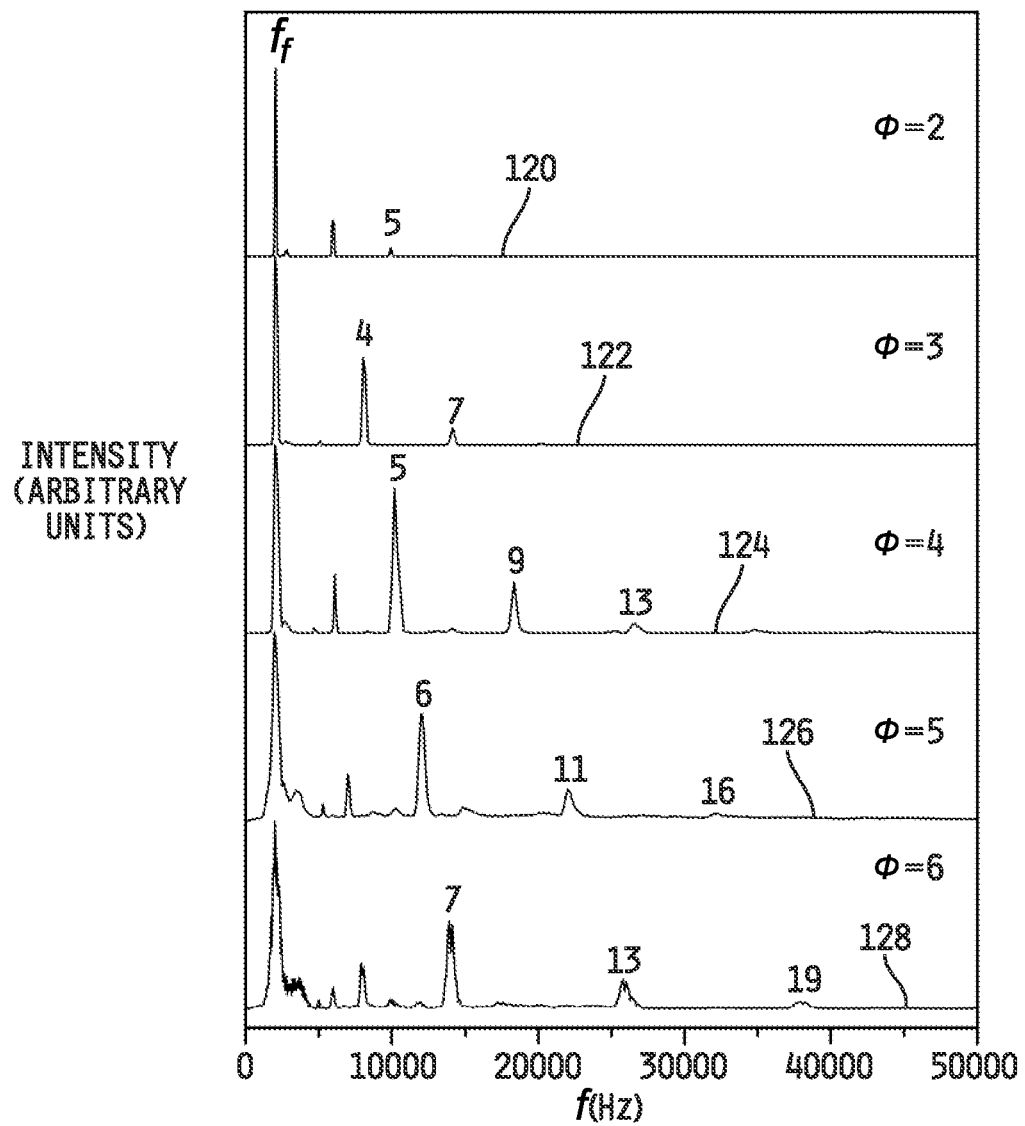
FIG. 9 includes a number of plots of ion intensity vs. frequency illustrating results in the frequency domain of the process of FIG. 7 applied to ion mobility instruments having different phase numbers.

Generally, the overtones produced by frequency sweeps of the type illustrated in FIG. 8 will be defined, at least in part, by the phase ($\phi$) of the ion mobility spectrometer 100. Referring to FIG. 9, for example, a number of plots 120, 122, 124, 126 and 128 are shown of frequency spectrums of raffinose in which the phase, $\phi$, of the ion mobility spectrometer 10 correspondingly increases. In all cases, the electric field activation sources, $V_1$-$V_M$ were configured to operate as described hereinabove with respect to FIGS. 2-4D. In the plot 120, $\phi$=2, and the associated frequency spectrum includes an ion peak at the fundamental frequency, $f_f$, and additional peaks at the third and fifth overtones. In the plot 122, $\phi$=3, and the associated frequency spectrum includes an ion peak at the fundamental frequency, $f_f$, and additional peaks at the fourth and seventh overtones. In the plots 124, 126 and 128, $\phi$=4, 5 and 6 respectively. The frequency spectrum 124 includes an ion peak at the fundamental frequency, $f_f$, and additional peaks at the fifth, ninth and thirteenth overtones, the frequency spectrum 126 includes an ion peak at the fundamental frequency, $f_f$, and additional peaks at the sixth, eleventh and sixteenth overtones, and the frequency spectrum 128 includes an ion peak at the fundamental frequency, $f_f$, and additional peaks at the seventh, thirteenth and nineteenth overtones. It should be noted that as the phase of the ion mobility spectrometer 10 is increased, secondary overtones increasing appear between the fundamental peak, $f_f$, and the first expected overtone. These secondary overtones correspond to intermediate harmonic frequencies, i.e., those between the overtone frequencies, and may carry additional ion information.

Generally, the overtones that should be expected to be observed in embodiments of the ion mobility spectrometer 10 operated with uniform, constant electric fields in the various drift tube segments, $S_1$-$S_N$ as described hereinabove, are given by the equation H=$\phi$(h−1)+1, h=1, 2, 3, . . . , where H is a harmonic number, $\phi$ is the phase of the ion mobility spectrometer 10, and h is an integer. Thus, for $\phi$=2, H=1, 3, 5, 7, . . . , for $\phi$=3, H=1, 4, 7, 10, . . . , for $\phi$=4, H=1, 5, 9, 13, . . . , for (1)=5, H=1, 6, 11, 16, . . . , and for $\phi$=6, H=1, 7, 13, 19, . . . , etc.

Figure 10:
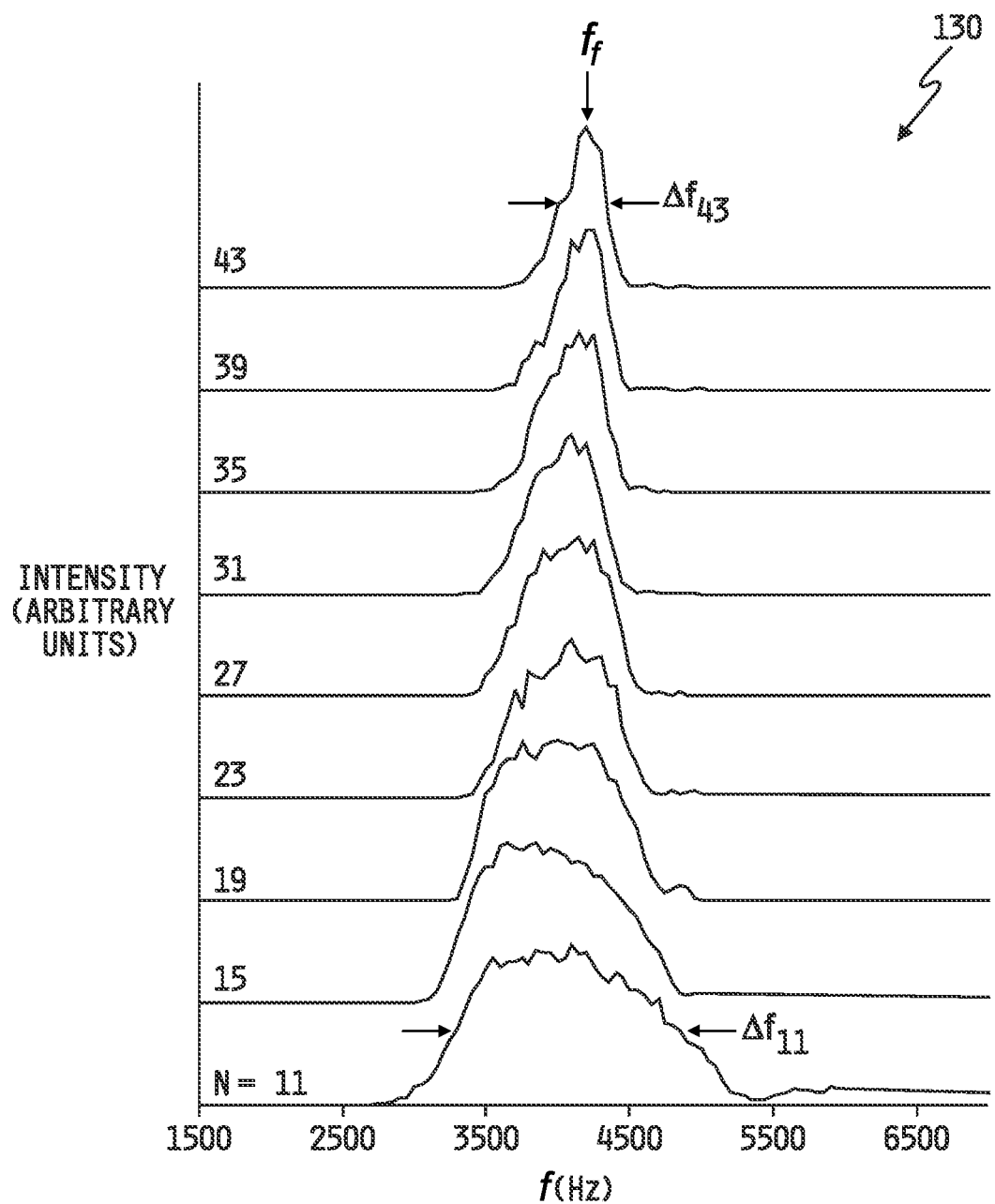
FIG. 10 includes a number of plots of ion intensity vs. frequency illustrating results in the frequency domain of the process of FIG. 5 applied to ion mobility instruments having different numbers of drift tube sections.

The resolving power, R, of the ion mobility spectrometer instrument 10 is defined by the equation $R_{OMS}$=f/$\Delta$f, where f is the frequency at which maximum ion intensity of transmitted and $\Delta$f is the width of the peak at half maximum. Generally, it is observed that the resolving power, R, of the ion mobility spectrometer instrument 10 increases with increasing overtone number, H. The resolving power, R, of the ion mobility spectrometer instrument 10 is also influenced by the total number, N, of drift tube segments, $S_1$-$S_N$, used. Referring to FIG. 10, for example, a number of plots 130 are shown illustrating the shapes of fundamental-frequency, ion intensity peaks for a four-phase ($\phi$=4) ion mobility spectrometer instrument 10 in which the total number of drift tube segments, N, is varied between 11 and 43 as indicated on the left portion of FIG. 10. The plots 130 were generated from a sample of the sodiated monomer [M+Na]$^+$ form of the simple oligosaccharide isomer melezitose using the ion mobility instrument 10 illustrated and described herein. As illustrated in FIG. 10, whereas the peak intensities do not change significantly, the widths, $\Delta$f, of the peaks at half maximum decrease as N increases. For example, $\Delta f_{11}$, corresponding to the width of the N=11 peak at half maximum, is approximately 1600 Hz, whereas $\Delta f_{43}$, corresponding to the width of the N=43 peak at half maximum, is approximately 345 Hz. The ratio f/$\Delta$f, and thus, $R_{OMS}$, accordingly increases as the number, N, of drift tube segments $S_1$-$S_N$ increases.

In a conventional ion mobility spectrometer; that is to say, an ion mobility spectrometer in which a single electric field is applied across the length of the drift tube, the resolving power is generally understood to follow the relationship $R_{IMS}$=SQRT[(E*e*L)/(16*$k_b$*T*ln2)], where E is the applied electric field, e is the elementary charge value, L is the length of the drift tube, $k_b$ is Boltzmann's constant, and T is the temperature of the drift tube.

In the ion mobility instruments 10 illustrated and described herein, the overall resolving power, $R_{OMS}$, is a function of $R_{IMS}$ and is also a function of the total number, n, of drift tube segments, $S_1$-$S_N$, the phase number, $\phi$, of the applied electric field and the harmonic number, m. Illustratively, $R_{OMS}$ is given by the equations:

$$R_{OMS} = \frac{1}{1 - \left[1 - \frac{C}{R_{IMS}}\right]\left[\frac{mn - \left[\phi - 1 - \frac{l_e}{l_t + l_e}\right]}{mn}\right]} \text{ or}$$

$$R_{OMS} = \frac{1}{\frac{C}{R_{IMS}}\left[1 - \frac{\phi - 1 - \frac{l_e}{l_t + l_e}}{mn}\right] + \frac{\phi - 1 - \frac{l_e}{l_t + l_e}}{mn}}$$

where C is a constant and all other variables have been defined herein. It should be noted that the resolving power, $R_{OMS}$, generally increases with increasing n and also with increasing m, and the resolving power, $R_{OMS}$, decreases with increasing $\phi$. It should also be noted that in the limit of high $R_{IMS}$, the first term in the denominator of the foregoing equation approaches zero and the foregoing equation reduces to $R_{OMS}$=m*n/[$\phi$−1−$I_e$/($I_t$+$I_e$)].

It can further be shown that the resolving power of any peak in an OMS distribution can obtained by replacing the harmonic number, m, in the above equation with ($\phi$q+1), and then by multiplying the entire equation by the quantity ($\phi$/k+1), where k is an overtone series index having limits of 0 to $\phi$−1, and q is an overtone peak index having limits of 0 to infinity.

Figure 11:
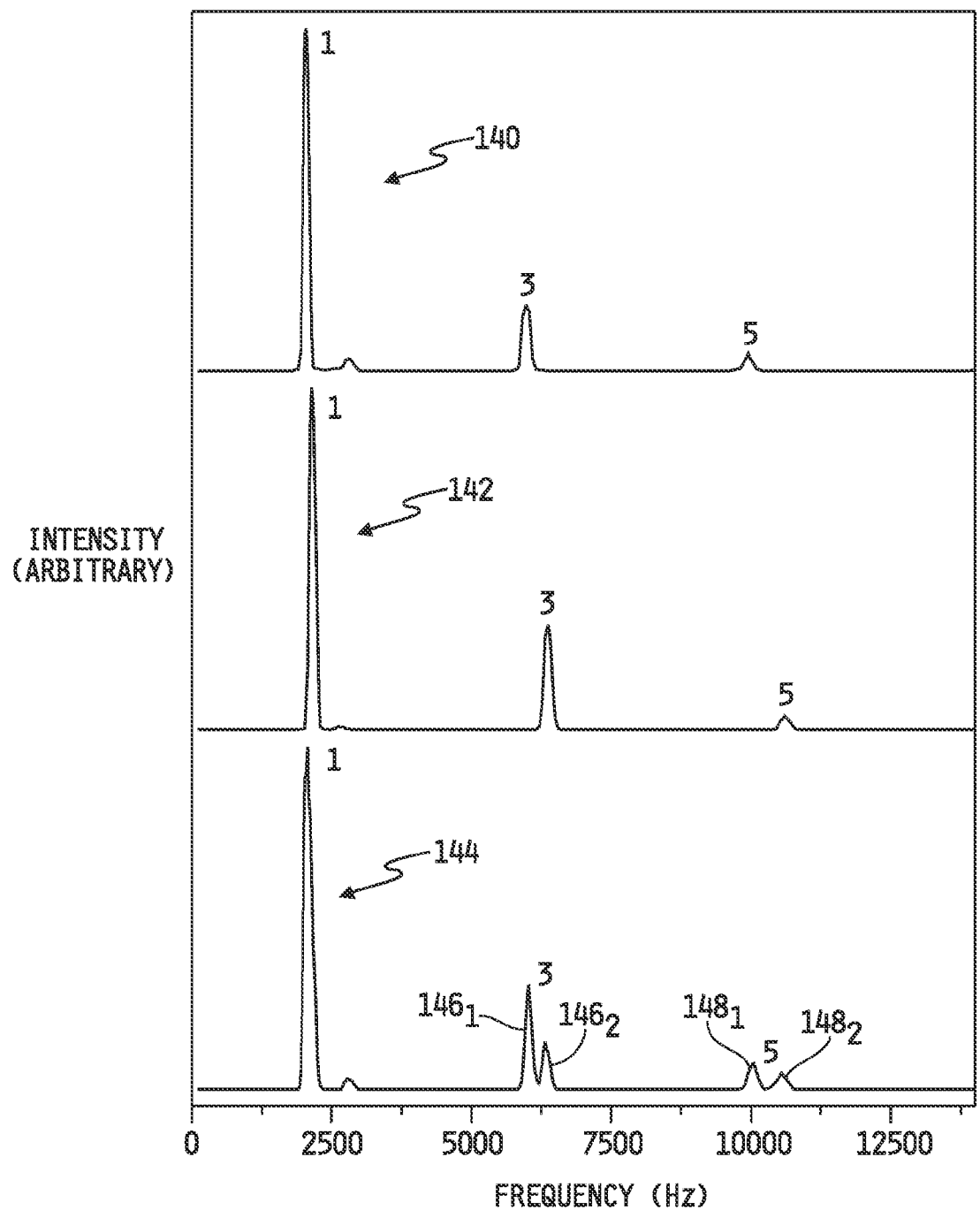
FIG. 11 includes a number of plots of ion intensity vs. frequency illustrating results in the frequency domain of the process of FIG. 7 applied to a raffinose sample, a melezitose sample and to a sample mixture of raffinose and melezitose.

Referring now to FIG. 11, plots of ion intensity vs. frequency are shown to illustrate one implementation of the enhanced resolving power of the ion mobility spectrometer 10 at overtone frequencies. The plots of FIG. 11 are frequency-domain plots that were generated with a two-phase ($\phi$=2) configuration of the ion mobility instrument 10. In the plots of FIG. 11, only the overtone peaks 3 and 5 are shown along with the peak at the fundamental frequency, 1. The plot 140 represents a frequency-domain plot of raffinose, the plot 142 represents a frequency-domain plot of the sodiated monomer [M+Na]$^+$ form of the simple oligosaccharide isomer melezitose, and the plot 144 represents a frequency-domain plot of a 3:1 raffinose:melezitose mixture. The frequency spectrum of the plot 144 illustrates that whereas the raffinose and melezitose are indistinguishable at the fundamental frequency, they are partially resolved at the third overtone, 146$_1$ and 146$_2$, and are fully resolved at the fifth overtone, 148$_1$ and 148$_2$. The harmonic/overtone analysis described in this disclosure, e.g., the pulse width duration sweeping process 100 illustrated in FIG. 7, may therefore be used to accurately identify a sample component of interest, and/or to distinguish a sample component of interest from another sample component.

Figure 12A:
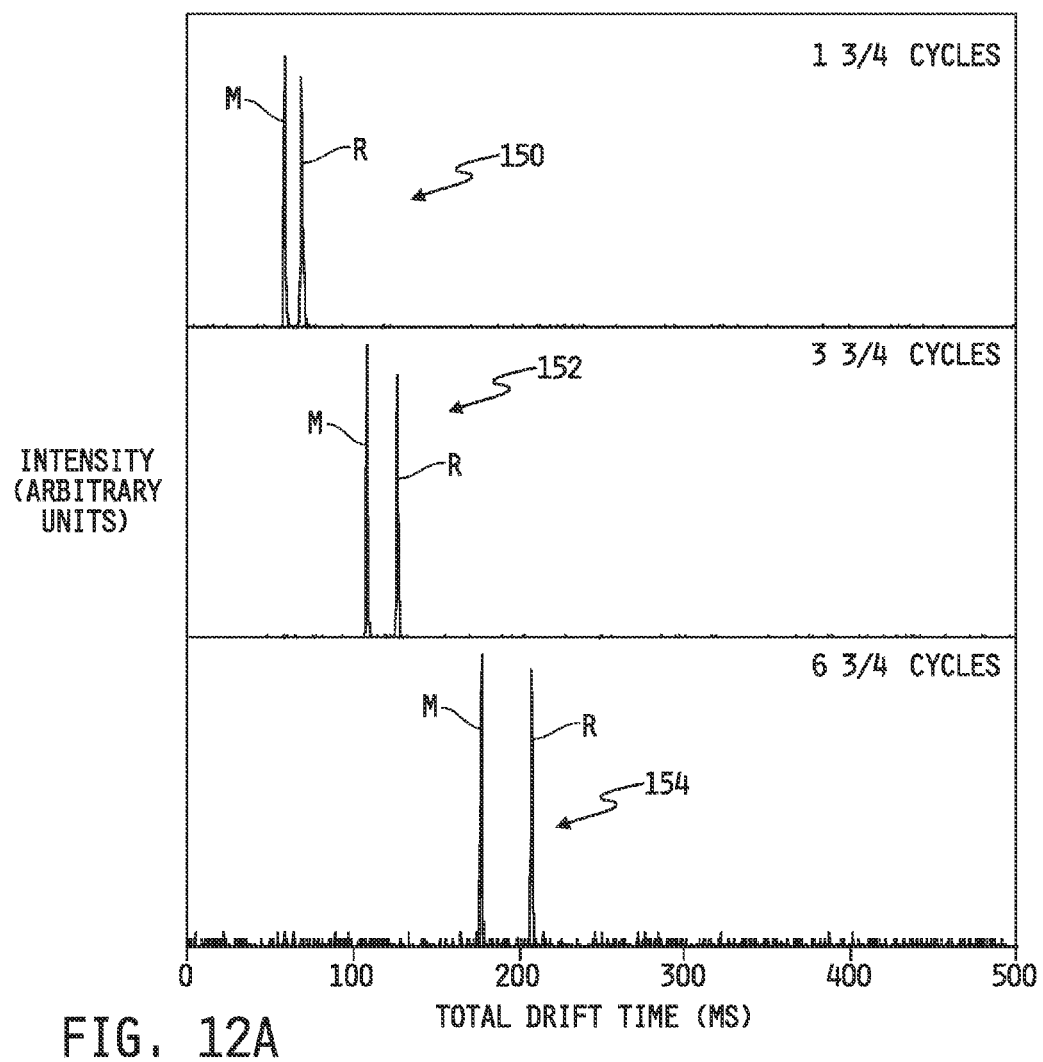
FIG. 12A includes a number of plots of ion intensity vs. total drift time illustrating results in the time domain of the process of FIG. 5 applied to a raffinose/melezitose mixture using a cyclotron geometry ion mobility spectrometer.

The raffinose and melezitose mixture can alternatively be resolved at or near their fundamental frequencies if allowed to drift along a sufficiently long drift distance. This may be accomplished, for example, by employing the ion mobility spectrometer operating technique illustrated in FIG. 5 in an ion mobility spectrometer having a circular or so-called cyclotron geometry, as illustrated and described in co-pending PCT Publication No. WO 2008/028159 A2, filed Aug. 1, 2007, the disclosure of which has been incorporated herein by reference. Referring now to FIG. 12A, plots 150, 152 and 154 are shown of such an experiment in which raffinose and melezitose were separated in a circular or cyclotron geometry ion mobility spectrometer 160 having a cyclotron portion constructed such that the drift tube, made up of cascaded ion transmission sections ($d_t$) and ion elimination sections ($d_e$) as illustrated and described hereinabove with respect to FIGS. 2-4, defines a closed and continuous ion travel path.

Figure 12B:
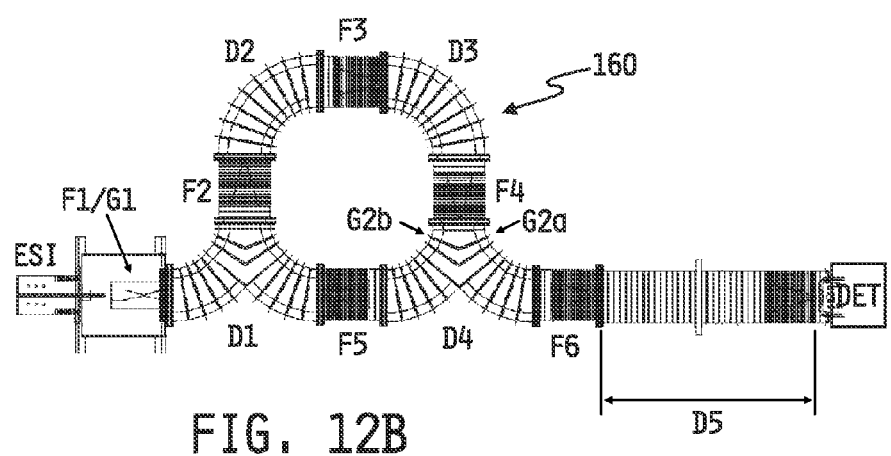
FIG. 12B is a diagram of one illustrative embodiment of a cyclotron geometry ion mobility spectrometer used to generate the plots of FIG. 12A.

Referring to FIG. 12B, one illustrative embodiment of such a cyclotron ion mobility spectrometer 160 is shown. In the illustrated embodiment, the drift tube is made up of four conventional ion funnels, F2-F5 joined at each end by curved drift tube segments D1-D4. Two of the curved drift tube segments D1 and D4 have Y-shaped geometries. In addition to forming one drift tube segment of the cyclotron portion of the drift tube, the segment D1 selectively direct ions generated by an ion source, e.g., an electrospray ion source, ESI, coupled to D1 via a funnel/gate arrangement, F1/G1, into the cyclotron portion via an ion entrance drift tube section. In addition to forming another drift tube segment of the cyclotron portion of the drift tube, the segment D4 selectively directs ions via an ion exit drift tube segment from the cyclotron portion and through a cascaded funnel, F6, and drift tube segment, D5 to an ion detector, DET. It will be understood that the embodiment of the cyclotron ion mobility spectrometer 160 shown in FIG. 12B is merely illustrative, and that the cyclotron portion of the spectrometer 160 may alternatively include more or fewer drift tube segments than the eight segments (D1-D4 and F2-F5) shown. It will further be understood that while the ion entrance drift tube segment is shown coupled between the ion source (ESI-F1/G1) and the drift tube segment D1, it may alternatively be coupled to a different one of the drift tube segments. Likewise, while the ion exit drift tube segment is shown coupled between the drift tube segment D4 and the funnel segment F6, it may alternatively be coupled to a different one of the drift tube segments. Moreover, while the ion entrance and exit drift tube segments are shown coupled to different ones of the drift tube segments, they may alternatively be coupled to a common one of the drift tube segments such that ions are admitted to and extracted from the same drift tube segment. It will further be understood that more or fewer drift tube segments and/or ion funnels may be positioned between the ion outlet of the ion exit drift tube segment of D4 and the ion detector, DET. In one embodiment, for example, the ion detector, DET, may be coupled directly to the ion outlet of the ion exit drift tube segment of D4, and in other embodiments any number of drift tube segments and/or ion funnels may be positioned between the ion exit drift tube segment of D4 and the ion detector, DET. In any case, the ion detector, DET, may be conventional and is configured to detect ions exiting the ion drift tube segment portion of D4 and produce corresponding ion detection signals. The memory of the control circuit illustratively includes instructions stored therein that are executable by the control circuit to process the ion detection signals in a conventional manner to determine ion mobility spectral information therefrom.

Although not specifically shown in FIG. 12B for ease of illustration and understanding, it will be understood that a number, M, of electric field activation sources are connected to the various drift tube sections of the cyclotron ion mobility spectrometer 160, a voltage source, $V_{IS}$, is connected to the ion source (ESI-F1/G1), a source of buffer gas is fluidly coupled to the drift tube, and a control circuit is electrically connected to one or more of the M electric field activation sources, voltage source, $V_{IS}$ and ion detector, all as illustrated and described herein with respect to FIGS. 1-4. The control circuit, as described hereinabove, illustratively includes a memory having instructions stored therein that are executable by the control circuit to control operation of the cyclotron ion mobility spectrometer 160. The various voltage sources and control circuitry, as illustrated and described above, are thus omitted from FIG. 12B for brevity. The number, M, may be any positive integer greater than 2, and general operation of the number, M, of electric field activation sources is illustrated and described herein with respect to FIGS. 1-4.

The ion source is illustrated in FIG. 12B as an electrospray ion source fluidly coupled to an ion funnel/gate, F1/G1, although the ion source may alternatively be or include any conventional ion source that may be controlled, via the voltage source, $V_{IS}$, by the control circuit according to instructions stored in the memory that are executable by the control circuit to selectively produce ions in a single, e.g., one-shot, periodic, e.g., pulsed, and/or continuous fashion as is known in the art. The ion gate, G1, of the ion source is illustratively positioned at an ion inlet of the ion entrance drift tube segment of D1 such that the ion source is coupled to the inlet of the ion entrance drift tube segment of D1, and an ion outlet of the ion entrance drift tube segment of D1 is coupled to the cyclotron portion of D1. The ion exit drift tube segment of D4 likewise has an ion inlet that is coupled to the cyclotron portion of D4, and an ion outlet coupled to the inlet of the ion funnel F6.

The drift tube of the cyclotron ion mobility spectrometer 160 illustrated in FIG. 12B is, like the embodiments illustrated in FIGS. 1-4, partitioned into multiple cascaded drift tube segments D1-D4 and F2-F5. In one embodiment, each of the drift tube segments D1-D4 and F2-F5 has an ion inlet at one end and an ion outlet at an opposite end, and an ion elimination region is defined between the ion outlet and the ion inlet of each adjacent drift tube segment as illustrated and described hereinabove with respect to FIGS. 1-4. The ion outlet of a last one of the drift tube segments, e.g., F5, is coupled to the ion inlet of the first one of the drift tube segments, e.g., D1, such that the drift tube defines therein a closed and continuous ion travel path which, in the illustrated embodiment, extends clockwise within D1-D4 and F2-F5. Illustratively, as just described, the ion elimination regions may be defined between the ion outlets and ion inlets of each of the drift tube segments D1-D4 and F2-F5, such as illustrated in FIG. 2, and in this embodiment, each of D1-D4 and F2-F5 is an ion transmission section, $d_t$, and the ion elimination regions, $d_e$, are defined between adjacent ones of D1-D4 and F2-F5. In alternative embodiments, the lengths of the funnel sections F2-F5 may be made shorter than the lengths of the drift tube sections D1-D4, and in this embodiment, the drift tube sections D1-D4 are the ion transmission sections, $d_t$, and the funnel sections F2-F5 are the ion elimination sections, $d_e$. In other alternative embodiments, the lengths of the drift tube sections D1-D4 may be made shorter than the lengths of the funnel sections F2-F5, and in this embodiment the funnel sections F2-F5 are the ion transmission sections, $d_t$, and the drift tube sections D1-D4 are the ion elimination sections.

An ion gate arrangement is positioned within the drift tube segment D4, and is configured to control ion travel through the cyclotron and ion exit drift tube portions of D4. The ion gate arrangement is generally responsive to one set of one or more ion gate signals produced by the control circuit to direct ions moving through the drift tubes D1-D3 and F2-F5 through the cyclotron drift tube portion of D4 such that the ions may continue to travel around the cyclotron portion of the spectrometer 160 defined by D1-D4 and F2-F5 while also blocking the ions from entering the ion exit drift tube segment portion of D4 such that ions moving through the cyclotron drift tube segment portion of D4 cannot advance to the ion detector, DET. The ion gate arrangement is also generally responsive to another set of the one or more ion gate signals produced by the control circuit to direct ions moving through the drift tubes D1-D3 and F2-F5 through the ion exit drift tube segment portion of D4 while also blocking ions from moving completely through the drift tube segment portion of D4 such that the ions travelling around the cyclotron portion of the spectrometer 160 defined by D1-D4 and F2-F5 do not advance completely through the drift tube segment portion of D4 and instead advance through the ion exit drift tube segment portion of D4 to the ion detector, DET. The ion gate arrangement is thus responsive to the one set of one or more ion gate signals to direct ions traveling through the cyclotron portion of the spectrometer 160 to the next drift tube section, e.g., F5, in the cyclotron portion of the spectrometer 160, and to the other set of one or more ion gate signals to extract the ions traveling through the cyclotron portion of the spectrometer 160 by directing the ions through the ion exit drift tube section of D4 toward the ion detector, DET. Illustratively, the ion mobility spectrometer 160 includes one or more additional voltage sources electrically connected to the ion gate arrangement, and the control circuit is thus generally operable to control the ion gate arrangement to direct ions moving through, and or blocking ions from moving through, the ion gate arrangement by controlling operation of such voltage sources in a conventional manner. The one or more additional voltage sources may be conventional voltage sources included within, or in addition to, the number, M, of electric field activation sources. Illustratively, the memory of the control circuit has instructions stored therein that are executable by the control circuit to control operation of the ion gate arrangement just described by controlling operation of the one or more additional voltage sources.

In the embodiment illustrated in FIG. 12B, the ion gate arrangement just described is implemented in the form of two separate ion gates; G2a positioned in, or at the ion inlet of, the ion exit drift tube segment portion of D4, and G2b positioned in the cyclotron drift tube segment portion of D4. In this embodiment, the one set of the one or more ion gate signals described above may include a first ion gate signal to which the ion gate G2b is responsive to allow ions to pass therethrough and a second ion gate signal to which the ion gate G2a is responsive to block ions from passing therethrough, and the other set of the one or more ion gate signals described above may include a third ion gate signal to which the ion gate G2b is responsive to block ions from passing therethrough and a fourth ion gate signal to which the ion gate G2a is responsive to allow ions to pass therethrough. Those skilled in the art will recognize that the ion gate arrangement may include more or fewer ion gates variously positioned relative to D4 and controllable by the control circuit or other electronic controller to direct ions through the cyclotron drift tube segment portion of D4 while blocking ions from entering the ion exit drift tube segment portion of D4, and to alternatively direct ions through the ion exit drift tube segment portion of D4 while blocking ions from traveling completely through the cyclotron drift tube segment portion of D4.

In the embodiment illustrated in FIG. 12B, ions are introduced into the cyclotron portion (e.g., D1-D4 and F2-F5) of the spectrometer 160 via control of the gate, G1, such that ions enter the cyclotron portion via the ion entrance drift tube segment portion of D1. With the ion gates G2a and G2b set that G2b allows ions to pass therethrough and G2a blocks ions from passing therethrough, ions are then directed around the cyclotron portion of the spectrometer 160 via sequential pulses applied by the number, M, of electric field activation sources to the various cyclotron sections D1-D4 and F2-F5 which create sequential electric fields in the cyclotron sections D1-D4 and F2-F5 at a desired frequency or pulse rate as described hereinabove with respect to FIG. 5 to thereby cause only ions supplied by the ion source that have a predefined ion mobility or range of ion mobilities defined by the frequency or pulse rate to travel through the cyclotron portion of the spectrometer 160. Ions may be so directed around the cyclotron portion of the spectrometer 160 any number of times, and can then be extracted from the cyclotron portion of the spectrometer 160 by controlling the ion gate G2b to block ions from passing therethrough and controlling the ion gate G2a to allow ions to pass therethrough to the ion detector, DET. The number, M, of electric field activation sources may include two or more sources as illustrated and described hereinabove with respect to FIGS. 1-4, and the electric fields created within the various drift tube segments D1-D4 and F2-F5 of the cyclotron portion of the spectrometer 160 by the number, M, of The electric field activation sources may be constant, linear, non-linear or have any desired shape or profile, also as described hereinabove. Illustratively, the electric fields created in F6 and D5 when extracting ions from the cyclotron portion of the spectrometer 160 are constant, although these fields may alternatively also be linear, non-linear or have any desired shape or profile.

Illustratively, the memory of the control circuit has instructions stored therein that are executable by the control circuit to control the ion source voltage source, $V_{IS}$, to produce ions, to control the ion gate arrangement to direct ions around the cyclotron portion of the spectrometer 160 while blocking ions from the ion detector, and to sequentially activate the number, M, of electric field activation sources for a predefined time duration while deactivating the remaining number, M, of electric field activation sources to thereby cause only ions supplied by the ion source that have a predefined ion mobility or range of ion mobilities defined by the predefined time duration, e.g., the activation frequency or pulse rate of the number, M, of electric field activation sources, to travel through the cyclotron portion of the spectrometer 160 and, after the ions have traveled around the cyclotron portion of the spectrometer 160 a selected number of times, to control the ion gate arrangement to draw ions moving through the cyclotron portion of the spectrometer 160 into the ion exit drift tube segment and toward the ion detector. As described hereinabove, the mobility or range of mobilities of ions resulting from operation of the spectrometer 160 as just described is/are resonant with a fundamental frequency, $f_f$, of operation of the electric field activation sources, $V_1$-$V_M$. Alternatively or additionally, as described hereinabove with respect to FIGS. 7-9, the instructions stored in the memory of the control circuit may include instructions that are executable by the control circuit to conduct OMS analysis, as this term has been defined hereinabove, by controlling the ion source voltage source, $V_{IS}$, and the number, M, of electric field activation sources to sweep the activation frequency or pulse rate of the number, M, of electric field activation sources over a predefined set of activation frequencies or pulse rates to thereby cause ions within the drift tube that have ion mobilities resonant with one or more overtones, e.g., harmonic frequencies, of operation of the electric field activation sources, $V_1$-$V_M$, and/or that have ion mobilities resonant with fundamental frequencies of the activation frequencies or pulse rates, i.e., activation times, of the electric field activation sources, $V_1$-$V_M$, for each of the discrete activation frequencies or pulse rates over the predefined set of activation frequencies or pulse rates, to travel through the spectrometer 160.

Referring again to FIG. 12a, the plot 150 represents the raffinose, R, and melezitose, M, ion peaks after 1¾ cycles of ion travel through the cyclotron portion of the instrument 160. The plot 152 similarly represents the raffinose, R, and melezitose, M, ion peaks after 3¾ cycles, and the plot 154 represents the raffinose, R, and melezitose, M, ion peaks after 6¾ cycles. While 1¾ cycles is sufficient to isolate each of the raffinose and melezitose ions, it is evident from FIG. 12a that the two ion peaks separate further as the number of cycles increases.

Figure 14:
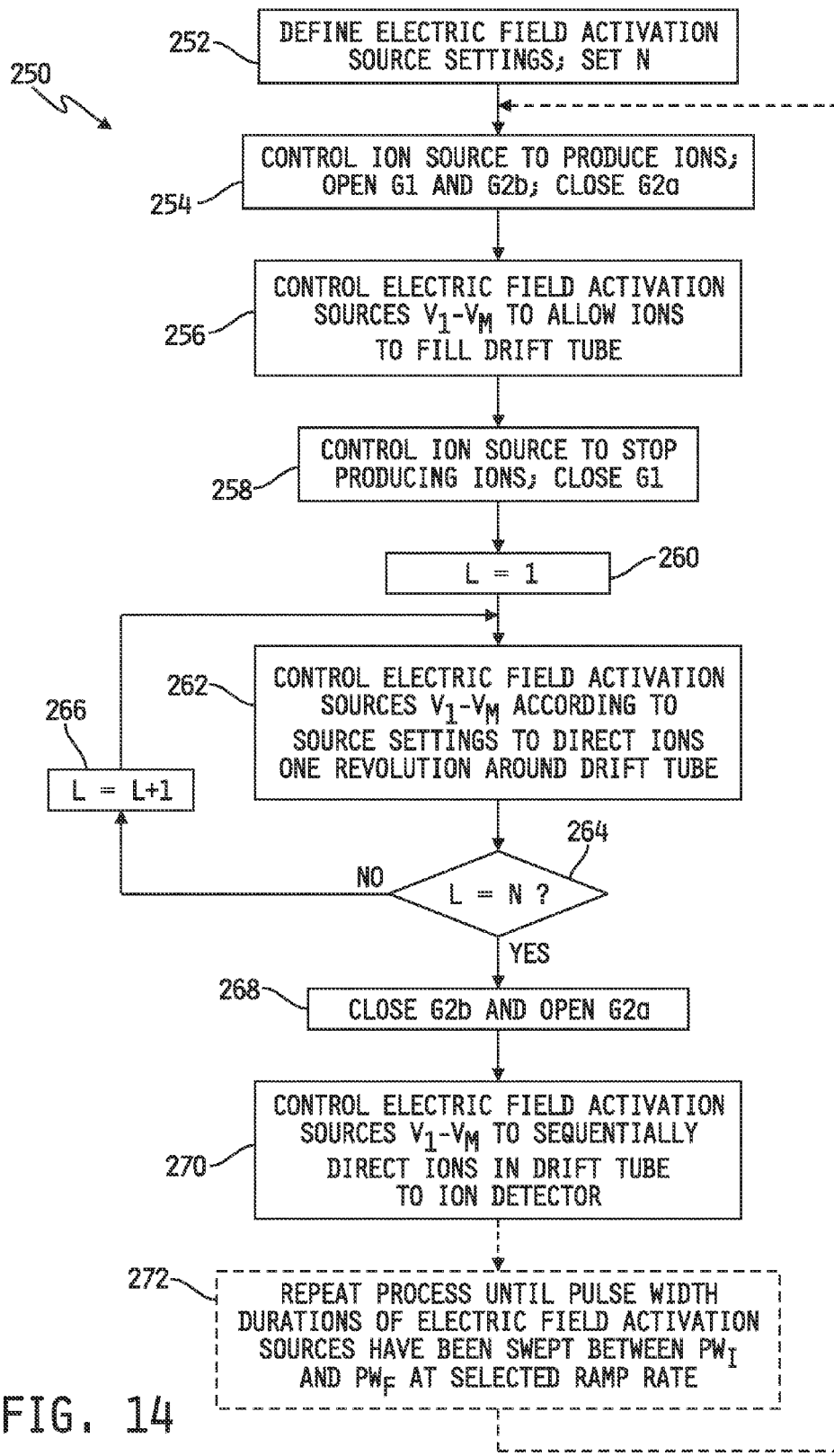
FIG. 14 is a flowchart of one illustrative process for operating the ion mobility spectrometer of FIG. 12B by first pre-filling the drift tube with ions and then sequentially controlling the electric field activation sources to direct ions some number of revolutions around the drift tube in a manner that resolves only ions having a selected mobility or range of mobilities.

Referring now to FIG. 14, a flowchart is shown illustrating a process 250 for operating the ion mobility spectrometer 160 of FIG. 12B to first pre-fill the cyclotron portion of the spectrometer 160 with ions generated by the ion source, and to then operate the spectrometer 160 as described herein to cause only ions supplied by the ion source that have a predefined ion mobility or range of ion mobilities defined by the activation frequency or pulse rate of the number, M, of electric field activation sources, to travel through the spectrometer 160 and/or to sweep the activation frequency or pulse rate of the number, M, of electric field activation sources over a predefined set of activation frequencies or pulse rates to thereby cause ions within the drift tube that have ion mobilities resonant with one or more overtone, e.g., harmonic, frequencies of operation of the electric field activation source, $V_1$-$V_M$, and/or that have ion mobilities resonant with fundamental frequencies of the activation frequencies or pulse rates, i.e., activation times, of the electric field activation sources, $V_1$-$V_M$, for each of the discrete activation frequencies or pulse rates over the predefined set of activation frequencies or pulse rates, to travel through the spectrometer 160. This process provides for a significant increase in sensitivity and resolution compared with operating the ion mobility spectrometer 160 with single pulses or packets of ions produced by the ion source as described above. Illustratively, the process 250 is stored in the memory 20 of the control circuit 18 in the form of instructions that are executable by the control circuit 18 to control operation of the ion mobility spectrometer 160. The process 250 begins at step 252 where the operational settings of the number, M, of electric field activation sources are defined, and a value of an integer, N, is set. In embodiments in which the spectrometer 160 will be operated to produce ions having a mobility or range of mobilities that is/are resonant with only a fundamental frequency, $f_f$, of operation of the electric field activation sources, $V_1$-$V_M$, step 252 may include, for example, the steps 82-88 of the process 80 of FIG. 5. In other embodiments in which the spectrometer 160 will be operated to produce ions having ion mobilities resonant with one or more overtones, e.g., harmonic frequencies, of operation of the electric field activation sources, $V_1$-$V_M$, step 252 may include, for example, the steps 102-106 of the process 100 of FIG. 7. In any case, the value of the integer, N, corresponds to the number of times ions will travel around the cyclotron portion of the drift tube defined by the ion mobility spectrometer 160.

Following step 252, the process 250 advances to step 254 where the control circuit 18 is operable to control the ion source, e.g., ESI-F1/G1, to produce ions and to open the ion gate G1, and to control the ion gate arrangement to open the ion gate G2b and close the ion gage, G2a. By opening the ion gate G1, ions generated by the ion source may thus enter the ion entrance drift tube portion of the drift tube segment D1. By opening the ion gate G2b and closing the ion gage G2a, the generated ions will be confined to the cyclotron portion of the drift tube (D1-D4 and F2-F5) and will be blocked from advancing to the ion detector, DET, as described hereinabove. Thereafter at step 256, the control circuit 18 is operable to control the electric field activation sources, $V_1$-$V_M$, to allow ions produced by the ion source to fill the cyclotron portion of the drift tube, e.g., D1-D4 and F2-F5. In one embodiment, step 256 comprises controlling the electric field activation sources, $V_1$-$V_M$, in a conventional manner to allow ions of different mobilities to enter and advance through the cyclotron portion of the drift tube D1-D4 and F2-F5, i.e., to pass all ions generated by the ion source from each of the plurality of drift tube segments D1-D4 and F2-F5 to the next. This may be done, for example, by simultaneously and identically activating all of the electric field activation sources, $V_1$-$V_M$, such that a continuous, constant electric field is established in all of the ion transmission sections, $d_t$, and ion elimination sections, $d_e$, of each of the adjacent drift tube segments. Those skilled in the art will recognize other techniques for controlling the various electric field activation sources, $V_1$-$V_2$, such that ions generated by the ion source may enter and fill the cyclotron portion of the drift tube D1-D4 and F2-F5, and such other techniques are contemplated by this disclosure.

Following step 256, the process 250 advances to step 258 where the control circuit 18 is operable to control the ion source to stop producing ions and to close the ion gate G1 so that no new ions from the ion source enter the cyclotron portion of the drift tube. Thereafter at step 260, the control circuit 18 is operable to set a counter, L, equal to 1, and thereafter at step 262 the control circuit 18 is operable to control the electric field activation sources, $V_1$-$V_M$, to according to source settings, e.g., those determined at step 252, to direct ions one revolution around the cyclotron portion of the drift tube, i.e., one complete path about the closed cyclotron defined by D1-D4 and F2-F5. Illustratively, the control circuit 18 is operable at step 262 to control the electric field activation sources, $V_1$-$V_M$, by sequentially activating, as described hereinabove with respect to FIG. 5, one or more of the number, M, of electric field activation sources $V_1$-$V_M$, for the time duration, i.e., pulse width for activation of the sources $V_1$-$V_M$ as determined at step 252, while deactivating the remaining number, M, of electric field activation sources to thereby cause only ions within the drift tube (D1-D4 and F2-F5) that have a predefined ion mobility or range of ion mobilities defined by the time duration to travel through the drift tube. In this embodiment, ions having the predefined ion mobility or range of ion mobilities travel, under such control at step 262, one revolution around the drift tube defined by D1-D4 and F2-F5. Thereafter at step 264, the control circuit 18 is operable to determine whether the counter, L, is equal to the number N. If not, the process 250 advances to step 266 where the counter, L, is incremented by 1 and the process 250 then loops back to again execute step 262. If, at step 264, the control circuit 18 determines that L=N, then the ions have traveled around the cyclotron portion of the drift tube (D1-D4 and F2-F5) the selected number of times, N, and the process 250 advances to step 268.

At step 268, the control circuit 18 is operable to control the ion gate arrangement to close the ion gate G2b and open the ion gate G2a, and to control the electric field activation sources, $V_1$-$V_M$, thereafter at step 270 to sequentially direct ions in the cyclotron portion of the drift tube to the ion detector, DET. With the ion gate G2b closed and the ion gate G2a open, sequential operation of the electric field activation sources $V_1$-$V_M$ in the manner just described with respect to step 262 is thus carried out at step 270, in addition to sequentially activating electric fields within F6 and D5 in like manner, to sequentially direct the ions in the cyclotron portion of the drift tube that have the predefined ion mobilities or range of ion mobilities through the ion exit drift tube segment of D4, through F6 and D5, and to the ion detector, DET. Optionally, the process 250 may include an extra step 272, executed following step 270, in which the control circuit 18 is operable to execute steps 254-270 until the pulse width durations, i.e., the "time durations" of activations of the electric field activation sources, $V_1$-$V_M$, have been swept through a range of pulse width durations between an initial pulse width duration, $PW_I$ and a final pulse width duration, $PW_F$. In embodiments which include step 272, step 252 will of course include a determination of $PW_I$ and $PW_F$ as illustrated in the process 100 of FIG. 7. Generally, $PW_I$ and $PW_F$ will be selected to produce one or more overtones, i.e., harmonic frequencies of which the predefined ion mobilities or range of ion mobilities are resonant, and/or to produce ions that have ion mobilities resonant with fundamental frequencies of the activation frequencies or pulse rates, i.e., activation times, of the electric field activation sources, $V_1$-$V_M$, for each of the discrete activation frequencies or pulse rates over and between $PW_I$ and $PW_F$, as described hereinabove.

Figure 15:
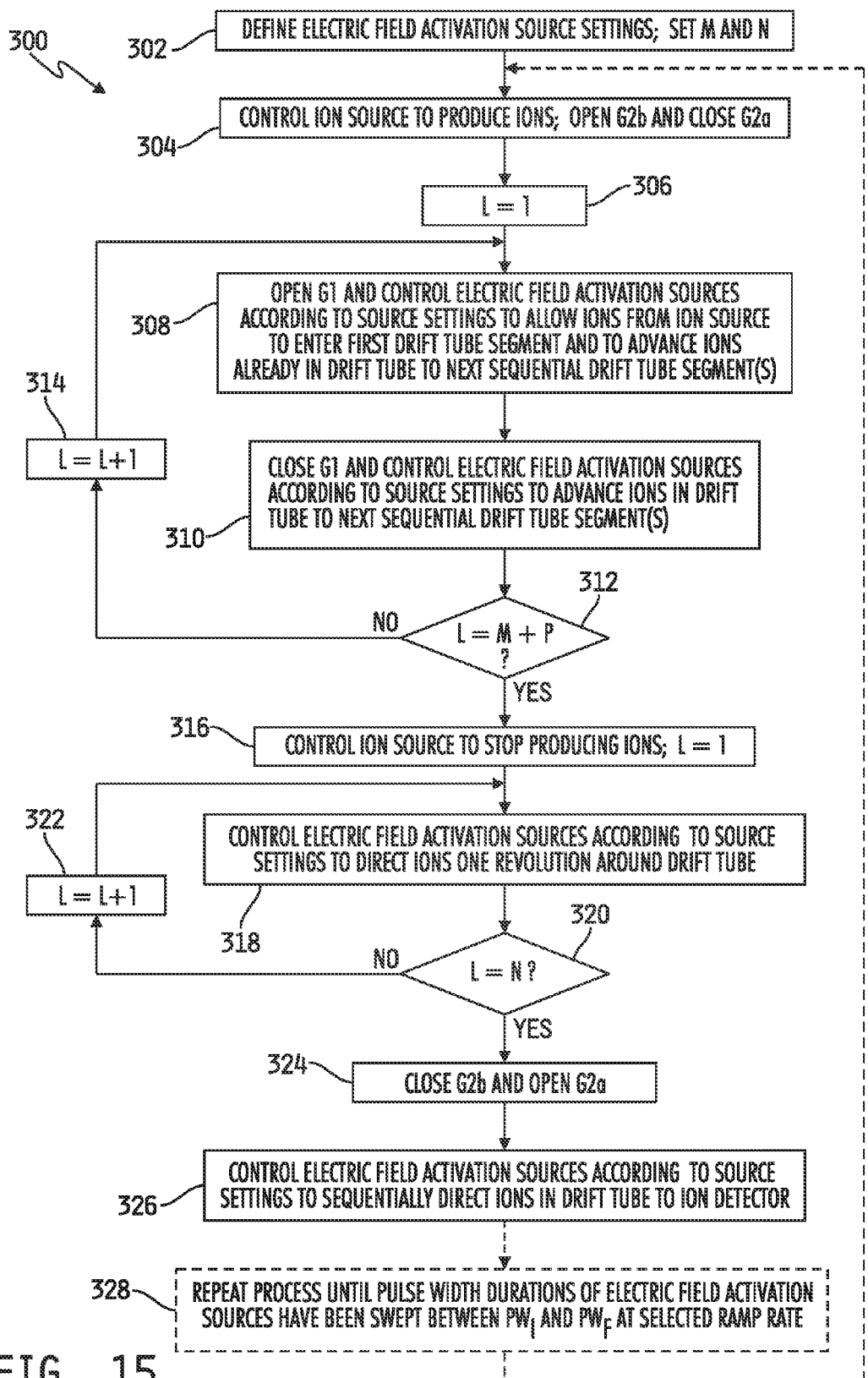
FIG. 15 is a flowchart of another illustrative process for operating the ion mobility spectrometer of FIG. 12B by sequentially controlling the electric field activation sources to direct ions having a selected mobility or range of mobilities around the drift tube while also periodically introducing new ions into the drift tube from the ion source, and then continuing to sequentially control the electric field activation sources to direct ions having the selected mobility or range of mobilities some number of revolutions around the drift tube without introducing new ions into the drift tube such that only ions within the drift tube having the selected mobility or range of mobilities are resolved.

Referring now to FIG. 15, a flowchart is shown illustrating another process 300 for operating the ion mobility spectrometer 160 of FIG. 12B to selectively add ions from the ion source to the cyclotron portion of the spectrometer 160 during each of a first number of revolutions of ions around the cyclotron portion of the drift tube of the ion mobility spectrometer 160 in which only ions that have a predefined ion mobility or range of ion mobilities sequentially advance through the cyclotron portion of the drift tube, and to then stop adding ions and operate the spectrometer 160 as described herein to cause only ions in the cyclotron portion of the drift tube that have the predefined ion mobility or range of ion mobilities defined by the activation frequency or pulse rate of the number, M, of electric field activation sources, to travel around the cyclotron portion of the drift tube a second number of times before being directed to the ion detector. Optionally, this process may also be done while also sweeping the activation frequency or pulse rate of the number, M, of electric field activation sources over a predefined set of activation frequencies or pulse rates to thereby cause ions within the drift tube that have ion mobilities resonant with one or more overtone, e.g., harmonic, frequencies of operation of the electric field activation source, $V_1$-$V_M$, and/or to cause ions that have ion mobilities resonant with fundamental frequencies of the activation frequencies or pulse rates, i.e., activation times, of the electric field activation sources, $V_1$-$V_M$, for each of a number of discrete activation frequencies over the predefined set of activation frequencies or pulse rates, to travel through the spectrometer 160. In any case, the process 300 is illustratively stored in the memory 20 of the control circuit 18 in the form of instructions that are executable by the control circuit 18 to control operation of the ion mobility spectrometer 160.

The process 300 begins at step 302 where the operational settings of the number, M, of electric field activation sources are defined, and values of two integers, N and M are set. In embodiments in which the spectrometer 160 will be operated to produce ions having a mobility or range of mobilities that is/are resonant with only a fundamental frequency, $f_f$, of operation of the electric field activation sources step 252 may include, for example, the steps 82-88 of the process 80 of FIG. 5. In other embodiments in which the spectrometer 160 will be operated to produce ions having ion mobilities resonant with one or more overtones, e.g., harmonic frequencies, of operation of the electric field activation sources step 252 may include, for example, the steps 102-106 of the process 100 of FIG. 7. In any case, the integer M set at step 302 is different from, and should not be confused with, the number, M, of electric field activation sources.

Following step 302, the process 300 advances to step 304 where the control circuit 18 is operable to control the ion source, e.g., ESI-F1/G1, to produce ions and to control the ion gate arrangement to open the ion gate G2b and close the ion gate, G2a. By opening the ion gate G1, ions generated by the ion source may thus enter the ion entrance drift tube portion of the drift tube segment D1. By opening the ion gate G2b and closing the ion gate G2a, ions introduced into the spectrometer 160 via the ion source will be confined to the cyclotron portion of the drift tube and will be blocked from advancing to the ion detector, DET, as described hereinabove. Thereafter at step 306, the control circuit 18 is operable to set a counter, L, equal to 1.

Following step 306, the process 300 advances to step 308 where the control circuit 18 is operable to control the ion source to open the ion gate G1, and to control the electric field activation sources, $V_1$-$V_M$, to according to source settings, e.g., those determined at step 302, to allow ions from the ion source to enter the first drift tube segment, e.g., D1, and to also advance ions already in the cyclotron portion of the drift tube to the next sequential drift tube segment(s). Thereafter at step 310, the control circuit 18 is operable to close the ion gate G1, and to control the electric field activation sources, $V_1$-$V_M$, according to the source settings to advance ions in the cyclotron portion of the drift tube to the next sequential drift tube segment(s). Optionally, step 310 may also include controlling the ion source to stop producing ions and step 308 may include controlling the ion source to produce ions. In any case, following step 310 the process 300 advances to step 312 where the control circuit 18 determines whether the counter, L, is equal to the sum of the integer M and another integer P. If not, the process advances to step 314 where the counter, L, is incremented by 1 before again executing steps 308 and 310. If, at step 312, the control circuit 18 determines that L=M+P, the process 300 advances to step 316 where the control circuit 18 controls the ion source to stop producing ions and to reset the counter, L, equal to 1.

The sub-process of the process 300 between and including steps 302 and 316 controls the ion mobility spectrometer 160 as described hereinabove to sequentially advance only ions around the cyclotron portion of the drift tube having ion mobilities or range of ion mobilities defined by the activation pulse widths, i.e., time durations of activation, of the electric field activation sources. During this process ions generated by the ion source are also selectively added to the first drift tube segment, D1, during and throughout a selected number, M, of revolutions of the ions around the cyclotron portion of the drift tube (D1-D4 and F2-F5). This sub-process of the process 300 between and including steps 302 and 316 may be referred to herein as "selective enhancement." The integer P corresponds to the number of times steps 308 and 310 must be executed to sequentially fill and advance ions one revolution around the cyclotron portion of the drift tube, and the integer M corresponds to the number of times steps 308 and 310 must be executed to continue the process of sequentially filling and advancing ions one revolution around the cyclotron portion of the drift tube in order to direct the ions completely around the cyclotron portion of the drift tube a desired number of times while also selectively adding ions to the drift tube. The total number of revolutions, R, of the ions around the cyclotron portion of the drift tube when the "YES" branch of step 312 is satisfied will thus be M/P+1.

Figure 16A:
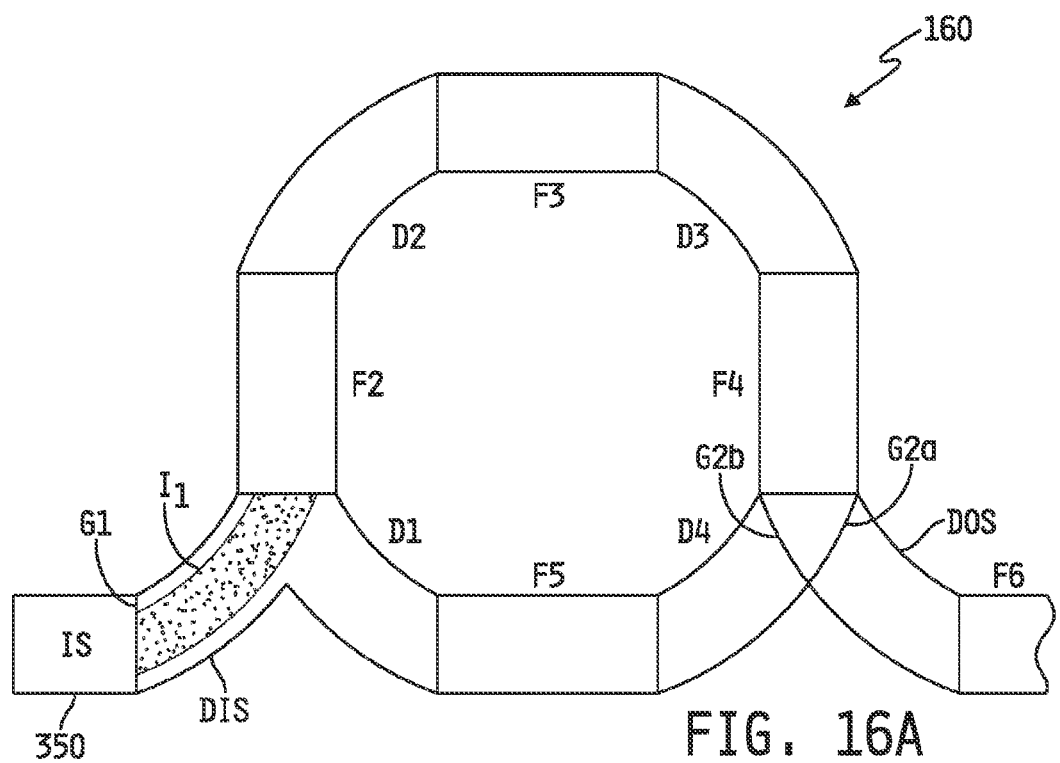
FIGS. 16A-16L are successive or sequential block diagrams of one illustrative embodiment of the ion mobility spectrometer of FIG. 12B illustrating operation of the spectrometer during the part of the process illustrated in the flowchart of FIG. 15 in which the electric field activation sources are sequentially controlled to direct ions having a selected mobility or range of mobilities around the drift tube while also periodically introducing new ions into the drift tube from the ion source.
Figure 16B:
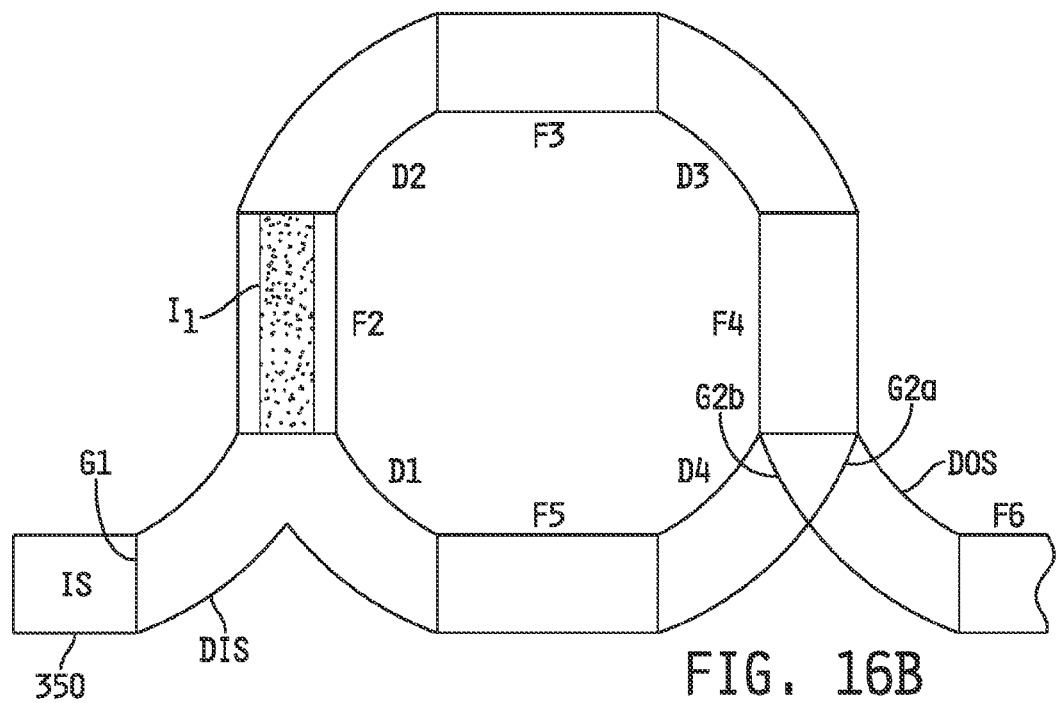
Figure 16C:
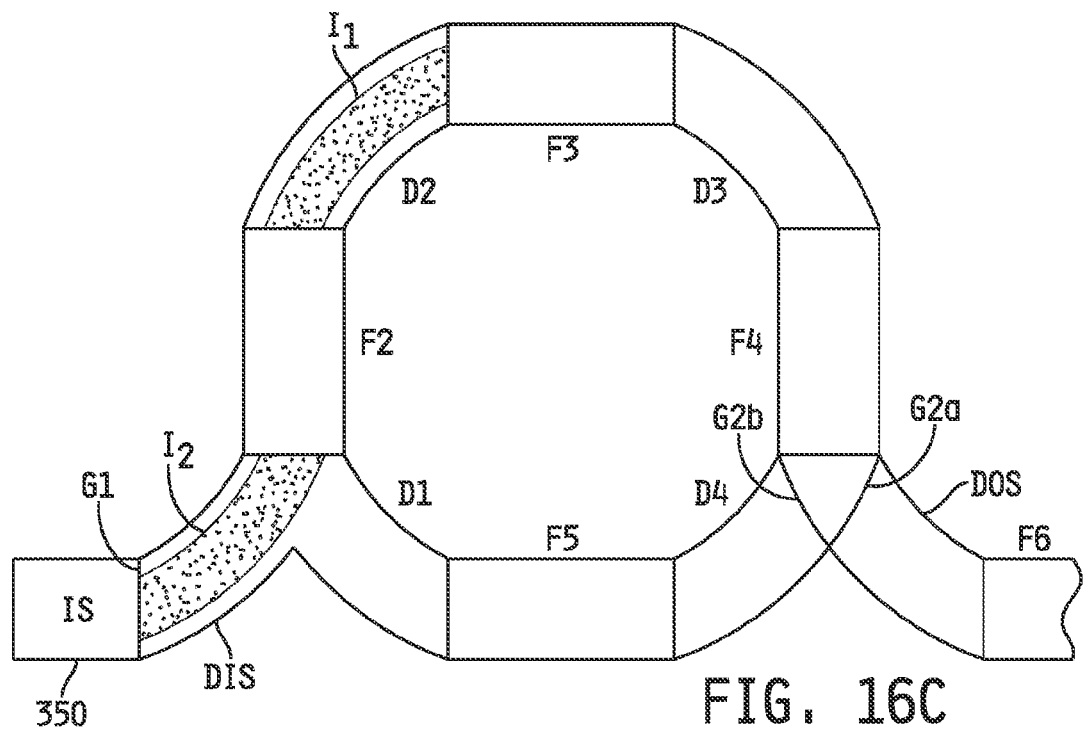

Referring now to FIGS. 16A-16L, the selective enhancement sub-process of the process 300 is graphically illustrated in the context of the various drift tube sections of the cyclotron ion mobility spectrometer 160 of FIG. 12B. It will be understood that in FIGS. 16A-16L the ion mobility spectrometer 160 is partitioned into eight cascaded drift tube segments D1-D4 and F2-F5 each having an ion transmission section, $d_t$, and an ion elimination region, $d_e$, between the ion outlet of the ion transmission section and the ion inlet of the ion transmission section of the next adjacent segment. Thus, D1 has an ion elimination region between the ion outlet of D1 and the ion inlet of F2, F2 has an ion elimination region between the ion outlet of F2 and the ion inlet of D2, etc. The ion elimination regions, $d_e$, are not specifically shown in FIGS. 16A-16L, although it will be understood that electric fields within these regions are established as described hereinabove with respect to FIGS. 1-4 under control of the plurality of electric field activation sources, $V_1$-$V_M$. In alternative embodiments, as described hereinabove, the drift tube segments D1-D4 may be sized to serve as the ion transmission sections and the funnel segments F2-F5 may be sized smaller and serve as the ion elimination regions to D1-D4 respectively, or the funnel segments F2-F5 may be sized to serve as the ion transmission sections and the drift tube segments D1-D4 may be sized smaller and serve as the ion elimination regions to F2-F5 respectively. In any case, each sequential pair of FIGS. 16A-16L represent sequential snapshot of ions within the spectrometer 160 at the end of steps 308 and 310 respectively. Thus, for example, FIG. 16A represents a snapshot of ions within the spectrometer 160 at the end of the first execution of step 308, FIG. 16B represents a snapshot of ions within the spectrometer 160 at the end of the first execution of step 310, FIG. 16C represents a snapshot of ions within the spectrometer at the end of the second execution of step 308, etc.

Referring to FIG. 16A, the first execution of step 308 has occurred, and a group or packet of ions, I1, generated by the ion source 350 has moved through the ion inlet gate, G1, at the entrance of the ion entrance drift tube segment of D1, and has moved under the influence of an electric field established in the ion entrance drift tube segment of D1 toward the ion outlet of the ion transmission segment of D1. In FIG. 16B, the ion gate G1 has been closed, and the ion packet I1 has moved under the influence of an electric field established in D1/F2 toward the ion outlet of the ion transmission segment of F2.

Figure 16D:
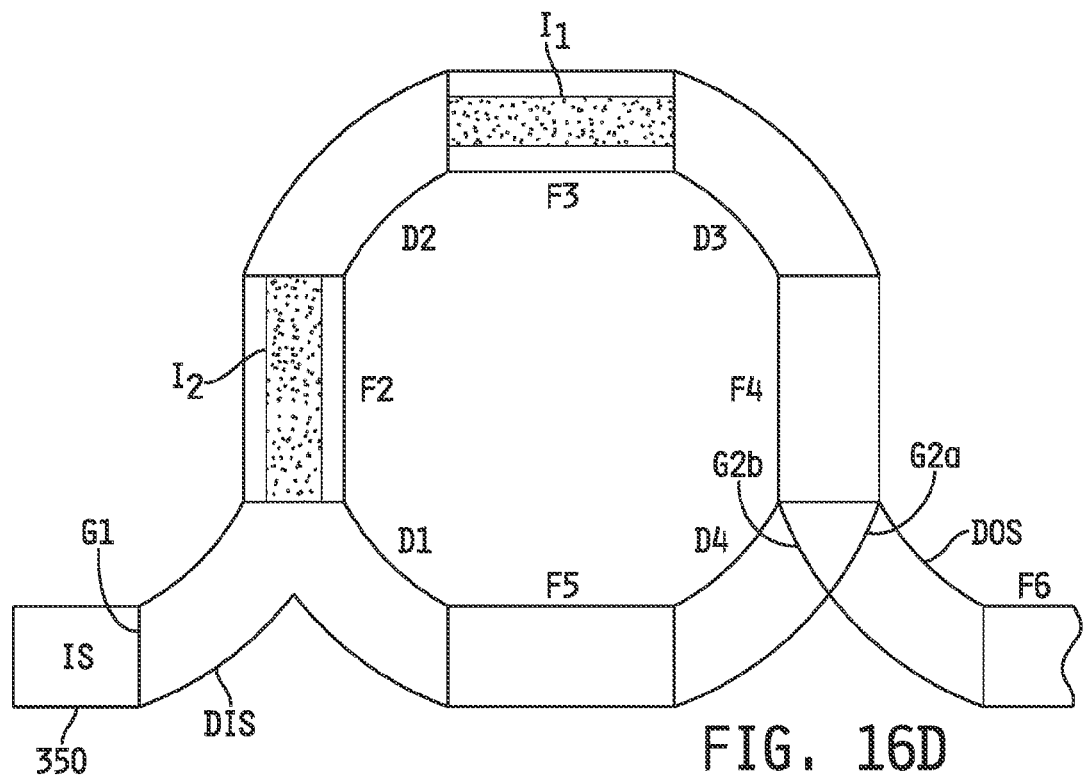

In FIG. 16C, the ion packet I1 has moved under the influence of an electric field established in F2/D2 toward the ion outlet of the ion transmission segment of D2. At the same time, the ion gate G1 has been opened and another packet of ions, I2, generated by the ion source 350 has moved through the ion entrance drift tube segment of D1, and has moved under the influence of an electric field established in the ion entrance drift tube segment of D1 toward the ion outlet of the ion transmission segment of D1. In FIG. 16D, the ion gate G1 has been closed, and the ion packet I1 has moved under the influence of an electric field established in D2/F3 toward the ion outlet of the ion transmission segment of F3 and the ion packet I2 has moved under the influence of an electric field established in D1/F2 toward the ion outlet of the ion transmission segment of F2.

Figure 16E:
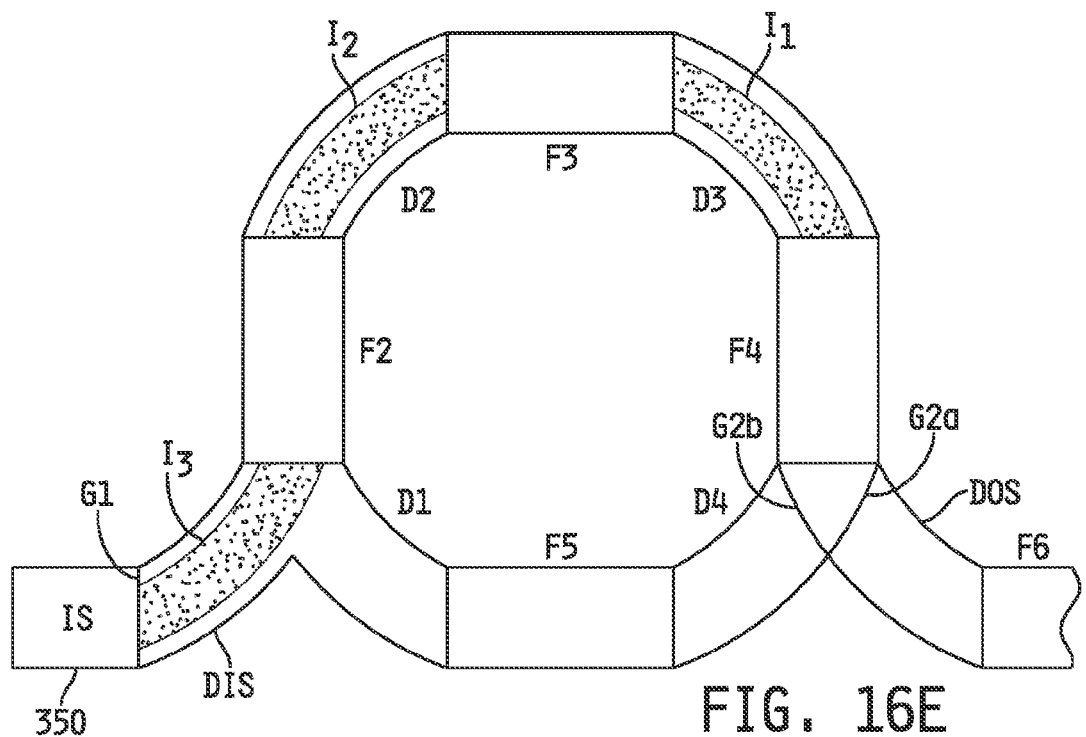
Figure 16F:
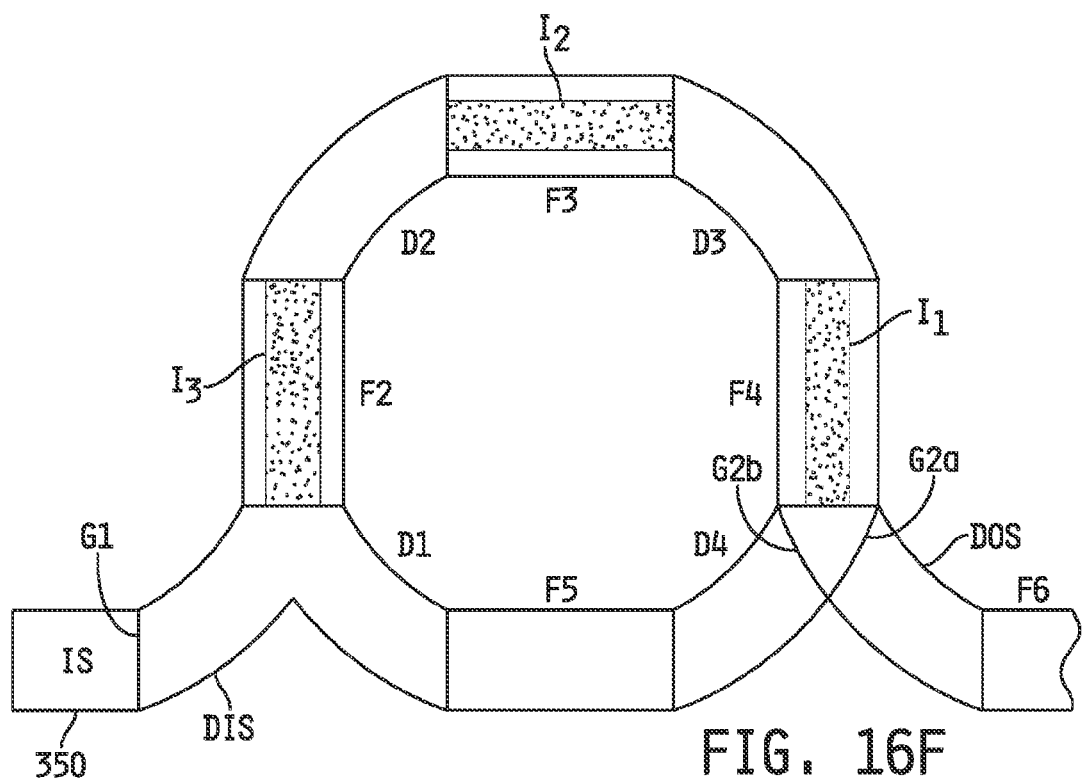

In FIG. 16E, the ion packet I1 has moved under the influence of an electric field established in F3/D3 toward the ion outlet of the ion transmission segment of D3, and the ion packet I2 has moved under the influence of an electric field established in F2/D2 toward the ion outlet of the ion transmission segment of D2. At the same time, the ion gate G1 has again been opened and another packet of ions, I3, generated by the ion source 350 has moved through the ion entrance drift tube segment of D1, and has moved under the influence of an electric field established in the ion entrance drift tube segment of D1 toward the ion outlet of the ion transmission segment of D1. In FIG. 16F, the ion gate G1 has been closed, and the ion packet I1 has moved under the influence of an electric field established in D3/F4 toward the ion outlet of the ion transmission segment of F4, the ion packet I2 has moved under the influence of an electric field established in D2/F3 toward the ion outlet of the ion transmission segment of F3, and the ion packet I3 has moved under the influence of an electric field established in D1/F2 toward the ion outlet of the ion transmission segment of F2.

Figure 16G:
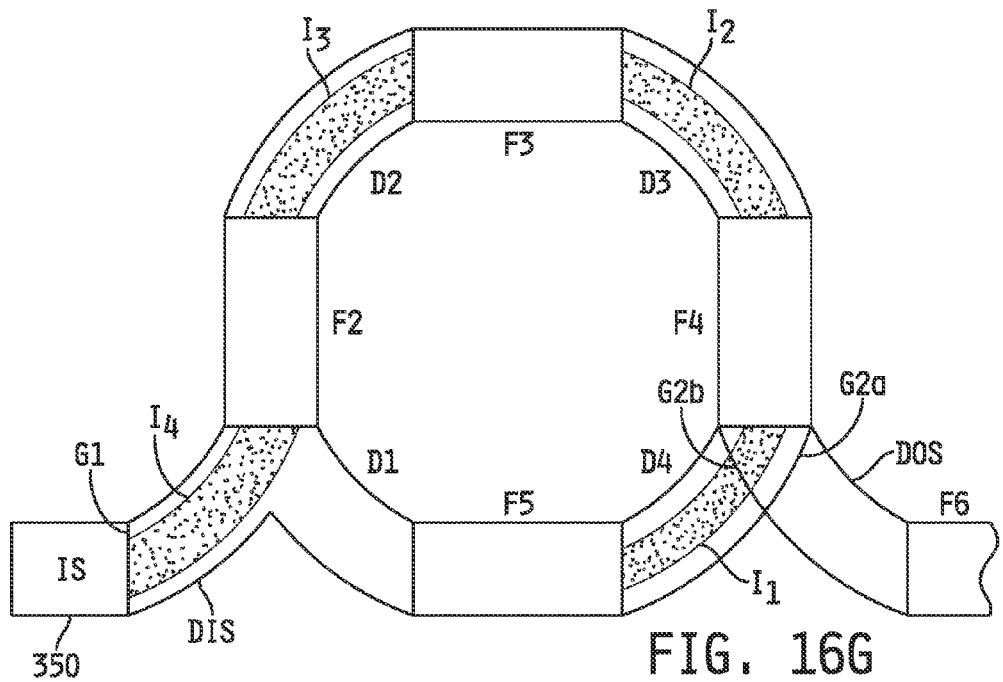
Figure 16H:
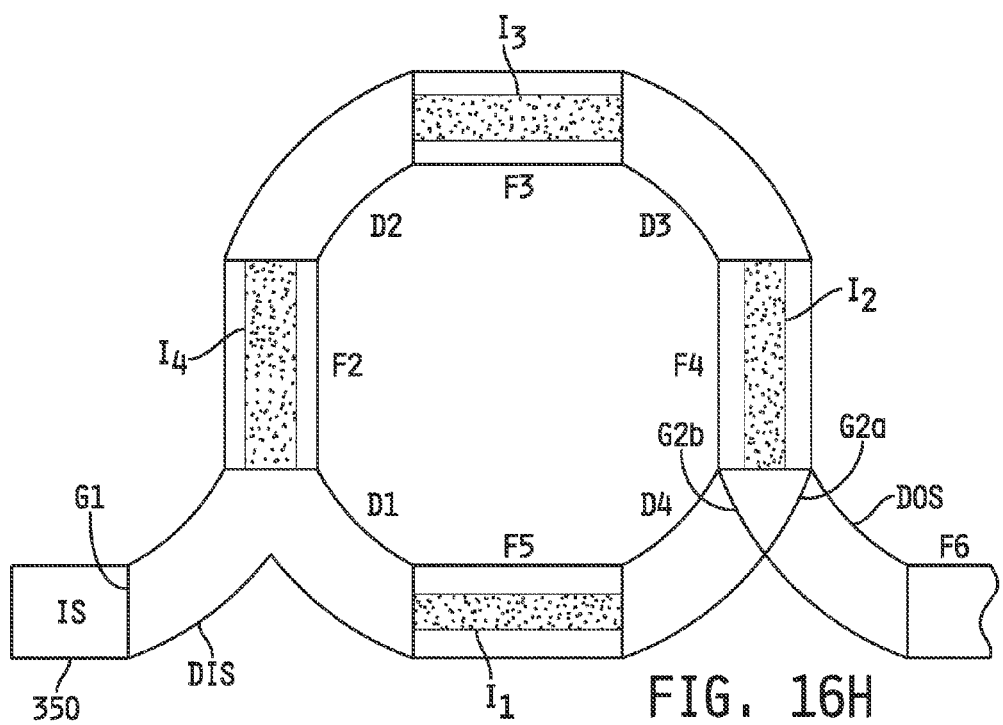

In FIG. 16G, the ion packet I1 has moved under the influence of an electric field established in F4/D4 toward the ion outlet of the ion transmission segment of D4 (since G2a is closed and G2b is open), the ion packet I2 has moved under the influence of an electric field established in F3/D3 toward the ion outlet of the ion transmission segment of D3 and the ion packet I3 has moved under the influence of an electric field established in F2/D2 toward the ion outlet of the ion transmission segment of D2. At the same time, the ion gate G1 has again been opened and another packet of ions, I4, generated by the ion source 350 has moved through the ion entrance drift tube segment of D1, and has moved under the influence of an electric field established in the ion entrance drift tube segment of D1 toward the ion outlet of the ion transmission segment of D1. In FIG. 16H, the ion gate G1 has been closed, and the ion packet I1 has moved under the influence of an electric field established in D4/F5 toward the ion outlet of the ion transmission segment of F5, the ion packet I2 has moved under the influence of an electric field established in D3/F4 toward the ion outlet of the ion transmission segment of F4, the ion packet I3 has moved under the influence of an electric field established in D2/F3 toward the ion outlet of the ion transmission segment of F3 and the ion packet I4 has moved under the influence of an electric field established in D1/F2 toward the ion outlet of the ion transmission segment of F2.

Figure 16I:
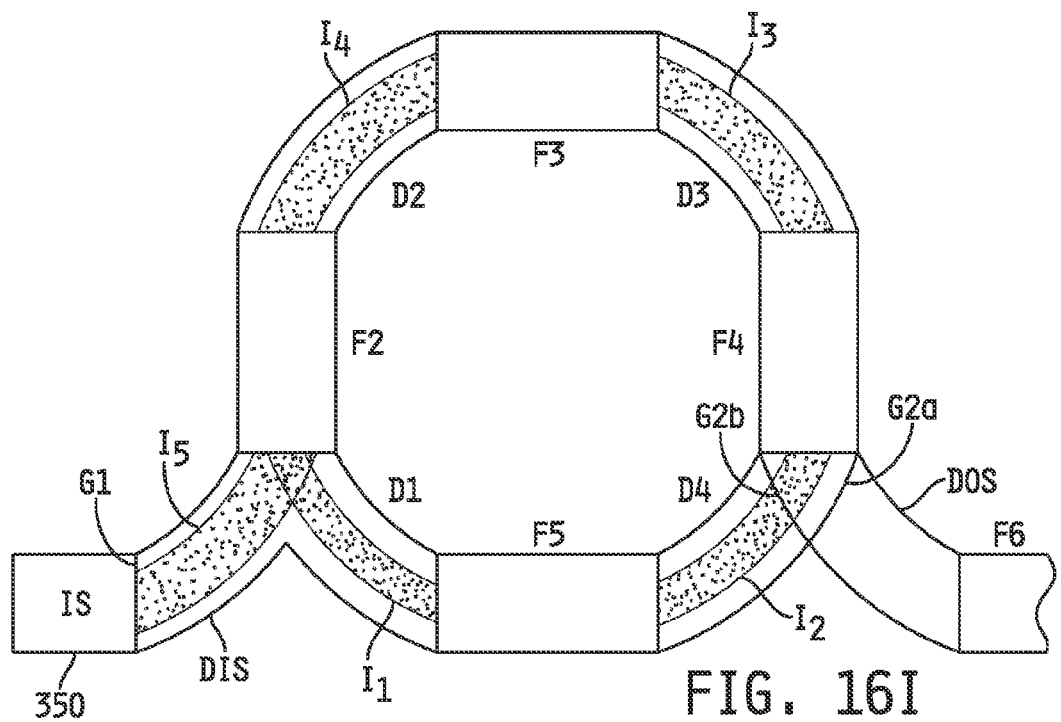

In FIG. 16I, the ion packet I1 has moved under the influence of an electric field established in the cyclotron portion of F5/D1 toward the ion outlet of the ion transmission segment of D1, the ion packet I2 has moved under the influence of an electric field established in F4/D4 toward the ion outlet of the ion transmission segment of D4, the ion packet I3 has moved under the influence of an electric field established in F3/D3 toward the ion outlet of the ion transmission segment of D3 and the ion packet I4 has moved under the influence of an electric field established in F2/D2 toward the ion outlet of the ion transmission segment of D2. At the same time, the ion gate G1 has again been opened and another packet of ions, I5, generated by the ion source 350 has moved through the ion entrance drift tube segment of D1, and has moved under the influence of an electric field established in the ion entrance drift tube segment of D1 toward the ion outlet of the ion transmission segment of D1. It will be observed in FIG. 16I that as ion packets move from D2 to D1, the widths of the ion packets I4-I1 respectively decrease. This decrease in ion packet width is intended to represent a filtering of ions according to ion mobility (determined by activation pulse width of the electric field activation sources) such that fewer ions are included in I1 than in I2, fewer ions are included in I2 than in I3, etc. The ions in ion packet I1 are thus more highly resolved than those in I2, etc. because the illustrated ion mobility filtering process sequentially eliminates more ions having ion mobility or range of ion mobilities outside of that defined by the activation pulse width, i.e., the time duration of activation, of the electric field activation sources, $V_1$-$V_M$ as the ions sequentially move through the various drift tube segments of the cyclotron portion of the ion mobility instrument 160.

Figure 16J:
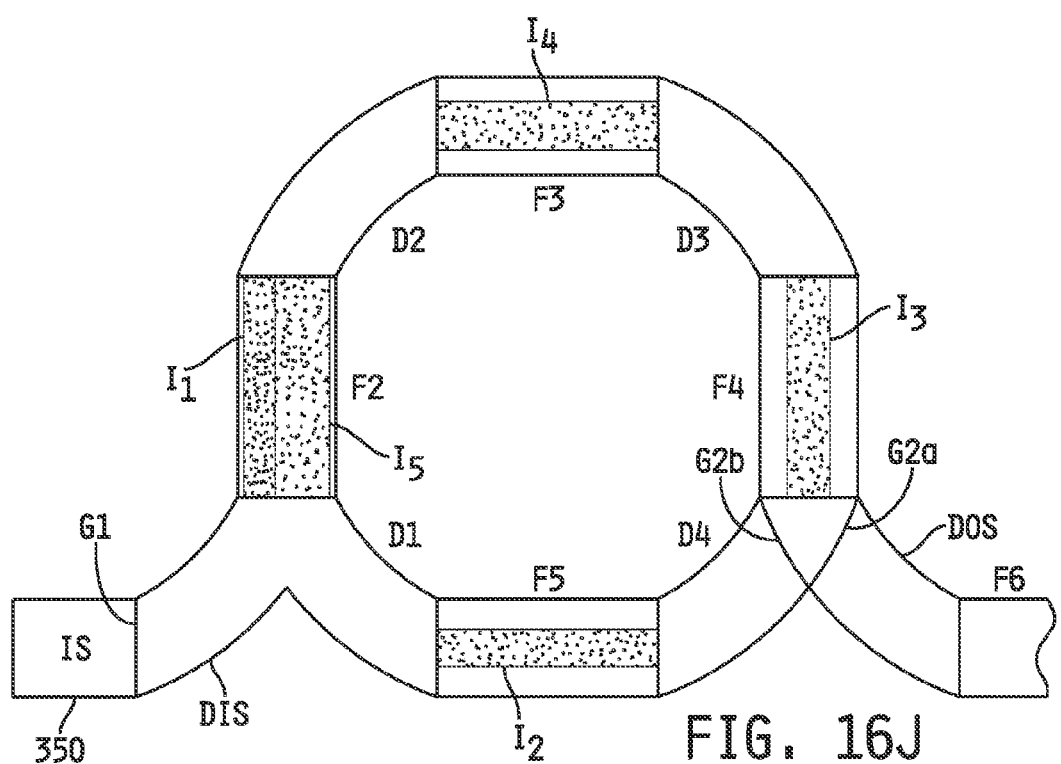

In FIG. 16J, the ion gate G1 has been closed, and the ion packets I1 and I5 have together moved under the influence of an electric field established in D1/F2 toward the ion outlet of the ion transmission segment of F2 such that ion packets I1 and I5 are now combined in F2. The ion packet I2 has also moved under the influence of an electric field established in D4/F5 toward the ion outlet of the ion transmission segment of F5, the ion packet I3 has moved under the influence of an electric field established in D3/F4 toward the ion outlet of the ion transmission segment of F4 and the ion packet I4 has moved under the influence of an electric field established in D2/F3 toward the ion outlet of the ion transmission segment of F3.

Figure 16K:
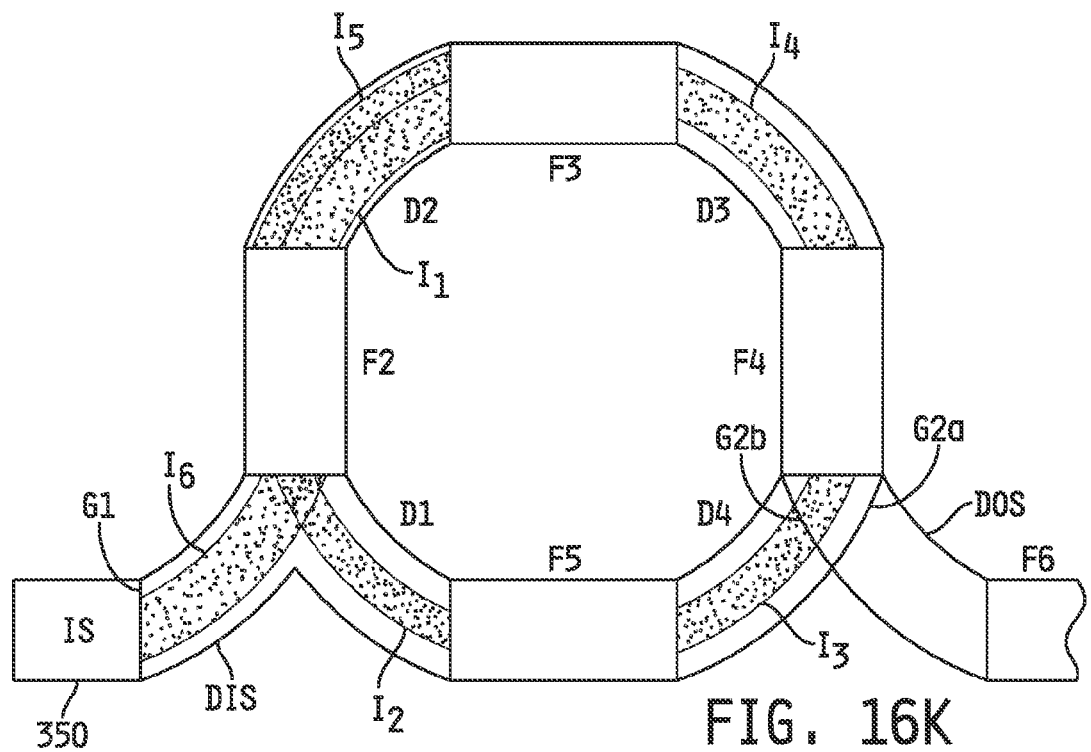
Figure 16L:
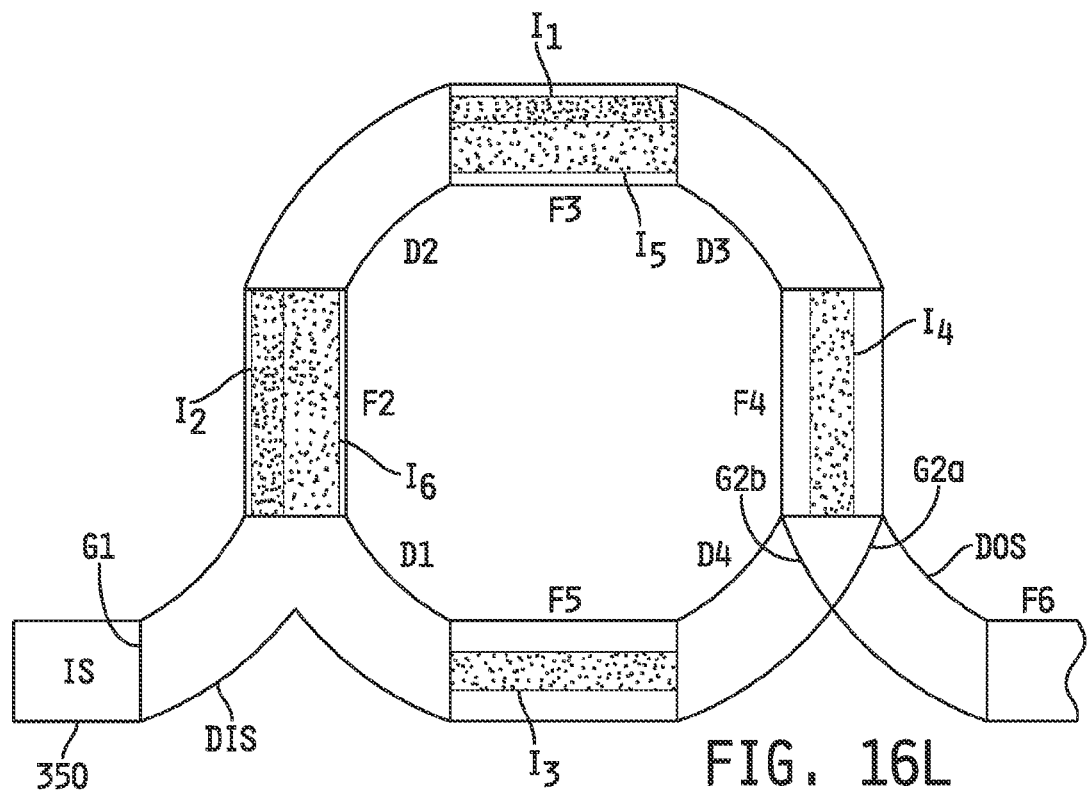

In FIG. 16K, the ion packet I2 has moved under the influence of an electric field established in the cyclotron portion of F5/D1 toward the ion outlet of the ion transmission segment of D1, the ion packet I3 has moved under the influence of an electric field established in F4/D4 toward the ion outlet of the ion transmission segment of D4, the ion packet I4 has moved under the influence of an electric field established in F3/D3 toward the ion outlet of the ion transmission segment of D3 and the combination of ion packets I1 and I5 have moved under the influence of an electric field established in F2/D2 toward the ion outlet of the ion transmission segment of D2. At the same time, the ion gate G1 has again been opened and another packet of ions, I6, generated by the ion source 350 has moved through the ion entrance drift tube segment of D1, and has moved under the influence of an electric field established in the ion entrance drift tube segment of D1 toward the ion outlet of the ion transmission segment of D1. In FIG. 16L, the ion gate G1 has been closed, and the ion packets I2 and I6 have together moved under the influence of an electric field established in D1/F2 toward the ion outlet of the ion transmission segment of F2 such that ion packets I2 and I6 are now combined in F2. The ion packet I3 has also moved under the influence of an electric field established in D4/F5 toward the ion outlet of the ion transmission segment of F5, the ion packet I4 has moved under the influence of an electric field established in D3/F4 toward the ion outlet of the ion transmission segment of F4 and the combination of ion packets I1 and I5 has moved under the influence of an electric field established in D2/F3 toward the ion outlet of the ion transmission segment of F3.

Referring again to FIG. 15, the sub-process carried out by steps 302-316 of the process 300 and illustrated in FIGS. 16A-16L can be executed any number of times to selectively add ions to individual packets of ions circulating through the various drift tube segments D1-D4 and F2-F5 of the ion mobility spectrometer 160. As illustrated in FIGS. 16A-16H, the loop defined by steps 308-314 is executed four times to complete one revolution of ions around the cyclotron portion (D1-D4 and F2-F5) of the ion mobility spectrometer 160. Thus, "P" at step 312 is equal to four in the illustrated embodiment, and the counter value "M" is therefore selected such that the total desired number of revolutions, R, of ions around the cyclotron portion of the ion mobility spectrometer 160 during the selective enhancement sub-process of steps 302-316, i.e., during which ions from the ion source 350 are selectively added to ions already circulating through the cyclotron portion of the spectrometer 160, must satisfy the relation R=M/P+1 as described above.

It will be understood that the ion mobility spectrometer 160 may be controlled and operated using similar yet alternate techniques to perform the selective enhancement process just illustrated and described with respect to FIGS. 16A-16L. For example, the spectrometer 160 may be alternatively operated such that ions from the ion source 350 fill the D1 and F2 regions during one field application setting. Next the fields would switch such that ions from F2 would move into the D2 region while ions from the source 350 would be shut off. Application of the next field would see the transmission of the ions with resonant mobilities into the F3 region. At the same time, ions from the ion source 350 would be allowed to fill the D1 and F2 regions again. Completion of another two field application periods would yield ions in the F4 and F3 regions with a filling of the D1 and F2 regions. Yet another two application periods would result in ions in the F5, F4, and F3 regions as well as a filling of the D1 and F2 regions. With the addition of two more application periods the first ion packet would reach the F2 region again having completed a full cycle around the cyclotron portion of the drift tube (D1-D4 and F2-F5). During this time, ions from the source would be allowed into the D1 and F2 region combining with this ion packet. Another cycle would see the filtering of these added ions according to resonant mobilities. Ions could be added to each successive packet for a desired amount of time or a desired number of cycles around the cyclotron portion of the drift tube (D1-D4 and F2-F5). Alternatively still, the process just described could be modified to move ions around the cyclotron portion of the spectrometer 160 using longer ion transmission regions. For example, the spectrometer 160 may be alternatively operated such that ions from the ion source 350 fill the D1 and F2 regions during one field application setting. The ion source may then be shut off and an electric field may be activated in the D1/F2/D2/F3 region to move ions into the D2/F3 region, etc. Ions may thus be moved through the cyclotron portion of the spectrometer 160 by propagating two regions worth of ions around the cyclotron portion using fewer field applications to complete each traversal of the cyclotron portion of the spectrometer 160.

As described hereinabove, the design of the cyclotron portion of the drift can be altered from that described above such that the D regions comprise the ion transmission regions, $d_t$, and the F regions comprise the ion elimination regions, $d_e$, or such that the F regions comprise the ion transmission regions, $d_t$, and the D regions comprise the ion elimination regions, $d_e$. Those skilled in the art will recognize that the selective enhancement sub-process just described comprising steps 302-316 may be easily modified to be performed using such an alternate design of the cyclotron portion of the drift tube (D1-D4 and F2-F5), and that any such modifications to steps 302-316 would be a mere mechanical step for a skilled artisan.

Referring again to FIG. 15, the process 300 advances from step 316 to steps 318-326, and optional also to step 328. Steps 318-328 are identical to steps 262-272 illustrated and described hereinabove with respect to FIG. 14, in which the control circuit 18 is operable to control the electric field activation sources, $V_1$-$V_M$, and the ion gates G2a and G2b to cause the ions within the cyclotron portion of the ion mobility spectrometer 160 to travel around the cyclotron drift tube "N" times prior to directing the ions to the ion detector, DET, where N may be any positive integer. Optionally, step 328 may be included to perform overtone analysis, as this process is described above, using the combination of the selective enhancement sub-process described above followed by controlling the spectrometer 160 to circulate the post-selectively enhanced ions in the cyclotron drift tube N times prior to directing the ions toward the ion detector, DET.

Mixtures may alternatively be resolved over long distances in linear drift tubes, e.g., of the type illustrated in FIGS. 1-4, at or near their fundamental frequencies by controlling the electric field activation sources, $V_1$-$V_M$, in a manner that directs ions back and forth between the ends of the drift tube. More specifically, ions entering the ion inlet of the drift tube 14 are directed by the electric field activation sources, $V_1$-$V_M$, toward the ion outlet of the drift tube 14 by selectively controlling the activation times and pulse widths of the electric field activation sources as described hereinabove with respect to FIGS. 1-5. In this embodiment, prior to reaching the ion outlet, e.g., at or near the last drift tube segment, the control circuit 18 may control the electric field activation sources, $V_1$-$V_M$, to reverse the direction of the sequentially applied electric fields to the cascaded drift tube segments such that the ions reverse direction and move linearly toward the ion inlet of the drift tube 14. As before, the duration of the pulse widths, PW, would determine the range of ion mobilities of the ions traversing the drift tube 14. In any case, this may be repeated any number of times to allow the ions to drift any desired distance. After drifting the desired distance, a gate at the ion outlet of the drift tube 14 may be activated to allow the ions to exit the ion outlet of the drift tube 14 and be detected by an ion detector positioned to detect ions exiting the drift tube.

Running the drift separation in a back and forth manner as just described can be limited in that ions that limit resolving power, e.g., those with slightly mismatched mobilities, may not eliminated as they move back to their initial positions on all even passes (i.e., the $2^{nd}$, $4^{th}$, $6^{th}$ etc. pass through the drift tube). This limitation may be overcome by, for example, randomizing positions of the ions in the drift tube during each pass of ions from the first drift tube segment to the last and/or during each pass of ions from the last drift tube segment to the first.

Figure 17:
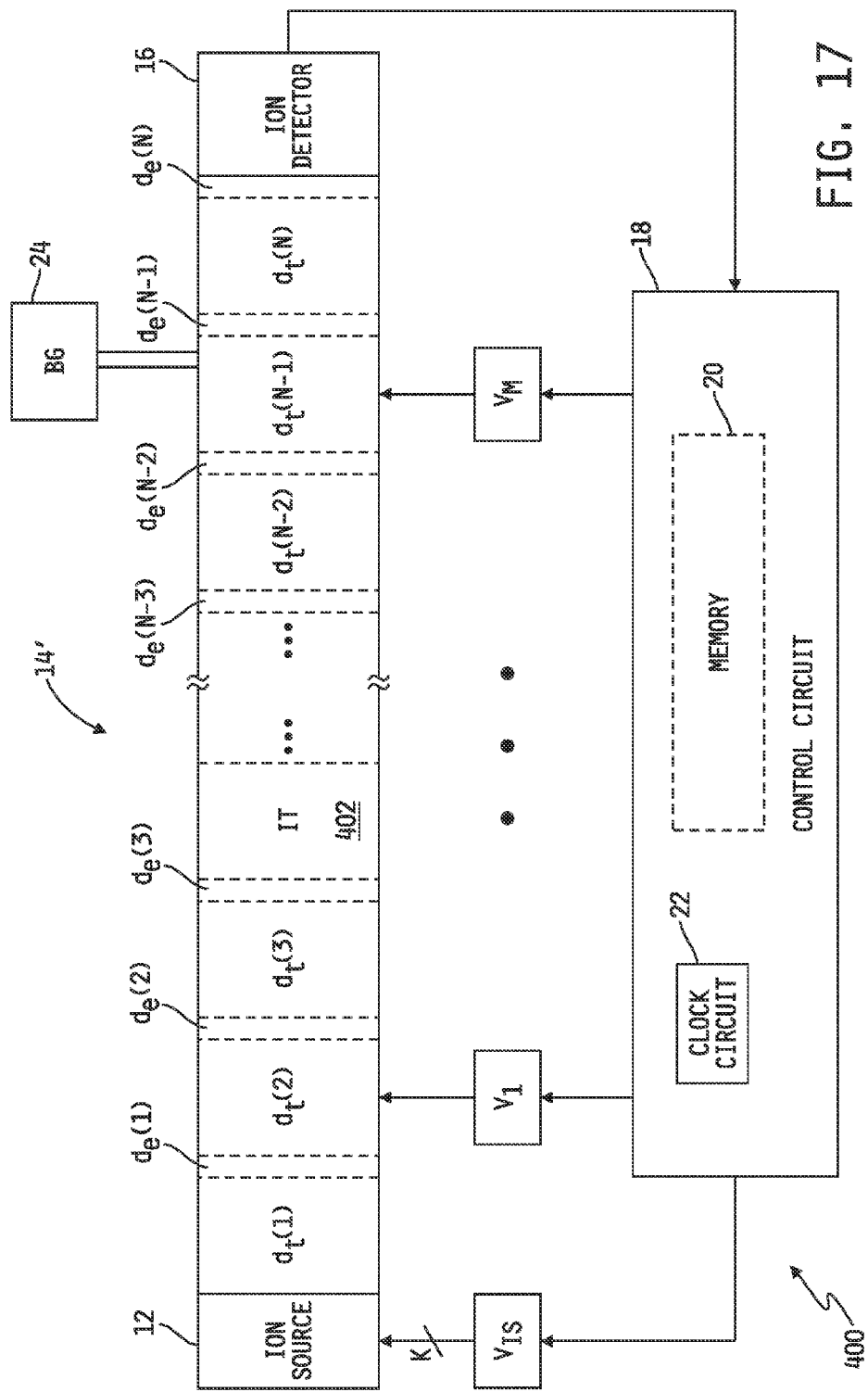
FIG. 17 is a block diagram of another illustrative embodiment of an ion mobility spectrometer instrument.

Referring now to FIG. 17, one illustrative embodiment of an ion mobility spectrometer 400 is shown having a linear drift tube 14' that is configured to randomize ion positions during each such pass of ions. The drift tube 14' is identical to the drift tube 14 illustrated and described hereinabove with respect to FIGS. 1-4 except that a conventional ion trap 402 is positioned between two adjacent ones of the number, N, of cascaded drift tube segments, e.g., between the ion outlet of the third ion elimination region, $d_e(3)$ and the ion inlet of the fourth ion transmission region, $d_t(4)$. All other features of the drift tube 14' are identical to the drift tube 14 illustrated and described hereinabove, and all other components of the ion mobility spectrometer 400 are identical to correspondingly numbered components of the ion mobility spectrometer 10 illustrated and described hereinabove. The primary purpose of the ion trap 402 in the spectrometer 400 is to trap ions of the desired mobility during each pass of ions from the first drift tube segment to the last and/or during each pass of ions from the last drift tube segment to the first to thereby randomize the positions of the ions during each such pass. In this regard, the memory 20 of the processor 18 has, in this embodiment, instructions stored therein that are executable by the processor 18 to control the ion trap, e.g., via a suitable voltage source or voltage sources, which may or may not be, or be part of, one or more of the electric field activation sources, $V_1$-$V_M$, to trap ions therein during each pass of ions from the first drift tube segment to the last and/or during each pass of ions from the last drift tube segment to the first for a trap period selected to allow ions trapped within the ion trap 402 to randomize their positions relative to the ion trap 402 and thereby randomize their positions relative to the drift tube 14'. During the trap period, ions will thus randomize their positions, causing a greater mismatch in timing for a population of undesired ions, e.g., those with slightly off-resonance mobilities. This will lead to more effective elimination of these undesired ions. It will be understood that the ion trap 402 illustrated in FIG. 17 may be alternatively positioned anywhere along its length, i.e., at either end or between any two adjacent drift tube segments. Alternatively or additionally, the drift tube 14' may include two or more such ion traps 402 positioned anywhere along its length. In one specific embodiment, for example, one such ion trap 402 is positioned at one end of the drift tube 14' and another such ion trap 402 is positioned at an opposite end of the drift tube 14'. In this embodiment, the control circuit controls each ion trap to trap ions therein during each pass of ions from one end of the drift tube tot the other.

Figure 18:
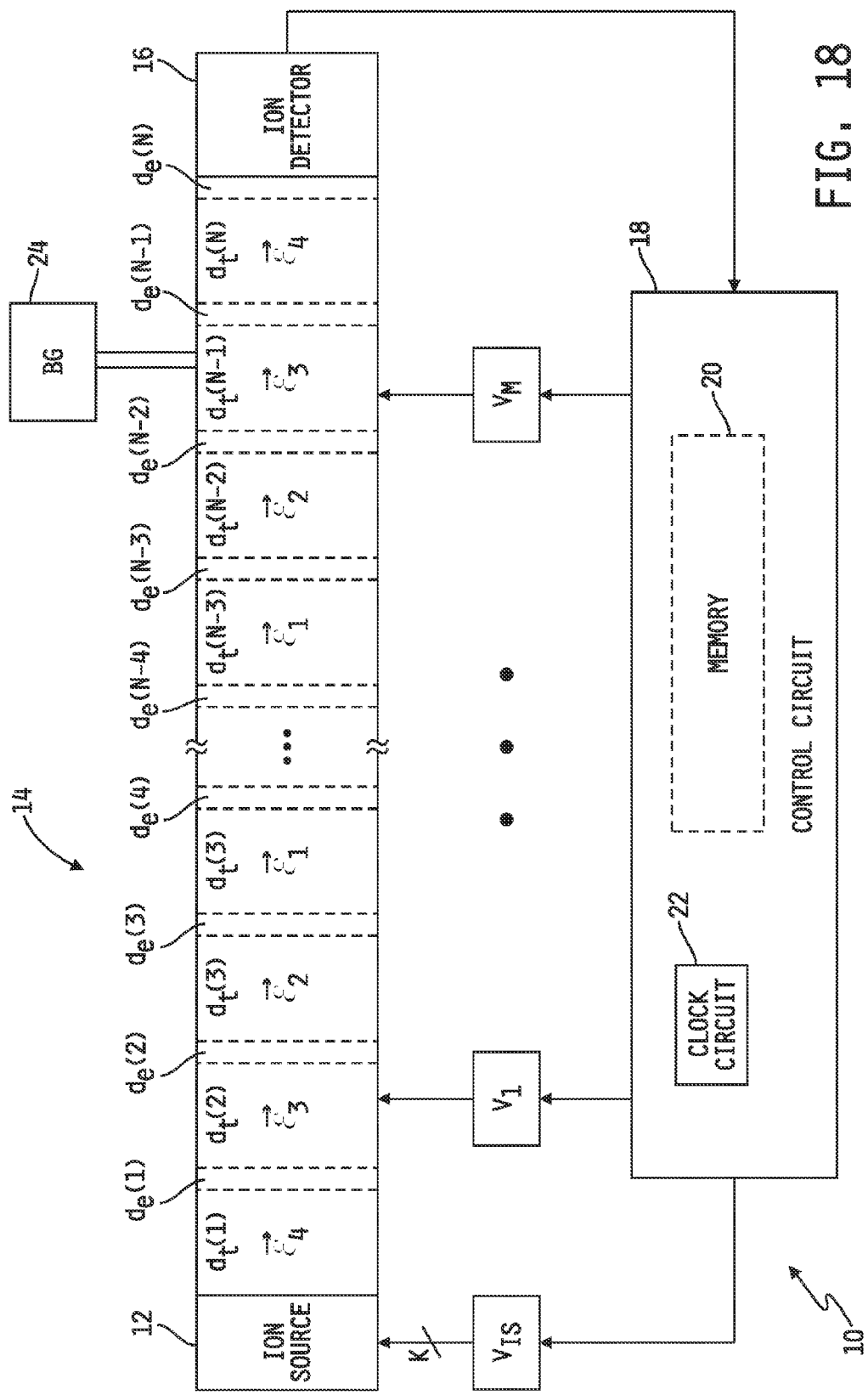
FIG. 18 is a block diagram of the ion mobility spectrometer of FIG. 1 illustrating one illustrative technique controlling electric fields within some of the drift tube segments adjacent to the ion entrance and ion exit ends when operating a linear drift tube ion mobility spectrometer to direct ions back and forth between the two ends of the drift tube in a manner that resolves only ions having a selected mobility or range of mobilities.

Referring now to FIG. 18, the ion mobility spectrometer 10 of FIG. 1 is shown alternatively configured to randomize ion positions during each such pass of ions. In particular, the instructions stored in the memory 20 include, in the embodiment illustrated in FIG. 18, instructions that are executable by the control circuit 18 to control the strengths, i.e., the magnitudes, of the electric fields established by the electric field activation sources, $V_1$-$V_M$, in a number of adjacent drift tube segments. More specifically, the electric fields in a number of adjacent drift tube segments are progressively diminished to cause the ions to randomize their positions relative to the drift tube 14 by bunching up in one or more of the number of adjacent drift tube segments. In the embodiment illustrated in FIG. 18, for example, the control circuit 18 is configured to control the electric field activation sources, $V_1$-$V_M$, to cause the magnitudes of the electric fields $E_1$-$E_4$ in the four adjacent drift tube segments at each end of the drift tube to diminish such that $E_1 > E_2 > E_3 > E_4$. In alternative embodiments, the number of adjacent drift tube segments in which the electric fields are diminished in magnitude may be more or fewer, may comprise any number of such adjacent drift tube segments at either or both ends of the drift tube 14, or may comprise any number of such adjacent drift tube segments between the two ends of the drift tube 14.

Figure 19:
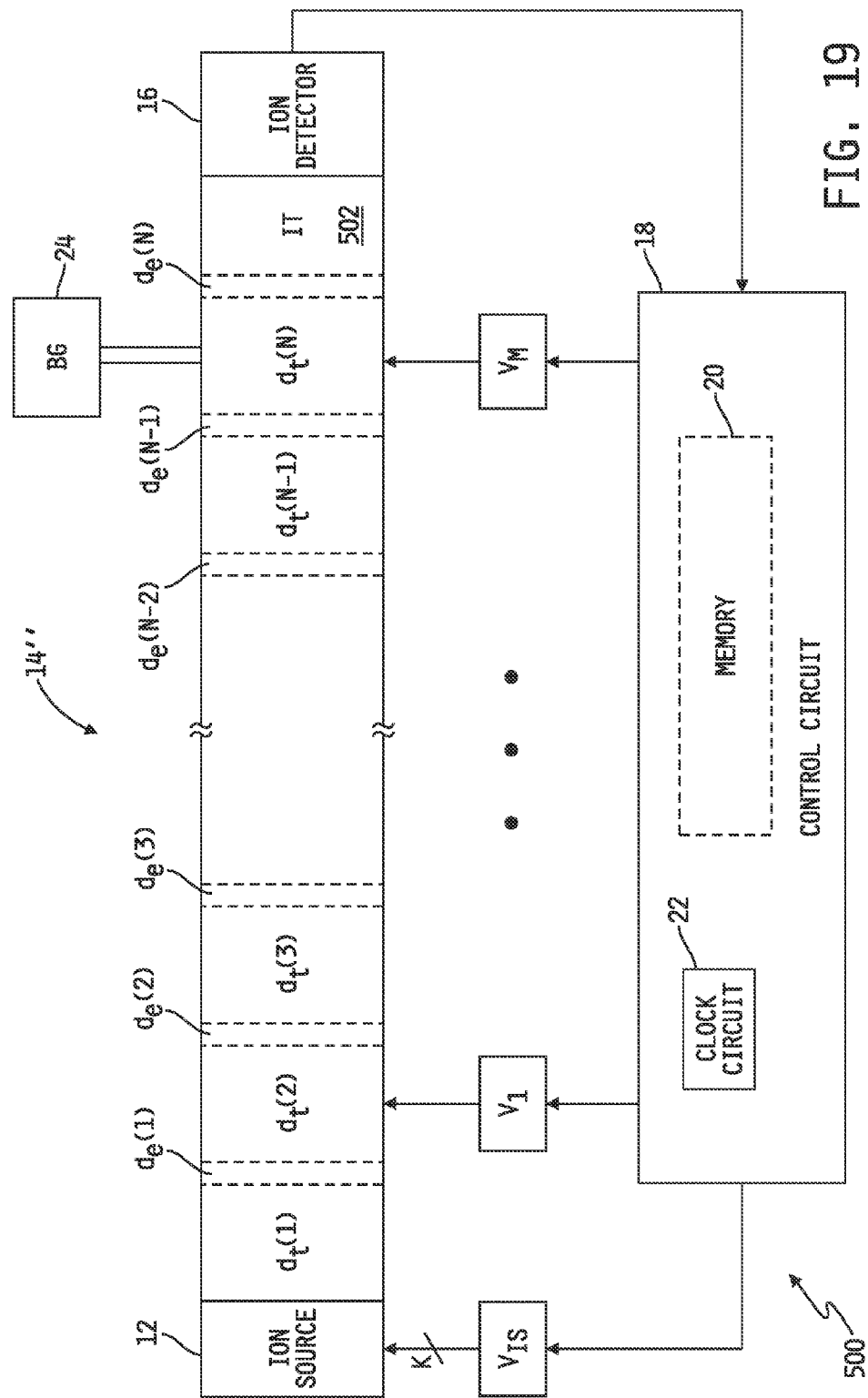
FIG. 19 is a block diagram of yet another illustrative embodiment of an ion mobility spectrometer instrument.

The back-and-forth mobility separation in the segmented drift tube as just describe with respect to FIGS. 17 and 18 may alternatively or additionally be used for OMS modes of operation as described hereinabove with respect to FIG. 7. This allows the use of overtone frequencies as a means of mobility selection. Additionally, such a device could incorporate ion trapping on either end to allow for selective enrichment of a mobility region prior to mobility selection refinement with the back-and-forth cycling of ions. Here, ions from a continuous or pulsed source can pass through a linear drift tube in either direction and those with resonant frequencies can be trapped in an ion trap positioned in the drift tube. After selective filling for a predetermined time period, i.e., as described hereinabove with respect to FIGS. 16A-16L, the ions would then be cycled back-and-forth through the linear drift tube a number of times to obtain greater resolution (isolation of ions of a given mobility). Referring to FIG. 19, one illustrative embodiment of such an ion mobility spectrometer 500 is shown in which an ion trap 502 is positioned at the end of the linear drift tube 14", which is otherwise identical to the drift tube 14 of FIGS. 1-4. The remaining components of the spectrometer 500 are likewise identical to like-numbered components of the spectrometer 10 of FIGS. 1-4 except that the memory includes instructions stored therein that are executable by the control circuit 18 to control and operate the spectrometer 500 to selectively fill the drift tube 14" for a predefined time period or number of back and forth cycles, and to thereafter cycle the ions back and forth a desired number of times as generally described hereinabove with respect to FIGS. 15-16L.

Figure 20:
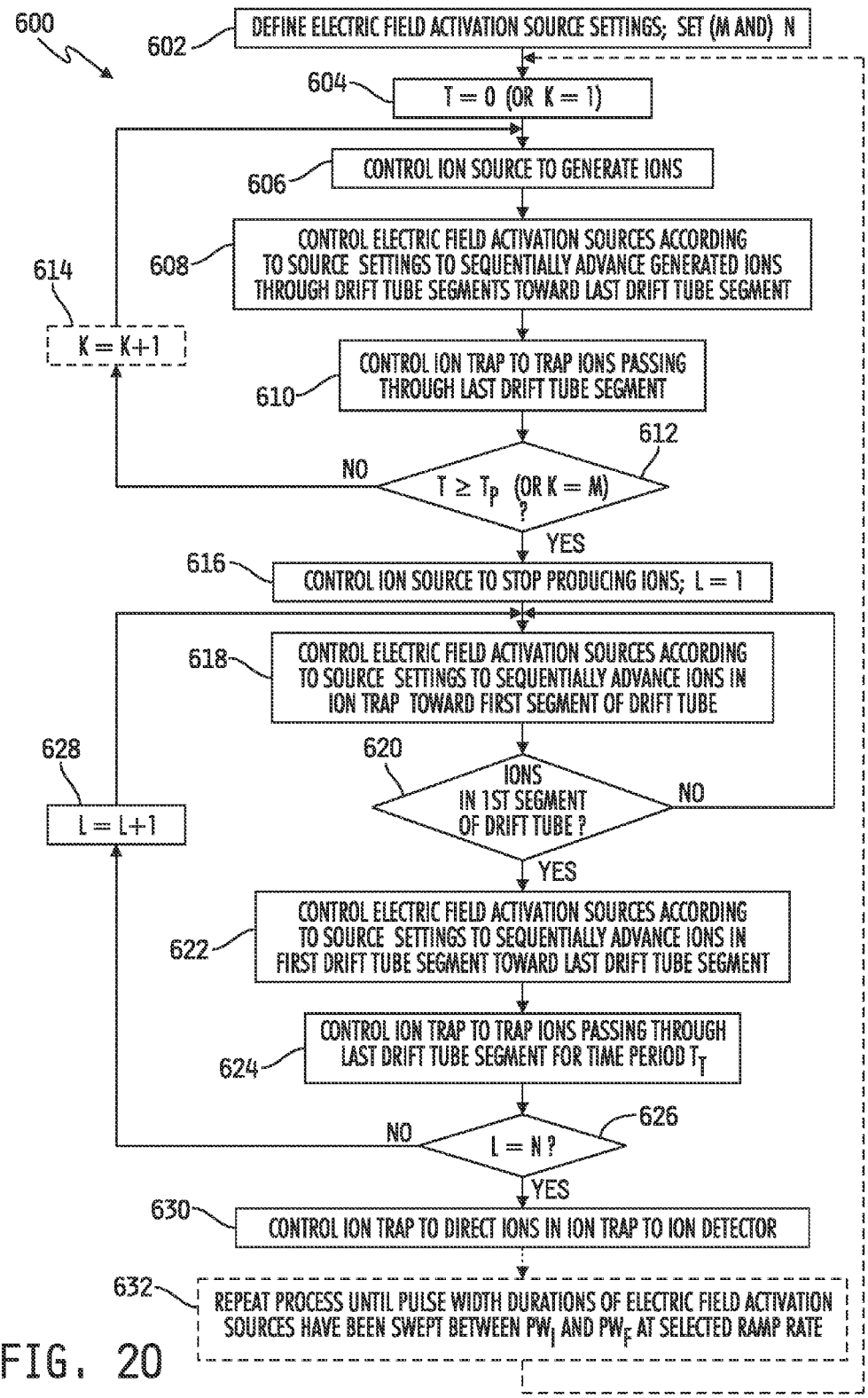
FIG. 20 is a flowchart of one illustrative process for operating the ion mobility spectrometer of FIG. 19 by sequentially controlling the electric field activation sources to direct ions back and forth between the ends of the drift tube in a manner that resolves only ions having a selected mobility or range of mobilities.

Referring now to FIG. 20, a flowchart is shown of one illustrative embodiment of a process 600 for operating the linear drift tube 14" of FIG. 19 as just described. Illustratively, the process 600 is stored in the memory 20 of the control circuit 18 in the form of instructions that are executable by the processor 18 to control operation of the spectrometer 500. The process 600 begins at step 602 where the operational settings of the number, M, of electric field activation sources are defined, and a value of an integer, N, (and optionally M) is set. In embodiments in which the spectrometer 500 will be operated to produce ions having a mobility or range of mobilities that is/are resonant with only a fundamental frequency, $f_F$, of operation of the electric field activation sources, $V_1$-$V_M$, step 602 may include, for example, the steps 82-88 of the process 80 of FIG. 5. In other embodiments in which the spectrometer 500 will be operated to produce ions having ion mobilities resonant with one or more overtones, e.g., harmonic frequencies, of operation of the electric field activation sources, $V_1$-$V_M$, step 602 may include, for example, the steps 102-106 of the process 100 of FIG. 7.

Following step 602, the process 600 advances to step 604 where the control circuit 18 is operable in one embodiment to reset a timer, e.g., set a timer value, T, to zero (or to another arbitrary value), and in an alternate embodiment to set a counter value, K, equal to 1. Thereafter at step 606, the control circuit 18 is operable to control the ion source 12 to generate ions, and thereafter at step 608 the control circuit 18 is operable to control the electric field activation sources, $V_1$-$V_M$, according to the source settings determined at step 602 to sequentially advance ions sequentially through the drift tube segments toward the last drift tube segment, i.e., toward the ion trap 502. The ions advance through the drift tube at step 608 will, of course, have ion mobilities or ranges of ion mobilities that are resonant with the activation time, i.e., time duration of activation, of the electric field activation sources $V_1$-$V_M$ as illustrated and described hereinabove. Thereafter at step 610, the control circuit 18 is operable to control the ion trap 502 to trap ions advanced through the drift tube 14" to the ion trap 502. Thereafter at step 612, the control circuit 18 is operable to determine whether the timer has reached a predefined time period, $T_P$, since being reset, or to determine whether the value of the counter, K, has reached the value M which was optionally set at step 602. In some embodiments, the ion source 12 is controlled at step 606 to continuously generate ions, and in other embodiments the ion source 12 is controlled at step 606 to generate discrete packets or pulses of ions. In either case, a timer or a counter may be used to control the amount of time that ions are collected in the ion trap 502 or the number of passes in which ions are advanced into the ion trap via the drift tube 14". If a timer is used, step 612 loops back to step 606 (or to step 608 in the case of continuous generation of ions) until $T > T_P$. If a counter is used, step 612 advances to step 614 to increment K, and to then loop back to step 606 (or to step 608 in the case of continuous generation of ions) until K=M, where M=the number of times ions are advanced through the drift tube 14" into the ion trap 502. In either case, the "YES" branch of step 612 advances to step 616 where the control circuit 18 is operable to stop producing ions and to set a counter value, L, equal to 1.

Following step 616, the process 600 advances to step 618 where the control circuit 18 controls the ion trap 502 and the electric field activation sources, $V_1$-$V_M$, to according to source settings, e.g., those determined at step 602, to sequentially advance ions in the ion trap 502 in a reverse direction toward the first drift segment of the drift tube 14", i.e., to the $d_t(1)$. When the ions are determined at step 620 by the control circuit 18 to be in the first drift tube segment (e.g., as a function of time after being released from the ion trap 502 at step 618), the process advances to step 622, and otherwise loops back to step 618 until step 620 is satisfied. At step 622, the control circuit 18 controls the electric field activation sources, $V_1$-$V_M$, to according to source settings, e.g., those determined at step 602, to sequentially advance ions in the ion trap 502 in a forward direction from the first drift tube segment, $d_t(1)$ toward last drift tube segment, i.e., the ion trap 502. Thereafter at step 624, the control circuit 18 is operable to control the ion trap 502 to trap therein ions passing through the last drift tube segment for a time period, $T_T$, where $T_T$ is a trapping time period that allows the ions to randomize as described hereinabove with respect to FIG. 17. Thereafter at step 626, the control circuit 18 is operable to determine whether the counter, L, is equal to the number N. If not, the process 600 advances to step 628 where the counter, L, is incremented by 1 and the process 600 then loops back to again execute step 618. If, at step 626, the control circuit 18 determines that L=N, then the ions have traversed the linear drift tube 14" the desired number of times, and the process 600 advances to step 630 where the control circuit 18 is operable to control the ion trap 502 to direct ions trapped therein to the ion detector 16. Optionally, the process 600 may include an extra step 632, executed following step 630, in which the control circuit 18 is operable to execute steps 604-630 until the pulse width durations, i.e., the "time durations" of activations of the electric field activation sources, $V_1$-$V_M$, have been swept through a range of pulse width durations between an initial pulse width duration, $PW_I$ and a final pulse width duration, $PW_F$. In embodiments which include step 632, step 602 will of course include a determination of $PW_I$ and $PW_F$ as illustrated in the process 100 of FIG. 7. Generally, $PW_I$ and $PW_F$ will be selected to produce one or more overtones, i.e., harmonic frequencies of which the predefined ion mobilities or range of ion mobilities are resonant, and/or to produce ions that have ion mobilities resonant with fundamental frequencies of the activation frequencies or pulse rates, i.e., activation times, of the electric field activation sources, $V_1$-$V_M$, for each of the discrete activation frequencies or pulse rates over and between $PW_I$ and $PW_F$, as described hereinabove.

While the spectrometer 500 illustrated in FIG. 19 is illustrated with the ion trap 502 located at one end of the drift tube 14", it will be understood that the ion trap 502 may alternatively be positioned at the opposite end of the drift tube 14" or between the two ends of the drift tube 14". Alternatively or additionally, any number of ion traps may be positioned in the drift tube 14", e.g., one at each end, for the purpose of trapping and randomizing positions of the ions trapped therein as illustrated and described with respect to FIG. 17, and/or the magnitudes of the electric fields of a number of adjacent ones of the drift tube segments may be sequentially diminished to enhance or achieve this result as illustrated and described with respect to FIG. 18. In such case or cases, the ion trap 502 may, need not, be controlled in as described for the purpose of randomizing ions trapped therein.

In any of the linear or cyclotron configurations of the ion mobility spectrometer illustrated and described herein, a non-destructive detector, e.g., rather than an ion counting detector 16, could be used that is configured to measure the image charge many times at a specified position within drift tube. Ion distributions could then be recorded as the frequency that ions pass the non-destructive detector. A conventional frequency transformation, e.g., Fourier transform, could then be used to back-calculate ion mobility.

Figure 21:
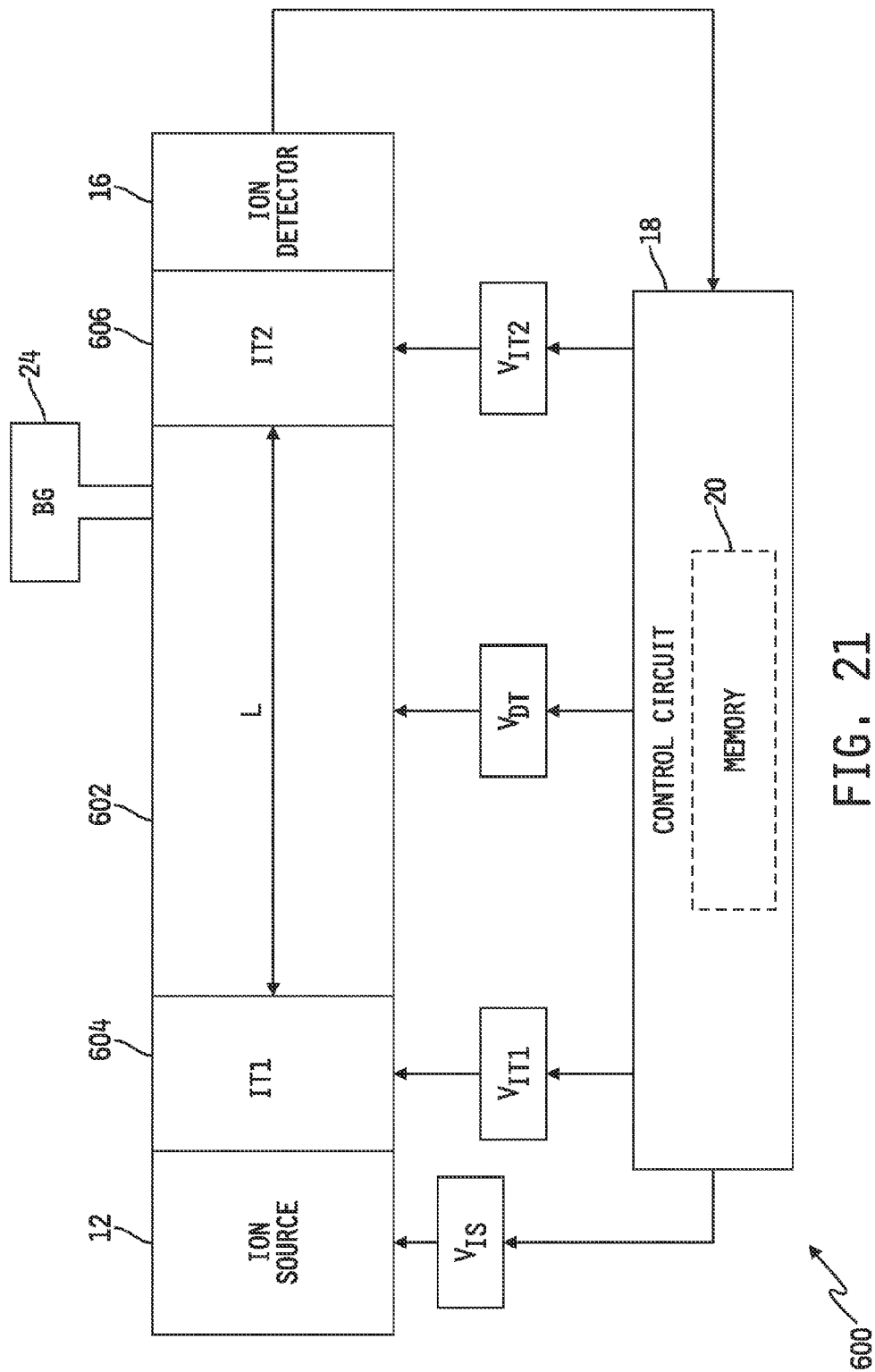
FIG. 21 is a block diagram of still another illustrative embodiment of an ion mobility spectrometer.

Referring now to FIG. 21, yet another embodiment of an ion mobility spectrometer 600 is shown. In the illustrated embodiment, some of the illustrated components are identical to those described hereinabove, and like reference numbers are therefore used to identify like components. In FIG. 21, the drift tube 602 includes a single drift tube segment of length L positioned between two ion traps 604 and 606. The ion trap 604 is positioned adjacent to the inlet of the single drift tube segment 602, and the ion trap 606 is positioned adjacent to the ion outlet of the single drift tube segment 602. At least one drift tube voltage source, $V_{DT}$, is electrically connected between the control circuit 18 and the single drift tube segment 602, and is controllable in a conventional manner to establish an electric field in the single drift tube region 602 in one direction that causes ions supplied by the ion source 12 to drift from the ion trap 604 toward the ion trap 606, and to alternatively establish an electric drift field in the single drift tube region 602 in an opposite direction that causes ions to drift from the ion trap 606 toward the ion trap 604. An ion trap voltage source, $V_{IT1}$, is electrically connected between the control circuit 18 and the ion trap 604, and another ion trap voltage source, $V_{IT2}$, is electrically connected between the control circuit 18 and the ion trap 606.

The memory 20 illustratively includes instructions stored therein that are executable by the control circuit 18 to execute a process a predefined number of times. The process illustratively includes activating the at least one electric field activation source, $V_{DT}$, for a time duration to establish an electric field in the one direction to cause only ions supplied by the ion source 12 that have a predefined ion mobility or range of ion mobilities defined by the time duration to travel through the single drift tube region 602 in the direction from the ion trap 604 toward the second ion trap 606 followed by controlling the ion trap 606 to trap therein the ions that have the predefined ion mobility or range of ion mobilities. The ion trap 606 is then controlled to release the ions trapped therein and the control circuit 18 then activates the at least one electric field activation source, $V_{DT}$, for the time duration to establish an electric field in the opposite direction to cause only ions that have the predefined ion mobility or range of ion mobilities defined by the time duration to travel through the single drift tube region 602 in the direction from the ion trap 606 toward the ion trap 604 followed by controlling the ion trap 604 to trap therein the ions that have the predefined ion mobility or range of ion mobilities followed by controlling the ion trap 604 to release the ions trapped therein. This process may be performed any number of times to thereby cause ions to traverse the single drift tube region 602 any such number of times. The control circuit 18 may then control the ion trap 606 to release ions trapped therein toward the ion detector 16 and to process the ion detection signals produced by the ion detector to determine ion mobility spectral information therefrom. The ion source 12 may be controlled in a pulsed fashion to produce discrete packets of ions or may alternatively be controlled to continuously produce ions. The instructions stored in the memory 20 may further include instructions executable by the control circuit 18 to control the ion traps 604 and 606 to trap ions therein for a trap period. The trap period is illustratively selected to allow ions trapped within the ion trap 604 and within the ion trap 606 to randomize their positions relative to the respective ion trap 604/606.

The spectrometer 600 may alternatively be operated in the OMS mode illustrated and described hereinabove. For example, the instructions stored in the memory 20 may further include instructions executable by the control circuit 18 to control the at least one electric field activation source, $V_{DT}$, to sweep the time duration between first and second predefined time durations to thereby cause ions that have fundamental frequencies resonant with each of a number of discrete time durations between the first and second time durations to travel through the single drift tube region 602, and to execute the process the predefined number of times for each of the number of discrete time durations between the first and second predefined time durations.

Figure 13:
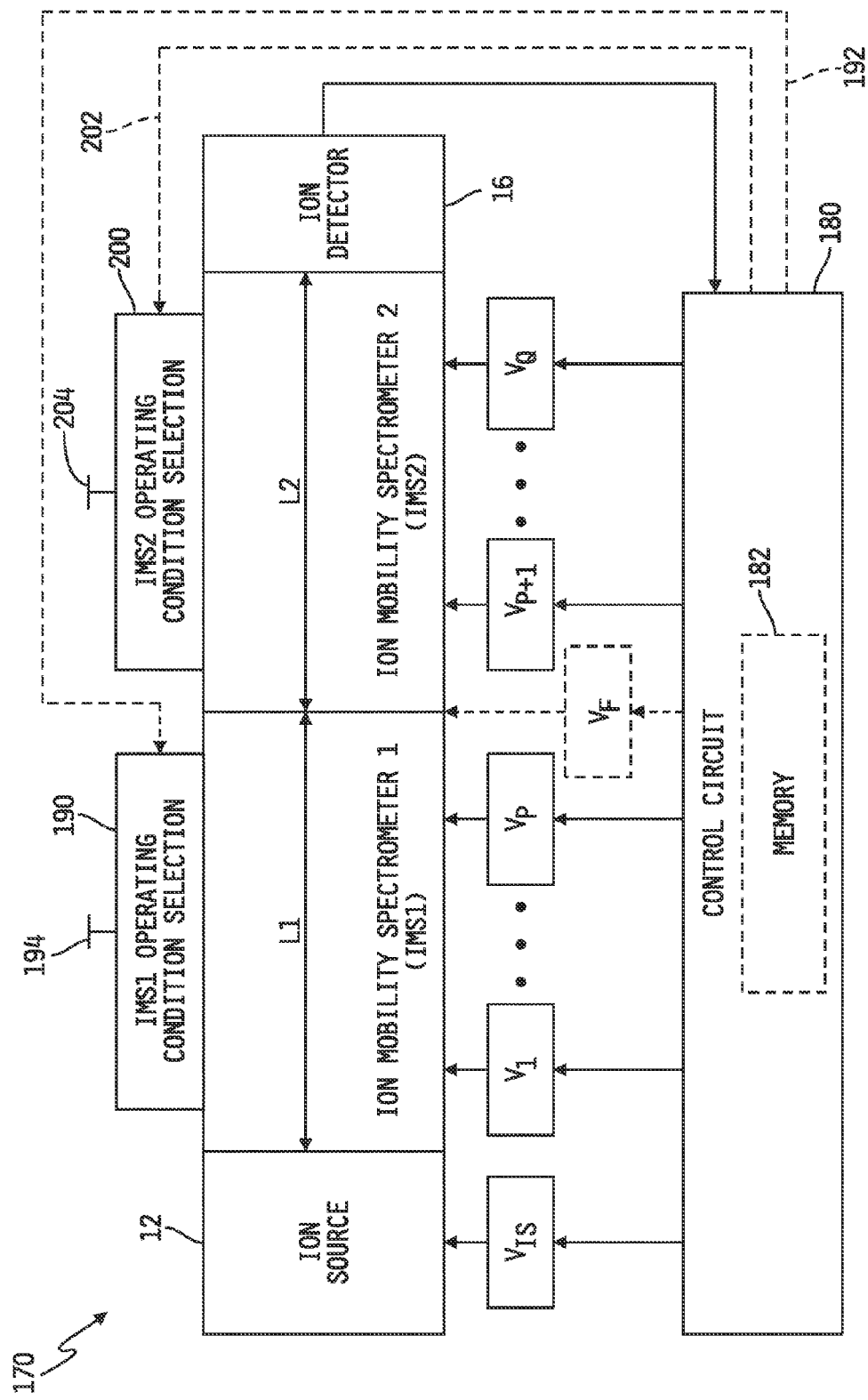
FIG. 13 is a block diagram of one illustrative embodiment of a cascaded ion mobility spectrometer instrument that employs some of the concepts illustrated and described with respect to FIGS. 1-12B.

Referring now to FIG. 13, a block diagram of one illustrative embodiment of a cascaded ion mobility spectrometer instrument 170 is shown that employs some of the concepts illustrated and described hereinabove with respect to FIGS. 1-12B. In the illustrated embodiment, the instrument 170 includes an ion source 12 having an ion outlet coupled to an ion inlet of a first ion mobility spectrometer (IMS1). An ion outlet of IMS1 is coupled to an ion inlet of a second ion mobility spectrometer (IMS2) having an ion outlet that is coupled to an ion detector 16. The IMS1 has an axial length of L1 and the IMS2 has an axial length of L2. A control circuit 180 includes a memory unit 182, and is electrically connected to a control input of an ion source voltage supply, $V_{IS}$, having an output that is electrically connected to the ion source 12. The instrument 170 further includes a plurality of electric field activation sources, $V_1$-$V_Q$, that are electrically connected between the control circuit 180 and IMS1 and IMS2, where Q may be any integer greater than 1. Illustratively, a subset of the electric field activation sources, $V_1$-$V_P$, are dedicated to IMS1, and another subset, $V_{P+1}$-$V_Q$ are dedicated to IMS2. Alternatively, $V_{P+1}$-$V_Q$ may be omitted, and $V_1$-$V_P$ may be used for both of IMS1 and IMS2. In any case, each of the foregoing components may be as described hereinabove with respect to the embodiment of FIG. 1. In one illustrative embodiment, the instrument 170 is operable just as described hereinabove with respect to any of FIGS. 1-12B, except that the ions are resolved over an effective drift tube length of L1+L2 rather than over the length of a single drift tube, such that IMS1 and IMS2 together form a single ion mobility spectrometer.

The ion mobility spectrometer instrument 170 of FIG. 13 may further include at least one additional voltage source, $V_F$, which may be controlled by the control circuit 180 to produce one or more voltages that control one or more ion fragmentation units or other conventional device for inducing structural changes in ions within IMS1, IMS2 and/or positioned between IMS1 and IMS2. In embodiments in which the drift tubes of IMS1 and IMS2 are constructed according to the teachings of co-pending U.S. Patent Application Pub. No. US 2007/0114382, for example, an ion activation region of the type described therein may be positioned at the end of any one or more ion funnels that form IMS1 and/or IMS2. Alternatively, IMS1 and/or IMS2 may be modified in other embodiments to include one or more conventional structural change inducing devices or stages, e.g., one or more ion fragmentation stages, ion conformational change stages, and/or other conventional structural change inducing devices or stages, therein or interposed between IMS1 and IMS2. For example, such a structural change inducing device may be positioned between IMS1 and IMS2, and the ion mobility spectrometer 170 may be operated as described hereinabove to conduct fundamental frequency and/or overtone frequency analysis with IMS1, to then induce structural changes in ions emerging from IMS1, and to then conduct fundamental frequency and/or overtone frequency analysis with IMS2 on the ions in which structural changes were induced. Alternatively or additionally, the fragmented ions may be mobility filtered in a conventional manner prior to entering IMS2. Alternatively or additionally still, such fragmented and mobility-selected ions may be further fragmented and possibly further mobility selected any number of times prior to entrance into IMS2.

IMS1 may further include an operating condition selection unit 190, and IMS2 may likewise include an operating condition selection unit 200. The operating condition selection units 190 and 200 may be manually controlled via respective manual controls 194 and 204, and/or may be automatically controlled by the control circuit 180 via suitable electrical control lines 192 and 202 respectively. The operating condition selection units 190 and 200 are block diagram components that may represent conventional structures that control any one or more of the operating temperature of IMS1 and/or IMS2, the operating pressure of IMS1 and/or IMS2, the chemical make up and/or flow rate of gas, e.g., buffer gas, supplied to the ion pathway of IMS1 and/or IMS2, and the like. In the operation of the ion mobility spectrometer instrument 170, such as described hereinabove, IMS1 and IMS2 may be operated as described hereinabove and further with any one or more of, or with any combination of, the same or different drift tube lengths, L1 and L2, the same or different electrical field strengths applied by the electric field activation sources $V_1$-$V_Q$, the same or different pulse shapes applied by the electric field activation sources $V_1$-$V_Q$, the same or different pulse width durations, PW, applied by the electric field activation sources $V_1$-$V_Q$, the same or different operating temperatures (e.g., T1 for IMS1 and T2 for IMS2), the same or different operating pressures, (e.g., P1 for IMS1 and P2 for IMS2), with the ions passing through IMS1 and IMS2 exposed to the same or different gasses (Gas1 for IMS1 and Gas2 for IMS2), or with ion fragmentation occurring within or between IMS1 and IMS2. Further details relating to some of these operational scenarios or modes are provided in U.S. Pat. No. 7,077,904, the disclosure of which is incorporated herein by reference.

It will be understood that the ion mobility spectrometer instrument illustrated in FIG. 13 and described herein represents only an example multiple drift tube instrument, and that the instrument may alternatively include any number of IMS units or drift tubes. Alternatively still, the IMS drift tubes in such an arrangement need not be linear, and the instrument 170 illustrated in FIG. 13 may include any number of non-linear IMS drift tube, such as two or more circular drift tubes of the type described in co-pending PCT Publication No. WO 2008/028159 A2, filed Aug. 1, 2007, the disclosure of which has been incorporated herein by reference.

Transmission of ions through the various drift tube segments $S_1$-$S_N$ of any of the ion mobility spectrometer instruments described above, by sequentially activating the electric field activation sources $V_1$-$V_M$, is possible only if the mobilities of the ions are in resonance with the switching rates of the electric fields applied by these electric field activation sources. This is true regardless of the phase, $\phi$, of the spectrometer, which refers to the number of electric field activation sources, arranged and connected to the various drift tube segments and ion elimination regions as described above (see e.g., FIGS. 4A-4D). Thus, to transmit ions sequentially through the various drift tube segments $S_1$-$S_N$ as just described, the ions must have mobilities that allow traversal of exactly one drift tube segment in one field application duration. Ions with mobilities that are off resonance either traversing a drift tube segment too quickly or too slowly are eventually eliminated in one of the ion elimination regions $d_e$. In the operation of any of the ion mobility spectrometers illustrated and described above, the switching rates of each of the electric field activation sources, $V_1$-$V_M$, have been equal, and the frequency at which the various electric field activation sources are switched on/off, i.e., the frequency at which the ions have resonant mobilities, is termed the fundamental frequency, $f_f$.

As also described in detail above, such operation of the electric field activation sources $V_1$-$V_M$ has led to a technique referred to as Overtone Mobility Spectrometry (OMS) because of its ability to selectively transmit ions in different frequency regions, including those associated with higher overtones. And for any given phase, $\phi$, such overtones in embodiments of the ion mobility spectrometer illustrated and described herein that are operated with uniform, constant electric fields in the various drift tube segments, $S_1$-$S_N$, are predictably given by the equation $H=\phi(h-1)+1$, $h=1, 2, 3, \ldots$, where H is a harmonic number, $\phi$ is the phase of the ion mobility spectrometer 10, and h is an integer index. Thus, it was demonstrated above that for a 2-phase, system, $H=1, 3, 5, 7, \ldots$, for a 3-phase system, $H=1, 4, 7, 10, \ldots$, for a 4-phase system, $H=1, 5, 9, 13, \ldots$, etc.

However, whereas resolving power increases with increasing overtone, overlap of ions from flanking frequency regions tends to limit the overall peak capacity with higher overtones. This limitation can be overcome with an attendant increase in peak capacity by modifying the OMS techniques described above to cause at least one of the electric field activation sources to have a different activation time duration than activation time durations of others of the electric field activation sources. As will be described in detail below, this technique can be used to select sub-species of OMS peaks, i.e., selected overtones, while filtering out others, and may therefore be referred to as Selected Overtone Mobility Spectrometry (SOMS). As will also be described in detail below, SOMS can also be used to select and observe previously unobserved integer overtones as well as non-integer overtones. These concepts will be introduced below with reference to 2-phase arrangements ($\phi=2$) of the type illustrated and described above, and will then be extended or generalized to systems with $\phi>2$. It should be understood, however, that the various SOMS concepts and technique described below may be implemented with any of the various ion mobility spectrometer configurations illustrated and described above, including any and all linear and/or circular drift tube arrangements.

Referring now to FIG. 22A, a timing diagram 40 is shown illustrating a series of drift tube segments, $d_t(1), d_t(2), \ldots$, operated with a two-phase arrangement of electric field activation sources having equal activation durations selected to define the $3^{rd}$ overtone of the fundamental frequency of operation as described above with respect to OMS operation. The activation durations of the electric field activation source $V_1$ is designated by the letter "A" in FIG. 22A, and corresponds to the shaded squares. The activation durations of the electric field activation source $V_2$, on the other hand, is designated by the letter "B" in FIG. 22A, and corresponds to the white squares. If the time span across one drift tube segment, e.g., $d_t(1)$ is defined as $1/f_f$, then only ions having mobilities resonant with $f_f$ will be transmitted from one drift tube segment to the next. Such ions will also be transmitted at higher overtones of $f_f$, and in a 2-phase system one such overtone is the third overtone, or $3f_f$. It is this operation that is illustrated in FIG. 22A, and it can thus be observed that 3 transitions (e.g., $3f_f$) between $V_1$ and $V_2$ occur in each drift tube segment to illustrate movement of a packet of ions along the drift tube in the $3^{rd}$ overtone. Likewise, a total of 6 equal-duration transitions between $V_1$ and $V_2$ occur between each set of two drift tube segments, e.g., $d_t(1)$ and $d_t(2)$, as the packet of ions move along the drift tube in the $3^{rd}$ overtone as indicated by reference number 700 in FIG. 22A.

Referring now to FIG. 22B, a timing diagram 40' similar to FIG. 22A is shown and illustrates the two-phase arrangement of electric field activation sources having unequal activation durations in each phase, but which are also selected to define the $3^{rd}$ overtone of the fundamental frequency of operation. Between each set of two drift tube segments, e.g., .g., $d_t(1)$ and $d_t(2)$, $V_1$ is activated for only a single shaded square whereas $V_2$ is activated for the next consecutive 5 white squares as indicated by reference number 702 in FIG. 22B. A phase ratio, $\zeta$, is defined as the ratio of the activation duration of an arbitrary one of the electric field activation sources, e.g., $V_2$, and the activation duration of the other electric field activation source, e.g., $V_1$. In the example illustrated in FIG. 22B, the phase ratio, $\zeta$, is thus 5/1, or 5, and in the 2-phase system the $3^{rd}$ overtone is thus defined for $\zeta=5$. It can be similarly shown (although not shown in the figures) that in the 2-phase system the $5^{th}$ overtone is defined for $\zeta=9$. This then leads to the generalized result $m_{eq}=(\zeta+1)/2$, where $m_{eq}$ is the equivalent overtone number for a given phase ratio, and the frequency, $f_{eq}$, at which the equivalent overtone occurs, relative to the fundamental frequency, $f_f$, of the OMS system, is given by the relationship $f_{eq}=M_{eq}f_f$.

In OMS, there is a maximum overtone at which the distance traveled by a packet of ions in a single phase is shorter than the length of an ion elimination region, e.g., $d_e(1)$. As discussed above, an ion packet will be filtered out if it is within an ion elimination region when a repulsive electric field is established within that region, and the maximum overtone is thus given by the relationship $m_{max}=(I_t+I_e)/I_e$, where $I_t$ is the length of each of the drift tube segments $d_t(1)$, $d_t(2)$, . . . , and $I_e$ is the length of the ion elimination regions, $d_e(1)$, $d_e(2)$, . . . .

The same maximum overtone limitation holds true for SOMS, and combining the above equations for $m_{eq}$ and $m_{max}$ yields the following equation for the maximum phase ratio, $\zeta_{max}=[2(I_t+I_e)/I_e]-1$.

As can be seen in FIG. 22B, the duty cycle of the fundamental peak in SOMS is less than that of the equivalent OMS for an overtone greater than one, due to the lack of repeats of the packets within the two drift tube segment distance. This results in a multiplicative loss in duty cycle equivalent to the overtone, which is given by the relationship Duty Cycle=$[(I_t+I_e)-I_e]/2m(I_t+I_e)$.

Figure 23A:
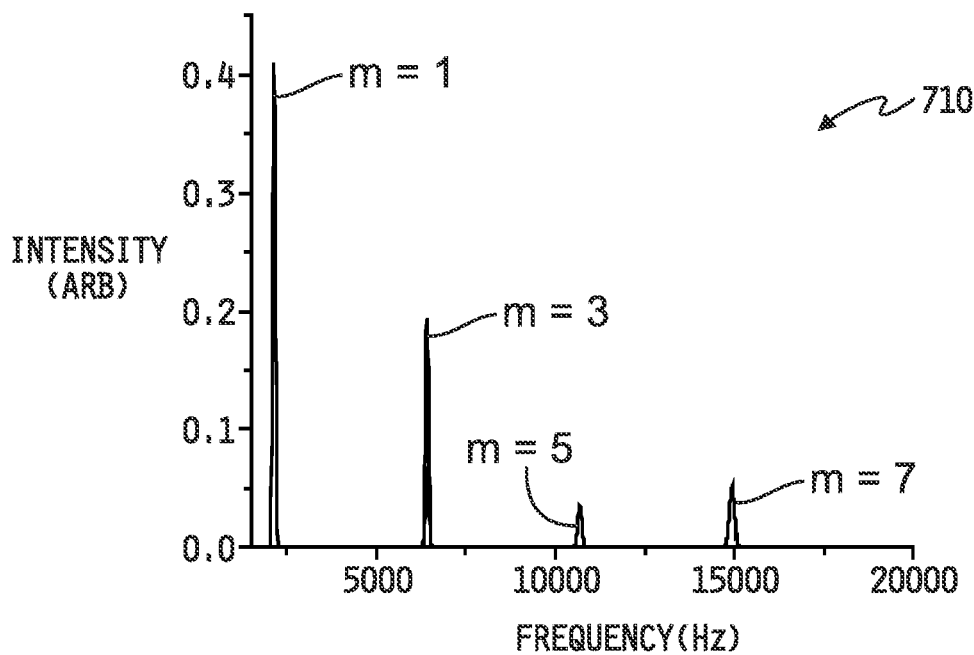
FIG. 23A is a plot of ion intensity vs. frequency illustrating the result in the frequency domain of a simulated spectra in which a phase ratio of activation durations of two electric field activation sources in a two-phase application is set to unity.
Figure 23B:
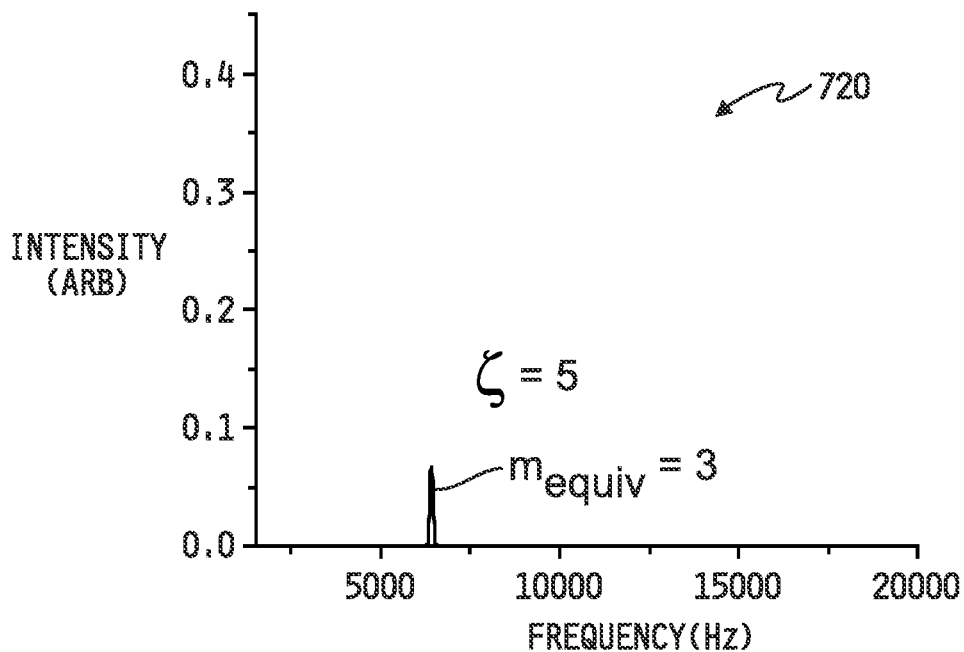
FIG. 23B is a plot of ion intensity vs. frequency illustrating the result in the frequency domain of a simulated spectra in which a phase ratio of activation durations of two electric field activation sources in a two-phase application is set to 5.

The fundamental peak of a SOMS system is the peak at the lowest frequency, and is analogous but not equivalent to the peak at the fundamental frequency in an OMS system. This is because the fundamental peak in a SOMS system is, by definition, an overtone in the OMS system. And just as a 2-phase OMS system has $3^{rd}$, $5^{th}$, $7^{th}$, etc. overtones, so too does a 2-phase SOMS system, wherein each such overtone in the SOMS system has an equivalent overtone, $m_{eq}$ defined by the phase ratio. For example, referring to FIG. 23A, the fundamental peak and the $3^{rd}$, $5^{th}$ and $7^{th}$ overtones are shown for an example simulated spectrum 710 of a SOMS system in which the phase ratio, $\zeta$, is 1. With a phase ratio, $\zeta$, of 1, the SOMS system reduces to the OMS system illustrated and described above, and fundamental peak, as well as the equivalent overtones, $m_{eq}$, are thus identical to the fundamental peak and overtone values of the OMS system, i.e., m=1, m=3, m=5 and m=7. However, as illustrated in FIG. 23B, in a SOMS system having a phase ratio, $\zeta$, of 5, the above equation for the equivalent overtone $m_{eq}$ reveals that the fundamental peak for this SOMS system is equivalent to the $3^{rd}$ overtone in the OMS system. SOMS can thus be used to select overtones for observation while also filtering out other overtones.

Figure 24:
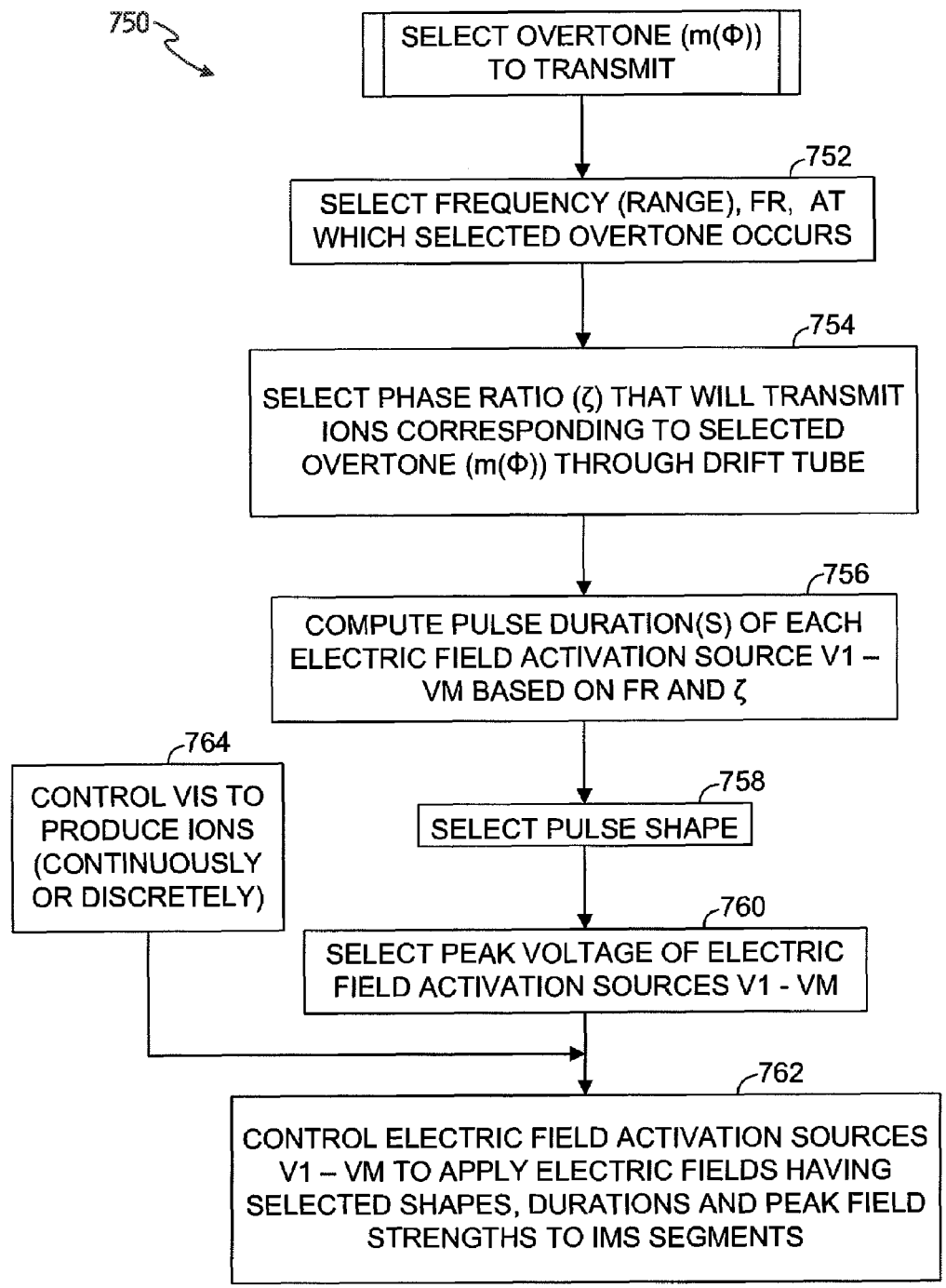
FIG. 24 is a flowchart of a process for operating a two-phase ion mobility spectrometer of the type illustrated and described herein by selecting a phase ratio of the activation durations of the two electric field activation sources to transmit ions through the drift tube at a corresponding selected overtone frequency.

Referring now to FIG. 24, a flowchart is shown of an embodiment of a process 750 for selecting an overtone to transmit through an ion mobility spectrometer using the SOMS technique just described. The process 750 illustrated in FIG. 24 may be provided, in whole or in part, in the form of instructions that are stored in the memory unit 20 of the control circuit 18 and that are executable by the control circuit 18 to control any implementation of an ion mobility spectrometer instrument illustrated and described herein, in accordance with the process 750. In any case, the process 750 begins at step 752 where the frequency or frequency range, FR, at which the selected overtone occurs is selected. Generally, the frequency or frequency range sought at step 752 is the frequency, $f_{eq}$, at which the equivalent overtone occurs relative to the fundamental frequency, $f_f$, of the OMS system, and is given by the relationship $f_{eq}=m_{eq}f_f$. Thus, if the fundamental frequency, $f_f$, is known, then the frequency, $f_{eq}$, at which any selected overtone, $m_{eq}$, occurs is given by this relationship.

The process 750 advances from step 752 to step 754 where the phase ratio, $\zeta$, is selected which will transmit ions corresponding to the selected overtone through the drift tube. In a 2-phase system, the phase ratio that will transmit ions corresponding to the selected overtone through the drift tube is given by the relationship $m_{eq}=(\zeta+1)/2$. Following step 754, the pulse durations of each of the electric field activation sources $V_1$-$V_M$ used in the ion mobility spectrometer instrument are computed at step 756. The pulse durations for each of the electric field activation sources $V_1$-$V_M$ can be determined using well-known equations based on the frequency or frequency range, FR, determined at step 752 and on the phase ratio, $\zeta$, selected at step 754. Thereafter at step 758, the shape of the pulse width is selected, and thereafter at step 760 the peak voltage of the electric field activation sources $V_1$-$V_M$ is selected. The process 750 advances from step 760 to step 762, and simultaneously with step 760 the ion source voltage supply, $V_{IS}$, is controlled at step 764 in a manner that causes the ion source, e.g., the ion source 12, to produce ions. The ions produced at step 764 may be produced continuously or may instead be produced discretely as described hereinabove. In any case, the control circuit 18 is subsequently operable at step 762 to control the electric field activation sources $V_1$-$V_M$, as described hereinabove, to sequentially apply electric fields having the selected shapes, durations and peak field strengths to the various drift tube segments, $S_1$-$S_N$ as described hereinabove by example with reference to FIGS. 2-4D. Steps 760 and 762 may be repeated continuously or a finite number of times to thereby operate the ion mobility spectrometer instrument as a continuous or discrete ion mobility filter. It will be understood that steps 752-764 are not required to be executed in the illustrated order, and that one or more of these steps may alternatively be interchanged with one or more other of these steps.

Figure 25:
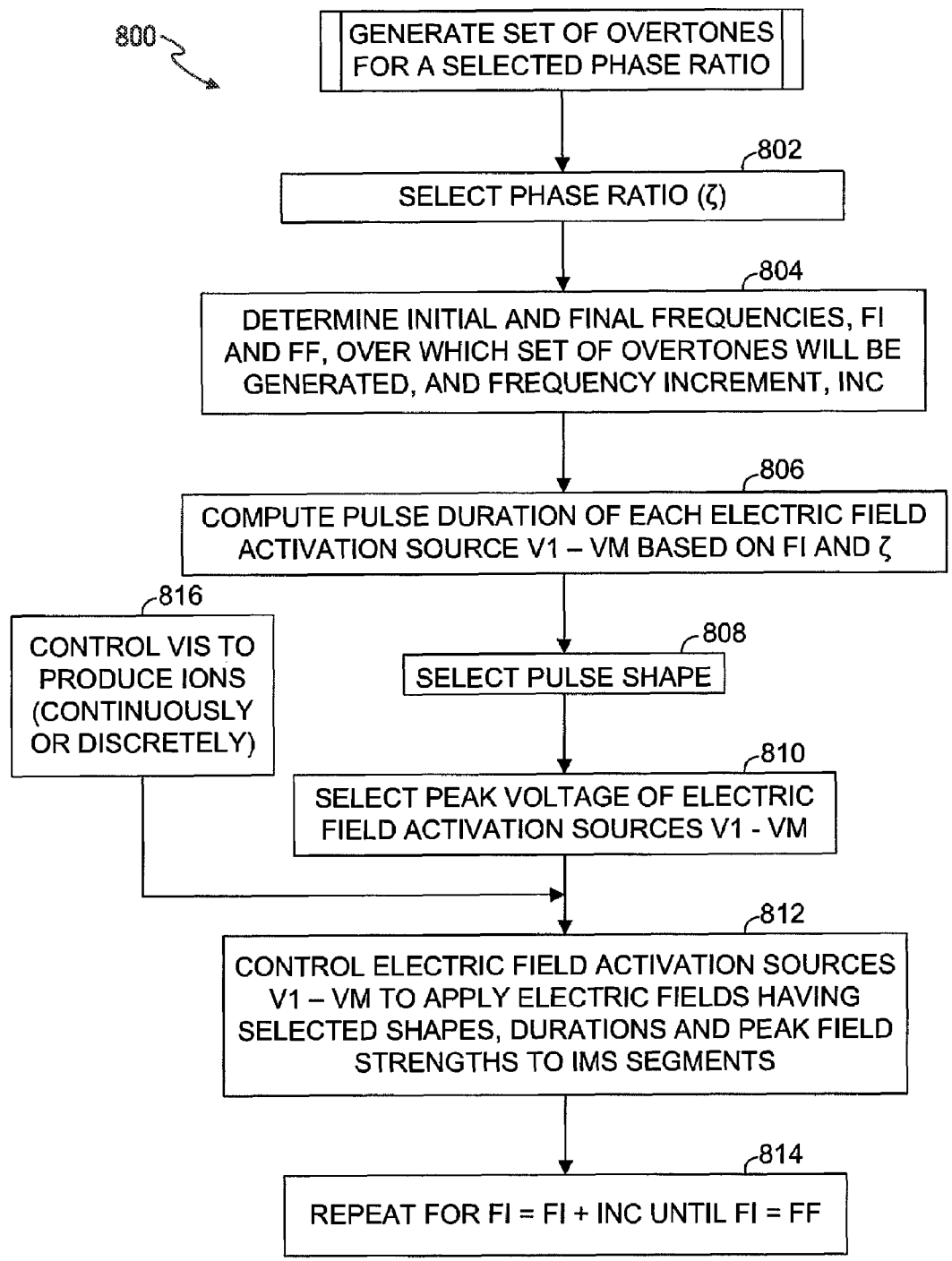
FIG. 25 is a flowchart of a process for operating a two-phase ion mobility spectrometer of the type illustrated and described herein by selecting a phase ratio of the activation durations of the two electric field activation sources and sweeping the two activation durations over a range of frequencies to transmit ions through the drift tube at a corresponding set of overtone frequencies.

Referring now to FIG. 25, a flowchart of an illustrative process 800 for generating a set of overtones for a selected phase ratio, $\zeta$. The process 800 illustrated in FIG. 25 may be provided, in whole or in part, in the form of instructions that are stored in the memory unit 20 of the control circuit 18 and that are executable by the control circuit 18 to control an ion mobility spectrometer instrument, e.g., of the type illustrated and described herein, in accordance with the process 800. The process 800 begins at step 802 where the phase ratio, $\zeta$, is selected. Thereafter at step 804, initial and final frequencies, FI and FF, over which a set of overtones corresponding to the selected phase ratio, $\zeta$, will be generated, and a frequency increment, INC, is also selected. Illustratively, the initial frequency, FI, may be selected to produce an electrical field activation duration that is slightly longer than necessary to produce the fundamental ion intensity peak for the SOMS system so that the resulting ion intensity vs. frequency spectrum begins approximately at this fundamental peak. As in the process 750, this initial frequency, FI, is the frequency, $f_{eq}$, at which the equivalent overtone occurs relative to the fundamental frequency, $f_f$, of the OMS system, and is given by the relationship $f_{eq}=m_{eq}f_f$, where $m_{eq}$ can be determined from the selected phase ratio, ζ, according to the relationship $m_{eq}=(ζ+1)/2$. Illustratively, the final frequency, FF, may be selected to be a frequency beyond which no useful information is expected to occur, or beyond which no ion intensity information is sought. In any case, the frequency increment, INC, will typically be selected to provide desired a frequency resolution.

Following step 804, the pulse durations of each of the electric field activation sources $V_1$-$V_M$ used in the ion mobility spectrometer instrument are computed at step 806. The pulse durations for each of the electric field activation sources $V_1$-$V_M$ can be determined using well-known equations based on the initial frequency, FI, determined at step 804 and on the phase ratio, ζ, selected at step 802. Thereafter at step 808, the shape of the pulse width is selected, and thereafter at step 810 the peak voltage of the electric field activation sources $V_1$-$V_M$ is selected. The process 800 advances from step 810 to step 812, and simultaneously with step 810 the ion source voltage supply, $V_{IS}$, is controlled at step 816 in a manner that causes the ion source, e.g., the ion source 12, to produce ions. The ions produced at step 816 may be produced continuously or may instead be produced discretely as described hereinabove. In any case, the control circuit 18 is subsequently operable at step 812 to control the electric field activation sources $V_1$-$V_M$, as described hereinabove, to sequentially apply electric fields having the selected shapes, durations and peak field strengths to the various drift tube segments, $S_1$-$S_N$ as described hereinabove by example with reference to FIGS. 2-4D. Thereafter at step 814, the steps 802-812 are repeated for FI=FI+INC until the steps 802-812 are executed for the final frequency, FF. It will be understood that steps 802-816 are not required to be executed in the illustrated order, and that one or more of these steps may alternatively be interchanged with one or more other of these steps.

Figure 26A:
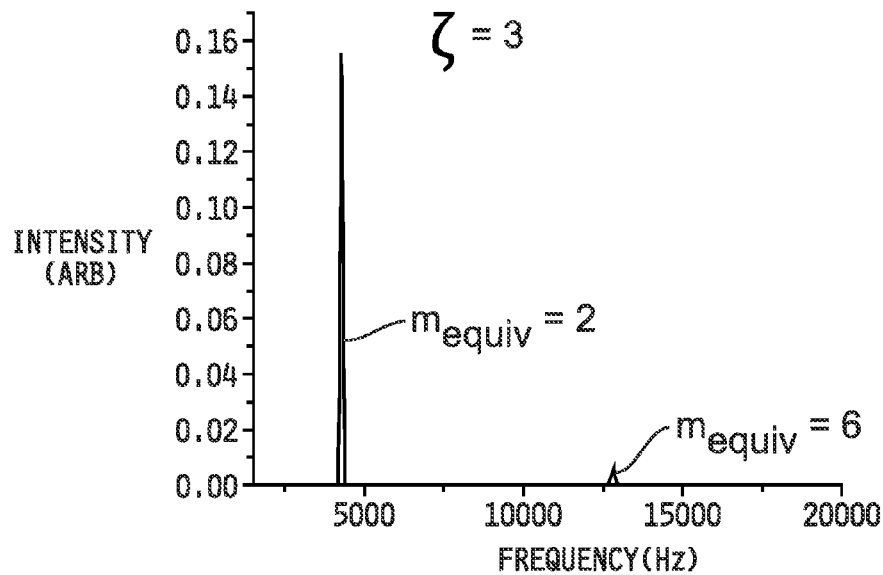
FIG. 26A is a plot of ion intensity vs. frequency illustrating the result in the frequency domain of a simulated spectra in which a phase ratio of activation durations of two electric field activation sources in a two-phase application is set to 3 and the activation durations of the two electric field activation sources are swept over a range of frequencies according to the process illustrated in FIG. 25.

Referring now to FIG. 26A, a plot of ion intensity vs. frequency is shown illustrating the result in the frequency domain of a simulated spectrum resulting from the process 800 of FIG. 25 in which a phase ratio of activation durations of two electric field activation sources in a two-phase application is selected to be 3, and the activation durations of the two electric field activation sources are swept over a range of frequencies. The simulated spectrum illustrated in FIG. 26A illustratively uses approximately the same fundamental frequency, $f_f$, as the simulated spectrum illustrated in FIG. 23A, such that $f_f≈2$ kHz. According to the equations $m_{eq}=(ζ+1)/2$ and $f_{eq}=m_{eq}f_f$, the fundamental peak for ζ is the $m_{eq}=2$ peak that occurs at approximately $f_{eq}=2f_f≈4$ kHz. Since the illustrated example is of a 2-phase system, the SOMS system will have equivalent 3$^{rd}$, 5$^{th}$, 7$^{th}$, etc. overtones, and the equivalent 3$^{rd}$ overtone in the ζ=3 SOMS system is given by $m_{eq}=3((ζ+1)/2)=6$ which occurs approximately at $f_{eq}=6f_f≈12$ kHz.

It should be noted, as the plot of FIG. 26A illustrates, that the SOMS technique provides for overtones that are not observed in conventional OMS systems. In particular, for a 2-phase system, overtones in an OMS system include only the odd harmonics, whereas the SOMS result illustrated in FIG. 26A includes two even harmonics $m_{eq}=2$, at approximately 4 kHz and $m_{eq}=6$ at approximately 12 kHz. These harmonics at these frequencies generally are not observed in a conventional OMS system, although SOMS can clearly be used with ζ=3 to obtain an equivalent frequency and packet length to the second and sixth overtones.

Figure 26B:
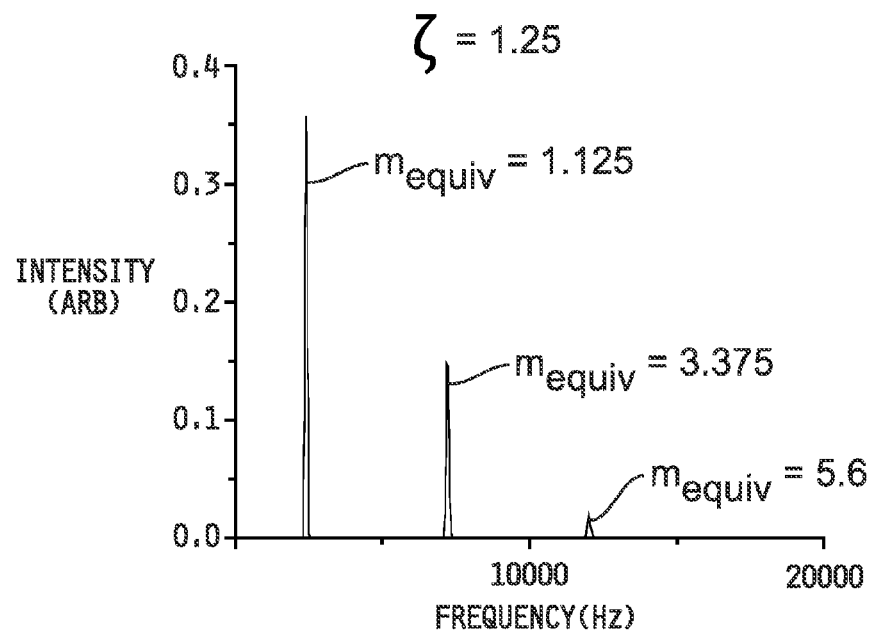
FIG. 26B is a plot of ion intensity vs. frequency illustrating the result in the frequency domain of a simulated spectra in which a phase ratio of activation durations of two electric field activation sources in a two-phase application is set to a non-integer number and the activation durations of the two electric field activation sources are swept over a range of frequencies according to the process illustrated in FIG. 25.

It should further be noted that SOMS does not require ζ to be an integer; only that it be non-negative and non-zero. Referring to FIG. 26B, for example, a plot is shown of ion intensity vs. frequency illustrating the result in the frequency domain of a simulated spectrum resulting from the process 800 of FIG. 25 in which a phase ratio of activation durations of two electric field activation sources in a two-phase application is selected to be the non-integer value 1.25, and the activation durations of the two electric field activation sources are swept over a range of frequencies according to the process illustrated in FIG. 25. The simulated spectrum illustrated in FIG. 26B illustratively uses approximately the same fundamental frequency, $f_f$, as the simulated spectrum illustrated in FIG. 23A, such that $f_f≈2$ kHz. According to the equations $m_{eq}=(ζ+1)/2$ and $f_{eq}=m_{eq}f_f$, the fundamental peak for ζ=1.25 is the $m_{eq}=1.125$ peak that occurs at approximately $f_{eq}=1.125f_f≈2.5$ kHz. Since the illustrated example is of a 2-phase system, the SOMS system will have equivalent 3$^{rd}$, 5$^{th}$, 7$^{th}$, etc. overtones. The equivalent 3$^{rd}$ overtone in the ζ=1.25 SOMS system is given by $m_{eq}=3((ζ+1)/2)=3.375$ which occurs approximately at $f_{eq}=3.375f_f≈6.75$ kHz, and the equivalent 5$^{th}$ overtone in the ζ=1.25 SOMS system is given by $m_{eq}=5((ζ+1)/2)=5.625$ which occurs approximately at $f_{eq}=5.625f_f≈11.25$ kHz.

The ability to set the phase ratio, ζ, to any positive real number greater than zero allows for substantially any equivalent overtone between the fundamental overtone for the given ζ and $ζ_{max}$ to be generated. This results in the ability to collect nearly an unlimited number of distinct data points as compared with only a small number of defined overtones using OMS.

Figure 27:
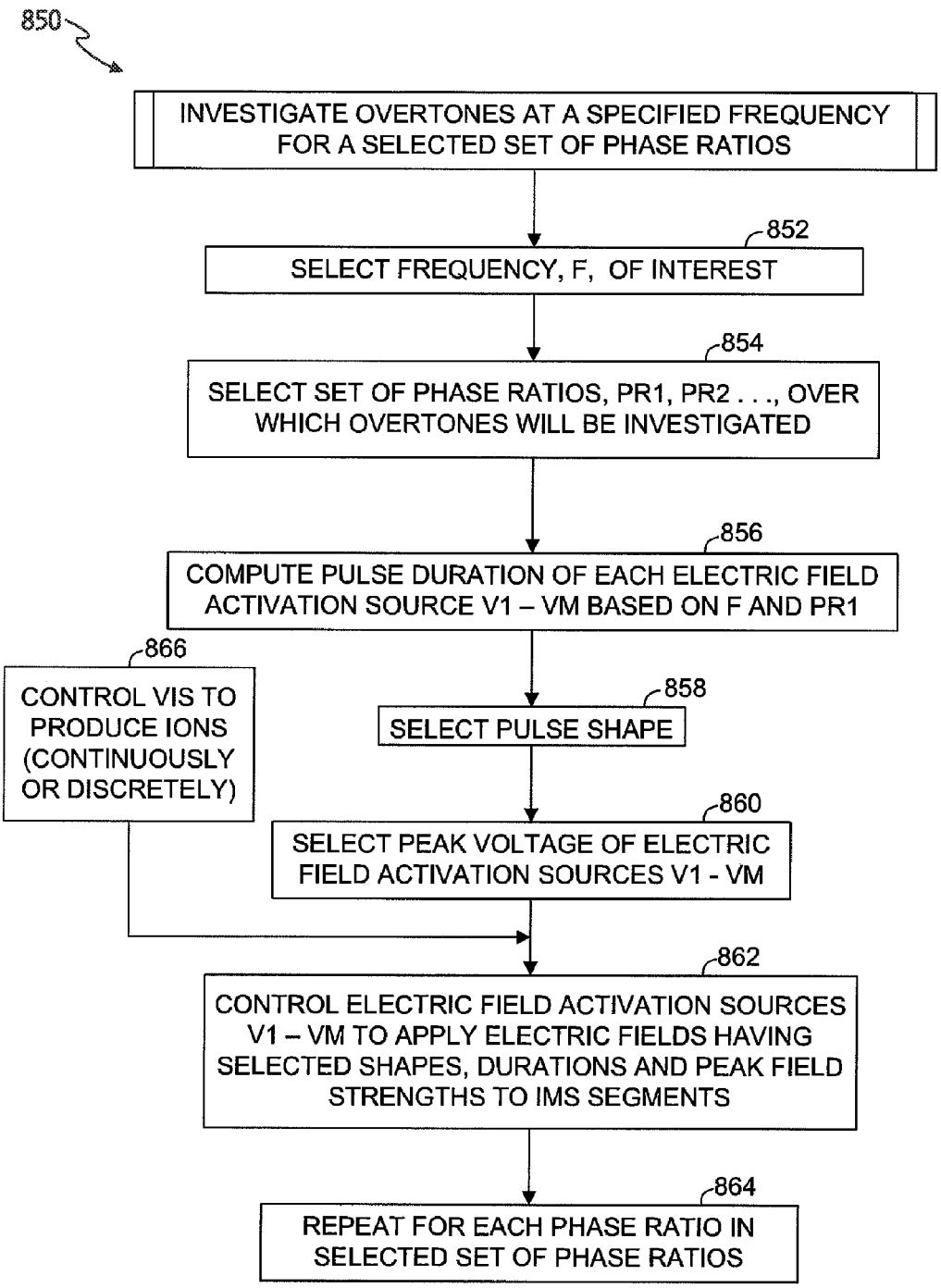
FIG. 27 is a flowchart of a process for operating a two-phase ion mobility spectrometer of the type illustrated and described herein by selecting an operating frequency of interest and changing phase ratios of the activation durations of the two electric field activation sources over a range of phase ratios to investigate overtones at the selected frequency for the selected set of phase ratios.

Referring now to FIG. 27, a flowchart is shown of an illustrative process 850 for investigating overtones at a specified frequency for a selected set of phase ratios, ζ. The process 850 illustrated in FIG. 27 may be provided, in whole or in part, in the form of instructions that are stored in the memory unit 20 of the control circuit 18 and that are executable by the control circuit 18 to control an ion mobility spectrometer instrument, e.g., of the type illustrated and described herein, in accordance with the process 850. The process 850 begins at step 852 where a frequency (or small frequency range) of interest is selected. Thereafter at step 854, a set of phase ratios, PR1, PR2, . . . , is selected, over which overtones will be investigated. It should be noted that a selection of the series of phase ratios, PR1, PR2, . . . , rather than sweeping or scanning ζ from 1 to $ζ_{max}$, avoids duplication as some overtones will be generated for multiple values of ζ (e.g., the 9$^{th}$ overtone can be observed in the data from the 3$^{rd}$ overtone).

In any case, the process 850 advances from step 854 to step 856 where the pulse durations of each of the electric field activation sources $V_1$-$V_M$ used in the ion mobility spectrometer instrument are computed. The pulse durations for each of the electric field activation sources $V_1$-$V_M$ can be determined using well-known equations based on the frequency, F, determined at step 852 and on the first phase ratio, PR1, in the set of phase ratios determined at step 854. Thereafter at step 858, the shape of the pulse width is selected, and thereafter at step 860 the peak voltage of the electric field activation sources $V_1$-$V_M$ is selected. The process 850 advances from step 860 to step 862, and simultaneously with step 860 the ion source voltage supply, $V_{IS}$, is controlled at step 866 in a manner that causes the ion source, e.g., the ion source 12, to produce ions. The ions produced at step 866 may be produced continuously or may instead be produced discretely as described hereinabove. In any case, the control circuit 18 is subsequently operable at step 862 to control the electric field activation sources $V_1$-$V_M$, as described hereinabove, to apply electric fields having the selected shapes, durations and peak field strengths to the various drift tube segments, $S_1$-$S_N$ as described hereinabove by example with reference to FIGS. 2-4D. Thereafter at step 864, the steps 852-866 are repeated for the next phase ratio in the set of selected phase ratios until the steps 852-866 are executed for the last phase ratio in the set. It will be understood that steps 852-866 are not required to be executed in the illustrated order, and that one or more of these steps may alternatively be interchanged with one or more other of these steps.

Figure 28:
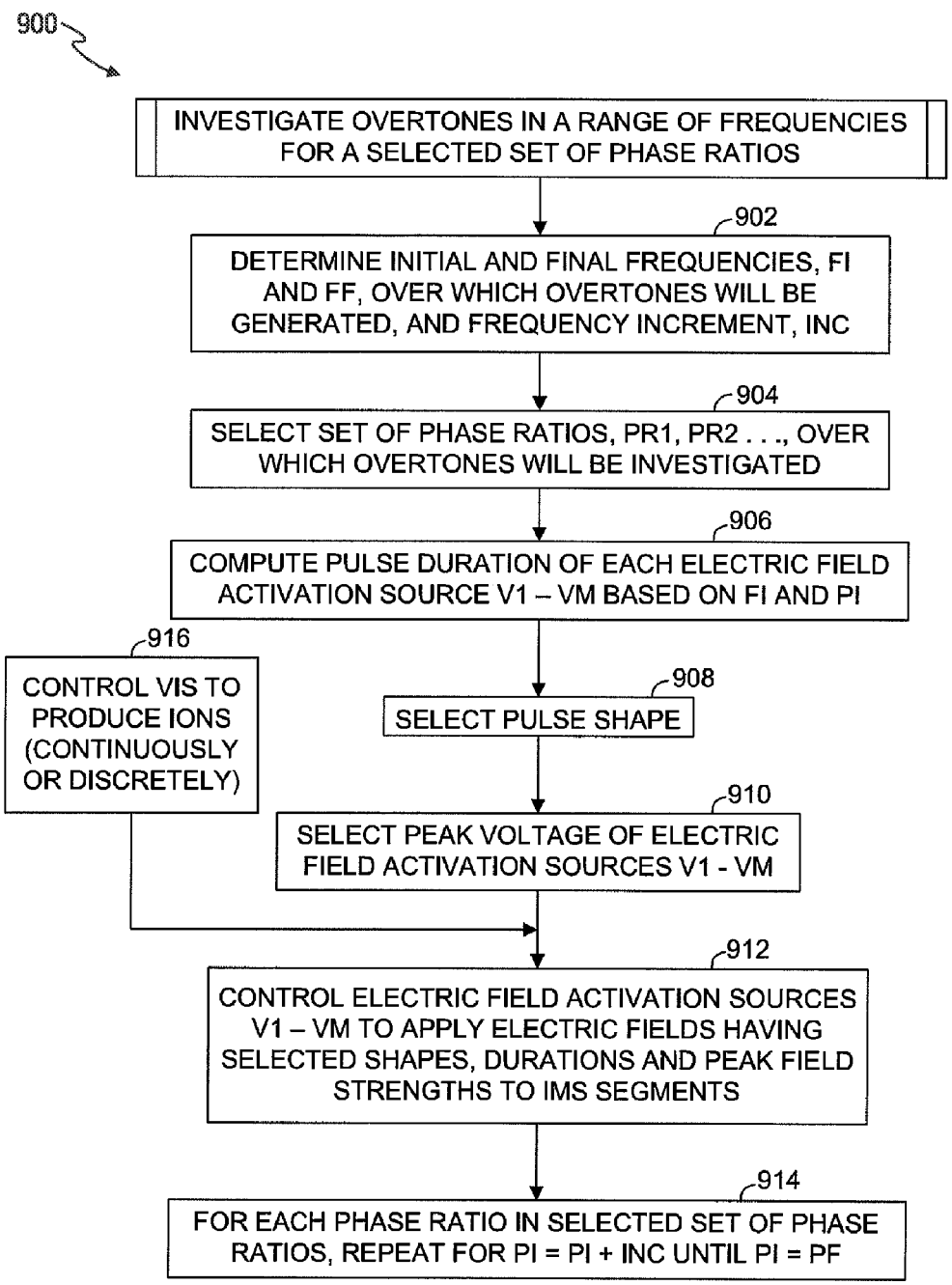
FIG. 28 is a flowchart of a process for operating a two-phase ion mobility spectrometer of the type illustrated and described herein by selecting sweeping the electric field activation source operating frequency over a range of frequencies for each of number of different phase ratios of the activation durations of the two electric field activation sources to investigate overtones in a range of frequencies for the selected set of phase ratios.

Referring now to FIG. 28, a flowchart is shown of an illustrative process 900 for investigating overtones in a range of frequencies for a selected set of phase ratios, $\zeta$. The process 900 illustrated in FIG. 28 may be provided, in whole or in part, in the form of instructions that are stored in the memory unit 20 of the control circuit 18 and that are executable by the control circuit 18 to control an ion mobility spectrometer instrument, e.g., of the type illustrated and described herein, in accordance with the process 900. The process 900 begins at step 902 where initial and final frequencies, FI and FF, over which a set of overtones will be generated, and a frequency increment, INC, is also selected. Illustratively, the initial frequency, FI, may be selected to produce an electrical field activation duration that is slightly longer than necessary to produce the fundamental ion intensity peak for the SOMS system so that the resulting ion intensity vs. frequency spectrum begins approximately at this fundamental peak. As in the processes 750 and 800, this initial frequency, FI, is the frequency, $f_{eq}$, at which the equivalent overtone occurs relative to the fundamental frequency, $f_f$, of the OMS system, and is given by the relationship $f_{eq}=m_{eq}f_f$, where $m_{eq}$ can be determined from the selected phase ratio, $\zeta$, according to the relationship $m_{eq}=(\zeta+1)/2$. Illustratively, the final frequency, FF, may be selected to be a frequency beyond which no useful information is expected to occur, or beyond which no ion intensity information is sought. In any case, the frequency increment, INC, will typically be selected to provide desired a frequency resolution.

Following step 902, the process 900 advances to step 904 where a set of phase ratios, PR1, PR2, . . . , is selected, over which overtones will be investigated. It should be noted again that a selection of the series of phase ratios, PR1, PR2, . . . , rather than sweeping or scanning $\zeta$ from 1 to $\zeta_{max}$, avoids duplication as some overtones will be generated for multiple values of $\zeta$. In any case, the process 900 advances from step 904 to step 906 where the pulse durations of each of the electric field activation sources $V_1$-$V_M$ used in the ion mobility spectrometer instrument are computed. The pulse durations for each of the electric field activation sources $V_1$-$V_M$ can be determined using well-known equations based on the initial frequency, FI, determined at step 902 and on the first phase ratio, PR1, in the set of phase ratios determined at step 904. Thereafter at step 908, the shape of the pulse width is selected, and thereafter at step 910 the peak voltage of the electric field activation sources $V_1$-$V_M$ is selected. The process 900 advances from step 910 to step 912, and simultaneously with step 910 the ion source voltage supply, $V_{IS}$, is controlled at step 916 in a manner that causes the ion source, e.g., the ion source 12, to produce ions. The ions produced at step 916 may be produced continuously or may instead be produced discretely as described hereinabove. In any case, the control circuit 18 is subsequently operable at step 912 to control the electric field activation sources $V_1$-$V_M$, as described hereinabove, to sequentially apply electric fields having the selected shapes, durations and peak field strengths to the various drift tube segments, $S_1$-$S_N$ as described hereinabove by example with reference to FIGS. 2-4D. Thereafter at step 914, the steps 902-916 are repeated for FI=FI+INC until the steps 902-916 are executed for the final frequency, FF, and this entire process is then repeated for each phase ratio in the set of selected phase ratios until the steps 902-916 are executed for the last phase ratio in the set. It will be understood that steps 912-916 are not required to be executed in the illustrated order, and that one or more of these steps may alternatively be interchanged with one or more other of these steps.

The various concepts relating to the SOMS system have been described with reference to the simplest case; a 2-phase system. In a 2-phase system, only a single phase ratio, $\zeta$, may exist, although it can be shown that, in general, a maximum number of phase ratios, $MAX_\zeta$, for any multiple-phase system is defined by the relationship $Max_\zeta=\phi-1$. In the simplest case in which any such multiple-phase system defines only a single phase ratio, $\zeta$, it can be shown that a generalized formula for determining an equivalent overtone as a function of phase, $\phi$, and phase ratio, $\zeta$, is given by $m_{\phi\zeta h}=[\phi h+1][(\phi-1)\zeta+1]/\phi$, where h is an integer index beginning with zero and having a step size of one, which occurs at the frequency $f_{eq}=m_{\phi\zeta h}f_f$. Two special cases of this formula are noteworthy. The first is the simplest case for this formula in which $\zeta=1$ and $h=0$, and under these conditions the foregoing formula reduces to the OMS case. The second special case is where $h=0$ and $\zeta>1$, and under these conditions the above formula produces the fundamental peak of the SOMS system defined by $\phi$ and $\zeta$. Those skilled in the art will appreciate that in multiple-phase systems which define more than one phase ratio, the foregoing formula for determining an equivalent overtone as a function of phase, $\phi$, and phase ratio, $\zeta$, will be more complicated, and in this regard the foregoing formula serves as a starting point for determining such equivalent overtone values.

While the invention has been illustrated and described in detail in the foregoing drawings and description, the same is to be considered as illustrative and not restrictive in character, it being understood that only illustrative embodiments thereof have been shown and described and that all changes and modifications that come within the spirit of the invention are desired to be protected. For example, it will be understood that the various techniques and processes illustrated and described herein may alternatively or additionally be implemented using one or more variants of any of the ion mobility spectrometers illustrated in the attached figures and described hereinabove. As one example, any such ion mobility spectrometer may be modified to replace one or more of the mesh gates, e.g., the 90% transmittance first and last rings $30_1$ and $30_5$ of each drift tube section, $S_1$, $S_2$, . . . , with so-called grid-less gates, e.g., annular rings similar or identical to the concentric rings $30_2$-$30_4$ positioned between the ion gates $30_1$ and $30_5$. Those skilled in the art will recognize other modifications that may be made to any of the ion mobility spectrometers illustrated in the attached figures and described hereinabove, and any such modifications are contemplated by this disclosure.

What is claimed is:

1. A method of separating ions as a function of ion mobility in a drift tube partitioned into a plurality of cascaded drift tube segments beginning with a first drift tube segment and advancing sequentially to a last drift tube segment, each drift tube segment defining an ion inlet at one end and an ion outlet at an opposite end, the drift tube further including an ion elimination region between an ion outlet of each drift tube segment and an ion inlet of a next adjacent drift tube segment, the ion elimination regions beginning with a first ion elimination region between the ion outlet of the first drift tube segment and the ion inlet of a second drift tube segment and advancing sequentially to a last ion elimination region coupled to the ion outlet of the last drift tube segment, for any integer M greater than 1 the method comprising:

repeating the following step multiple times to cause only ions entering the ion inlet of the first drift tube segment that have a predefined ion mobility or range of ion mobilities to traverse the drift tube, for each integer N beginning with 1 and sequentially advancing to M, establishing for a time duration an Nth electric repulsive field in the Nth ion elimination region and in every following Mth ion elimination region while establishing for the time duration an Nth electric drift field in each remaining ion elimination region and in each of the plurality of drift tube segments and while deactivating for the time duration all non-Nth electric drift fields and non-Nth electric repulsive fields in each of the ion elimination regions and in each of the plurality of drift tube segments.

2. The method of claim 1 wherein the last ion elimination region is coupled between the ion outlet of the last drift tube segment and the ion inlet of the first drift tube segment such that the drift tube defines therein a closed and continuous ion travel path, wherein the drift tube includes an ion entrance drift tube segment coupled to one of the plurality of drift tube segments, an ion exit drift tube segment coupled to another one of the plurality of drift tube segments and a plurality of ion gates each controllable to pass ions therethrough or block ions from passing therethrough, and wherein the method further comprises:

controlling one or more of the plurality of ion gates to introduce ions into the via the ion entrance drift tube segment, controlling one or more of the plurality of ion gates to direct ions in the drift tube along the continuous ion travel path while blocking ions from exiting the drift tube via the ion exit drift tube segment, after the ions in the drift tube have traveled along the continuous ion travel path a selected number of times, controlling one or more of the plurality of ion gates to direct at least some of the ions in the drift tube through the ion exit drift tube segment and out of the drift tube.

3. The method of claim 1 wherein a fundamental frequency is defined by a ratio of a total number of the plurality of drift tube segments and a total drift time through the drift tube of ions having the ion mobility or range of ion mobilities, and wherein the method further comprises repeating multiple times the step of establishing the electric drift fields and the electric repulsive fields for each of a plurality of different time durations to cause ions entering the ion inlet of the first drift tube segment that have an ion mobility or range of ion mobilities at a number of different overtone frequencies that are functionally related to the fundamental frequency to traverse the drift tube.

4. The method of claim 3 wherein the last ion elimination region is coupled between the ion outlet of the last drift tube segment and the ion inlet of the first drift tube segment such that the drift tube defines therein a closed and continuous ion travel path, wherein the drift tube includes an ion entrance drift tube segment coupled to one of the plurality of drift tube segments, an ion exit drift tube segment coupled to another one of the plurality of drift tube segments and a plurality of ion gates each controllable to pass ions therethrough or block ions from passing therethrough, and wherein the method further comprises:

controlling one or more of the plurality of ion gates to introduce ions into the via the ion entrance drift tube segment, controlling one or more of the plurality of ion gates to direct ions in the drift tube along the continuous ion travel path while blocking ions from exiting the drift tube via the ion exit drift tube segment, after the ions in the drift tube have traveled along the continuous ion travel path a selected number of times, controlling one or more of the plurality of ion gates to direct at least some of the ions in the drift tube through the ion exit drift tube segment and out of the drift tube.

5. The method of claim 1 wherein the time duration of one set of the M electric repulsive and electric drift fields is different than the time duration of the remaining sets of the M electric repulsive and electric drift fields, and wherein a ratio of the time duration of the one set of the M electric repulsive and electric drift fields and the time duration of the remaining sets of the M electric repulsive and electric drift fields defines a phase ratio that is greater than zero and not equal to unity.

6. The method of claim 5 wherein the last ion elimination region is coupled between the ion outlet of the last drift tube segment and the ion inlet of the first drift tube segment such that the drift tube defines therein a closed and continuous ion travel path, wherein the drift tube includes an ion entrance drift tube segment coupled to one of the plurality of drift tube segments, an ion exit drift tube segment coupled to another one of the plurality of drift tube segments and a plurality of ion gates each controllable to pass ions therethrough or block ions from passing therethrough, and wherein the method further comprises:

controlling one or more of the plurality of ion gates to introduce ions into the via the ion entrance drift tube segment, controlling one or more of the plurality of ion gates to direct ions in the drift tube along the continuous ion travel path while blocking ions from exiting the drift tube via the ion exit drift tube segment, after the ions in the drift tube have traveled along the continuous ion travel path a selected number of times, controlling one or more of the plurality of ion gates to direct at least some of the ions in the drift tube through the ion exit drift tube segment and out of the drift tube.

7. The method of claim 5 wherein a fundamental frequency is defined by a ratio of a total number of the plurality of drift tube segments and a total drift time through the drift tube of ions having the ion mobility or range of ion mobilities, and wherein the method further comprises repeating multiple times the step of establishing the electric drift fields and the electric repulsive fields for each of a plurality of different time durations to cause ions entering the ion inlet of the first drift tube segment that have an ion mobility or range of ion mobilities at a number of different overtone frequencies to traverse the drift tube, wherein each of the number of different overtone frequencies is a function of the fundamental frequency, the phase ratio and the integer M.

8. The method of claim 7 wherein the last ion elimination region is coupled between the ion outlet of the last drift tube segment and the ion inlet of the first drift tube segment such that the drift tube defines therein a closed and continuous ion travel path, wherein the drift tube includes an ion entrance drift tube segment coupled to one of the plurality of drift tube segments, an ion exit drift tube segment coupled to another one of the plurality of drift tube segments and a plurality of ion gates each controllable to pass ions therethrough or block ions from passing therethrough, and wherein the method further comprises:

controlling one or more of the plurality of ion gates to introduce ions into the via the ion entrance drift tube segment, controlling one or more of the plurality of ion gates to direct ions in the drift tube along the continuous ion travel path while blocking ions from exiting the drift tube via the ion exit drift tube segment, after the ions in the drift tube have traveled along the continuous ion travel path a selected number of times, controlling one or more of the plurality of ion gates to direct at least some of the ions in the drift tube through the ion exit drift tube segment and out of the drift tube.

9. The method of claim 5 wherein a fundamental frequency is defined by a ratio of a total number of the plurality of drift tube segments and a total drift time through the drift tube of ions having the ion mobility or range of ion mobilities, and wherein the method further comprises repeating multiple times the step of establishing the electric drift fields and the electric repulsive fields with a sum of the time durations of each Nth electric repulsive and drift fields defined as a ratio of M and the fundamental frequency to cause ions entering the ion inlet of the first drift tube segment that have an ion mobility or range of ion mobilities at an overtone frequency to traverse the drift tube, wherein the overtone frequency is defined by the relationship (phase ratio+1)/2.

10. The method of claim 9 wherein the last ion elimination region is coupled between the ion outlet of the last drift tube segment and the ion inlet of the first drift tube segment such that the drift tube defines therein a closed and continuous ion travel path, wherein the drift tube includes an ion entrance drift tube segment coupled to one of the plurality of drift tube segments, an ion exit drift tube segment coupled to another one of the plurality of drift tube segments and a plurality of ion gates each controllable to pass ions therethrough or block ions from passing therethrough, and wherein the method further comprises:

controlling one or more of the plurality of ion gates to introduce ions into the via the ion entrance drift tube segment, controlling one or more of the plurality of ion gates to direct ions in the drift tube along the continuous ion travel path while blocking ions from exiting the drift tube via the ion exit drift tube segment, after the ions in the drift tube have traveled along the continuous ion travel path a selected number of times, controlling one or more of the plurality of ion gates to direct at least some of the ions in the drift tube through the ion exit drift tube segment and out of the drift tube.

\* \* \* \* \*